(12) United States Patent
Malamas et al.

(10) Patent No.: US 7,423,158 B2
(45) Date of Patent: Sep. 9, 2008

(54) AMINO-5-[4-(DIFLUOROMETHOXY) PHENYL]-5-PHENYLIMIDAZOLONE COMPOUNDS FOR THE INHIBITION OF β-SECRETASE

(75) Inventors: Michael Sotirios Malamas, Jamison, PA (US); James Joseph Erdei, Philadelphia, PA (US); William Floyd Fobare, Lawrenceville, NJ (US); Dominick Anthony Quagliato, Bridgewater, NJ (US); Schuyler Adam Antane, Princeton Junction, NJ (US); Albert Jean Robichaud, Ringoes, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/526,511

(22) Filed: Sep. 25, 2006

(65) Prior Publication Data
US 2007/0072925 A1 Mar. 29, 2007

Related U.S. Application Data

(60) Provisional application No. 60/720,589, filed on Sep. 26, 2005.

(51) Int. Cl.
A61K 31/4168 (2006.01)
C07D 233/44 (2006.01)
(52) U.S. Cl. .................................. 548/321.5; 514/392
(58) Field of Classification Search ............... 548/321.5
See application file for complete search history.

(56) References Cited

U.S. PATENT DOCUMENTS

| 4,140,793 | A | 2/1979 | Ward |
|---|---|---|---|
| 4,225,613 | A | 9/1980 | Ward |
| 6,054,457 | A | 4/2000 | Setoi et al. |
| 6,399,824 | B1 | 6/2002 | Hofmeister et al. |
| 6,656,957 | B1 | 12/2003 | Allgeier et al. |
| 6,689,804 | B2 | 2/2004 | Wu et al. |
| 6,974,829 | B2 | 12/2005 | Tung et al. |
| 7,285,682 | B2 | 10/2007 | Hu |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0160828 | A1 | 7/2006 | Malamas et al. |
| 2006/0173049 | A1 | 8/2006 | Malamas et al. |
| 2006/0183790 | A1 | 8/2006 | Cole et al. |
| 2006/0183792 | A1 | 8/2006 | Fobare et al. |
| 2007/0004730 | A1 | 1/2007 | Zhou |
| 2007/0004786 | A1 | 1/2007 | Malamas et al. |
| 2007/0027199 | A1 | 2/2007 | Malamas et al. |
| 2007/0191431 | A1 | 8/2007 | Zhou |
| 2007/0203116 | A1 | 8/2007 | Quagliato et al. |
| 2008/0051390 | A1 | 2/2008 | Malamas et al. |

FOREIGN PATENT DOCUMENTS

| EP | 0861831 A1 | 9/1998 |
|---|---|---|
| GB | 2013192 A | 8/1979 |
| WO | WO 97/45417 A1 | 12/1997 |
| WO | 98/45267 | 10/1998 |
| WO | 01/87829 A1 | 11/2001 |
| WO | 03/053938 A1 | 7/2003 |
| WO | 03/064396 A1 | 8/2003 |
| WO | 03/094854 A2 | 11/2003 |
| WO | 2003/094854 A2 | 11/2003 |
| WO | 2004/058727 A1 | 7/2004 |
| WO | 2004058727 A1 | 7/2004 |
| WO | WO 2005/005412 A1 | 1/2005 |
| WO | 2005/058311 A1 | 6/2005 |
| WO | 2005/0058311 A1 | 6/2005 |
| WO | WO-2005/058311 A1 * | 6/2005 |
| WO | 2006/009653 A1 | 1/2006 |
| WO | 2006065277 A2 | 6/2006 |
| WO | 2007005404 A1 | 1/2007 |
| WO | 2007/016012 A2 | 2/2007 |

OTHER PUBLICATIONS

Yamada, Kiyoshi; Okitsu, Massayo; Ju, Liang Chieh; Nakanishi, Kazuyuki; Yamamoto, Junko, Oyo Yakuri (1975), 9(6), 841-7. (English language Abstract).
Abbott et al., Molecular Medicine Today, 1996, vol. 2, pp. 106-113.
Allimony et al., "Synthesis and antimicrobial activity of some nitrogen heterobicyclic systems: Part I", Indian Journal of Chemistry, 1999, vol. 38B, pp. 445-451.
Fact Sheet Alzheimer's Association, 2006.
Lefrance-Jullien et al., "Design and Charaterization of a new cell-permeant inhibitor of the beta-secretase BACE1", British Journal of Pharmacology, 2005, vol. 145, pp. 228-235.

(Continued)

*Primary Examiner*—Laura L. Stockton
(74) *Attorney, Agent, or Firm*—Joel B. Silver; Scott Larsen; Andrea Dorigo

(57) ABSTRACT

The present invention provides a 2-amino-5-[4-(difluoromethoxy)phenyl]-5-phenylimidazolone compound of formula I

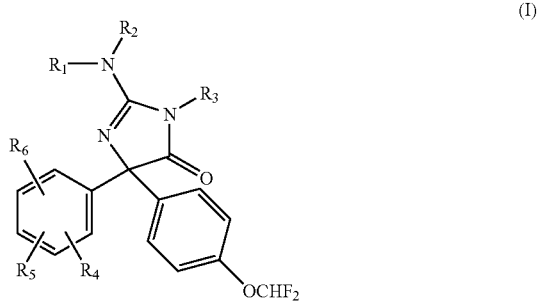

The present invention also provides methods for the use thereof to inhibit β-secretase (BACE) and treat β-amyloid deposits and neurofibrillary tangles.

15 Claims, No Drawings

OTHER PUBLICATIONS

Lyketsos et al., "Position statement of the American Association of Geriatric Psychiatry regarding principles of care for patients with dementia resulting from Alzheimer's Disease", 2006, vol. 14, pp. 561-573.

Alzheimer's Disease, retrieved from internet on Jun. 27, 2007, http://www.mayoclinic.com/health/alzheimers-disease/DA00161/Dsection-3.

National Institute of Neurological Disorders and Stroke, "Alzheimer's Disease Information Page", retrieved from internet on Jun. 27, 2007, http://www.ninds.nih.gov/disorders/alzheimersdisease.htm.

PCT Preliminary Report on Patentability, Written Opinion of the ISR, International Patent Application PCT/US2006/024793, International filing date Jun. 26, 2006.

PCT Preliminary Report on Patentability, Written Opinion of the ISR, International Patent Application PCT/US2006/024912, International filing dated Jun. 26, 2006.

Selkoe, "Alzheimer's Disease: Genes, Proteins and, Therapy", Physiological Reviews, 2001, vol. 81(2), pp. 741-766.

Su et al. "Drug delivery across the blood-brain barrier: why is it difficult? How to measure and improve it?", Expert Opinion on Drug Delivery, Abstract, 2006, vol. 3, pp. 419-425.

Tao et al., "Synthesis of Conformationally constrained spirohydantoins with a Dibenzo[a,d]heptadiene ring", Synthesis 2000, No. 10, pp. 1449-1453.

Vadana et al., "Transferring coupled liposomes as drug delivery carriers for brain targeting of the 5-flouracil", Journal of Drug Targeting, Abstract, 2005, vol. 13, pp. 245-250.

Varghese et al., "Human beta-secretase (BACE) and BACE Inhibitors", J. Med. Chem. 2003, vol. 46(22), pp. 4625-4630.

Xiao et al., "An improved procedure for the synthesis of 4,4-disubstituted-3-oxo-1,2,5-thiadiazolidine1, 1-dioxides", J. Heterocyclic Chem., 2000, vol. 37, pp. 773-777.

* cited by examiner

AMINO-5-[4-(DIFLUOROMETHOXY)PHENYL]-5-PHENYLIMIDAZOLONE COMPOUNDS FOR THE INHIBITION OF β-SECRETASE

This application claims the benefit under 35 U.S.C. § 119 (e) to U.S. provisional application No. 60/720,589, filed Sep. 26, 2005, which is hereby incorporated by reference in its entirety.

BACKGROUND

β-Amyloid deposits and neurofibrillary tangles are two major pathologic characterizations associated with Alzheimer's disease (AD). Clinically, AD is characterized by the of loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630).

β-amyloid deposits are predominately an aggregate of Aβ peptide, which in turn is a product of the proteolysis of amyloid precursor protein (APP). More specifically, Aβ peptide results from the cleavage of APP at the C-terminus by one or more γ-secretases, and at the N-terminus by β-secretase enzyme (BACE), also known as aspartyl protease, as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324).

Therefore, it is an object of this invention to provide compounds which are inhibitors of β-secretase and are useful as therapeutic agents in the treatment, prevention or amelioration of a disease or disorder characterized by elevated β-amyloid deposits or β-amyloid levels in a patient.

It is another object of this invention to provide therapeutic methods and pharmaceutical compositions useful for the treatment, prevention or amelioration of a disease or disorder characterized by elevated β-amyloid deposits or β-amyloid levels in a patient.

It is a feature of this invention that the compounds provided may also be useful to further study and elucidate the β-secretase enzyme.

These and other objects and features of the invention will become more apparent by the detailed description set forth hereinbelow.

SUMMARY OF THE INVENTION

The present invention provides a compound of formula I

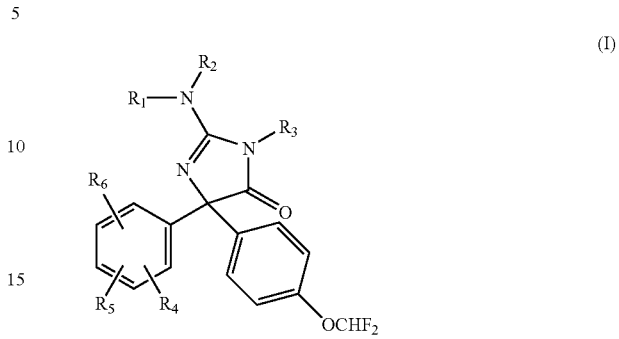

wherein
$R_1$ and $R_2$ are each independently H or an alkyl, cycloalkyl, cycloheteroalkyl, aryl or heteroaryl group each optionally substituted or $R_1$ and $R_2$ may be taken together with the atom to which they are attached form an optionally substituted 5- to 7-membered ring optionally interrupted by an additional heteroatom selected from O, N or S;

$R_3$ is H or an alkyl, cycloalkyl, cycloheteroalkyl, aryl or heteroaryl group each optionally substituted;

$R_4$, $R_5$ and $R_6$ are each independently H, halogen, $NO_2$, CN, $COR_7$, $NR_{10}CO_2R_{11}$, $NR_{15}COR_{16}$, $OR_{14}$, $NR_{12}R_{13}$, $SO_nR_{17}$ or an alkyl, haloalkyl, alkenyl, haloalkenyl, alkynyl, cycloalkyl or cycloheteroalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;

n is 0, 1 or 2;

$R_7$ and $R_{17}$ are each independently H, $NR_8R_9$ or an alkyl, haloalkyl, alkoxyalkyl, alkenyl, alkynyl, cycloalkyl or aryl group each optionally substituted;

$R_8$ and $R_9$ are each independently H or an alkyl, alkenyl, alkynyl or cycloalkyl group each optionally substituted or $R_8$ and $R_9$ may be taken together with the atom to which they are attached to form an optionally substituted 5- to 7-membered ring optionally containing an additional heteroatom selected from O, N or S;

$R_{11}$, $R_{14}$ and $R_{16}$ are each independently H or an alkyl, haloalkyl, alkoxyalkyl, alkenyl, alkynyl, cycloalkyl or aryl group each optionally substituted;

$R_{10}$ and $R_{15}$ are each independently H or an optionally substituted alkyl group; and $R_{12}$ and $R_{13}$ are each independently H or an alkyl or cycloalkyl group each optionally substituted or $R_{12}$ and $R_{13}$ may be taken together with the atom to which they are attached to form an optionally substituted 5- to 7-membered ring optionally containing an additional heteroatom selected from O, N or S; or a tautomer thereof, a stereoisomer thereof or a pharmaceutically acceptable salt thereof.

The present invention also relates to the use of such compounds for the treatment of β-amyloid deposits and neurofibrillary tangles. The formula I compounds are particularly useful in treating Alzheimer's disease, cognitive impairment, Down's Syndrome, HCHWA-D, cognitive decline, senile dementia, cerebral amyloid angiopathy, degenerative dementia, or other neurodegenerative disorders.

DETAILED DESCRIPTION OF THE INVENTION

Alzheimer's disease (AD) is a major degenerative disease of the brain which presents clinically by progressive loss of memory, cognition, reasoning, judgement and emotional stability and gradually leads to profound mental deterioration and death. The exact cause of AD is unknown, but increasing evidence indicates that amyloid beta peptide (A-beta) plays a central role in the pathogenesis of the disease. (D. B. Schenk; R. E. Rydel et al, Journal of Medicinal Chemistry, 1995, 21, 4141 and D. J. Selkoe, Physiology Review, 2001, 81, 741). Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemmorhage with Amyloidosis of the Dutch type and other neurodegenerative and dementia-inducing disorders. Overexpression of the amyloid precursor protein (APP), altered cleavage of APP to A-beta or a decrease in the clearance of A-beta from a patient's brain may increase the levels of soluble or fibrillar forms of A-beta in the brain. The β-site APP cleaving enzyme, BACE1, also called memapsin-2 or Asp-2, was identified in 1999 (R. Vassar, B. D. Bennett, et al, Nature, 1999, 402, 537). BACE1 is a membrane-bound aspartic protease with all the known functional properties and characteristics of β-secretase. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that amino-5-[4-(difluoromethoxy)phenyl]-5-phenylimidazolone compounds of formula I demonstrate inhibition of β-secretase and the selective inhibition of BACE1. Advantageously, said phenylimidazolone compounds may be used as effective therapeutic agents for the treatment, prevention or amelioration of a disease or disorder characterized by elevated β-amyloid deposits or β-amyloid levels in a patient. Accordingly, the present invention provides an amino-5-[4-(difluoromethoxy)phenyl]-5-phenylimidazolone compound of formula I

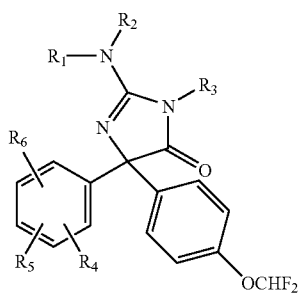

wherein $R_1$ and $R_2$ are each independently H or an alkyl, cycloalkyl, cycloheteroalkyl, aryl or heteroaryl group each optionally substituted or $R_1$ and $R_2$ may be taken together with the atom to which they are attached form an optionally substituted 5- to 7-membered ring optionally interrupted by an additional heteroatom selected from O, N or S;

$R_3$ is H or an alkyl, cycloalkyl, cycloheteroalkyl, aryl or heteroaryl group each optionally substituted;

$R_4$, $R_5$ and $R_6$ are each independently H, halogen, $NO_2$, CN, $COR_7$, $NR_{10}CO_2R_{11}$, $NR_{15}COR_{16}$, $OR_{14}$, $NR_{12}R_{13}$, $SO_nR_{17}$ or an alkyl, haloalkyl, alkenyl, haloalkenyl, alkynyl, cycloalkyl or cycloheteroalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;

n is 0, 1 or 2;

$R_7$ and $R_{17}$ are each independently H, $NR_8R_9$ or an alkyl, haloalkyl, alkoxyalkyl, alkenyl, alkynyl, cycloalkyl or aryl group each optionally substituted;

$R_8$ and $R_9$ are each independently H or an alkyl, alkenyl, alkynyl or cycloalkyl group each optionally substituted or $R_8$ and $R_9$ may be taken together with the atom to which they are attached to form an optionally substituted 5- to 7-membered ring optionally containing an additional heteroatom selected from O, N or S;

$R_{11}$, $R_{14}$ and $R_{16}$ are each independently H or an alkyl, haloalkyl, alkoxyalkyl, alkenyl, alkynyl, cycloalkyl or aryl group each optionally substituted;

$R_{10}$ and $R_{15}$ are each independently H or an optionally substituted alkyl group; and $R_{12}$ and $R_{13}$ are each independently H or an alkyl or cycloalkyl group each optionally substituted or $R_{12}$ and $R_{13}$ may be taken together with the atom to which they are attached to form an optionally substituted 5- to 7-membered ring optionally containing an additional heteroatom selected from O, N or S; or a tautomer thereof, a stereoisomer thereof or a pharmaceutically acceptable salt thereof.

It is understood that the claims encompass all possible stereoisomers and prodrugs. Moreover, unless stated otherwise, each alkyl, alkoxy, alkenyl, alkynyl, cycloalkyl, cycloheteroalkyl, aryl or heteroaryl group is contemplated as being optionally substituted.

An optionally substituted moiety may be substituted with one or more substituents. The substituent groups which are optionally present may be one or more of those customarily employed in the development of pharmaceutical compounds or the modification of such compounds to influence their structure/activity, persistence, absorption, stability or other beneficial property. Specific examples of such substituents include halogen atoms, nitro, cyano, thiocyanato, cyanato, hydroxyl, alkyl, haloalkyl, alkoxy, haloalkoxy, aryloxy, amino, alkylamino, dialkylamino, formyl, carbonyl, alkoxycarbonyl, carboxyl, alkanoyl, alkylthio, alkylsulfinyl, alkylsulfonyl, carbamoyl, alkylamido, phenyl, phenoxy, benzyl, benzyloxy, cycloalkyl or cycloheteroalkyl groups, preferably halogen atoms, lower alkyl or lower alkoxy groups, wherein 'lower' is from 1 to 4 carbon atoms. In one embodiment the substituent groups may be selected from halo, cyano, hydroxy, alkyl, alkenyl, alkynyl, alkoxy or cycloalkyl. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term "alkyl" includes both straight chain and branched-chain (unless defined otherwise)

monovalent saturated hydrocarbon moieties of 1-12 carbon atoms, preferably 1-6 carbon atoms, more preferably 'lower' alkyl of 1-4 carbon atoms. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Alkyl groups can be optionally substituted. Suitable alkyl substitutions include, but are not limited to, CN, OH, halogen, alkenyl, alkynyl, cycloalkyl, phenyl, carbamoyl, carbonyl, alkoxy or aryloxy.

As used herein the term "haloalkyl" designates a $C_nH_{2n+1}$ group having from one to 2n+1 halogen atoms which may be the same or different. Examples of haloalkyl groups include $CF_3$, $CH_2Cl$, $C_2H_3BrCl$, $C_3H_5F_2$, or the like. Similarly, the term haloalkoxy designates an $OC_nH_{2n+1}$ group having from one to 2n+1 halogen atoms which may be the same or different.

The term "alkoxyalkyl" as used herein, refers to an alkyl group as hereinbefore defined substituted with at least one $C_1$-$C_4$ alkoxy group.

The term "alkenyl", as used herein, refers to either a straight chain or branched-chain hydrocarbon moiety containing at least one double bond and having from 2-12 carbon atoms, preferably 2-6 carbon atoms, more preferably 2-4 carbon atoms. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like.

The term "haloalkenyl" as used herein, designates an alkenyl group as defined hereinabove substituted with one or more halogen atoms which may be the same or different.

The term "alkynyl", as used herein, refers to an alkyl group having one or more triple carbon-carbon bonds. Alkynyl groups preferably contain 2 to 6 carbon atoms. Examples of alkynyl groups include, but are not limited to, ethynyl, propynyl, butynyl, pentynyl, and the like. In some embodiments, alkynyl groups can be substituted with up to four substituent groups, as described hereinabove.

The term "cycloalkyl", as used herein, refers to a monocyclic, bicyclic, tricyclic, fused, bridged, or spiro saturated carbocyclic moiety of 3-10 carbon atoms. Any suitable ring position of the cycloalkyl moiety may be covalently linked to the defined chemical structure. Examples of cycloalkyl moieties include, but are not limited to, chemical groups such as cyclopropyl, cyclobutyl, cyclopentyl, cyclohexyl, cycloheptyl, norbornyl, adamantyl, spiro[4.5]decanyl, and homologs, isomers, or the like.

The term "cycloheteroalkyl" as used herein designates a 5- to 7-membered cycloalkyl ring system containing 1, 2 or 3 heteroatoms, which may be the same or different, selected from N, O or S, and optionally containing one double bond. Exemplary of the cycloheteroalkyl ring systems included in the term as designated herein are the following rings wherein $X_1$ is NR', O or S, and R' is H or an optional substituent as defined hereinabove.

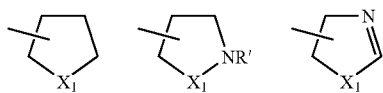

-continued

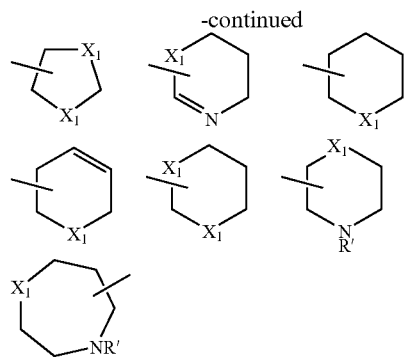

The term "aryl", as used herein, designates an aromatic carbocyclic moiety of up to 20 carbon atoms, e.g. 6-20 carbon atoms, which may be a single ring (monocyclic) or multiple rings (bicyclic, up to three rings) fused together or linked covalently. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. In some embodiments "aryl" groups can be substituted with from 1-5 substituents.

The term "heteroaryl" as used herein designates an aromatic heterocyclic ring system, e.g. having from 5-20 ring atoms, which may be a single ring (monocyclic) or multiple rings (bicyclic, up to three rings) fused together or linked covalently. Preferably, heteroaryl is a 5- to 6-membered ring. The rings may contain from one to four hetero atoms selected from nitrogen, oxygen, or sulfur, wherein the nitrogen or sulfur atom(s) are optionally oxidized, or the nitrogen atom(s) are optionally quaternized. Examples of heteroaryl moieties include, but are not limited to, heterocycles such as furan, thiophene, pyrrole, pyrazole, imidazole, oxazole, isoxazole, thiazole, isothiazole, 1H-tetrazole, 1,3,4-oxadiazole, 1H-1,2,4-triazole, 1,3,4-triazole, pyridine, pyrimidine, pyrazine, pyridazine, benzoxazole, benzisoxazole, benzothiazole, benzofuran, benzothiophene, thianthrene, benzimidazole, indole, indazole, quinoline, isoquinoline, quinazoline, quinoxaline, purine, pteridine, 9H-carbazole, α-carboline, or the like.

The term "halogen", as used herein, designates fluorine, chlorine, bromine, or iodine.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethyl-propylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Compounds of the invention may exist as one or more tautomers. One skilled in the art will recognize that compounds of formula I may also exist as the tautomer It as shown below.

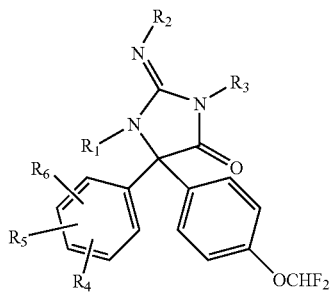
(It)

Tautomers often exist in equilibrium with each other. As these tautomers interconvert under environmental and physiological conditions, they provide the same useful biological effects. The present invention includes mixtures of such tautomers as well as the individual tautomers, for example the compounds of Formulas I, It, Ita, Itb and the like.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one steriosomer, preferably less than about 50%, more preferably less than about 75%, and even more preferably less than about 90%.

Preferred compounds of formula I are those compounds wherein $R_1$ and $R_2$ are H. Another group of preferred compounds are those compounds of formula I wherein $R_3$ is $C_1$-$C_4$alkyl. Also preferred are those compounds of formula I wherein $R_4$, $R_5$ and $R_6$ are each independently H, halogen, $COR_7$, $OR_{14}$, or an alkyl, haloalkyl, alkoxy, haloalkoxy, alkynyl or cycloalkyl group each optionally substituted.

More preferred compounds of the invention are those compounds of formula I wherein $R_1$ and $R_2$ are H and $R_3$ is methyl. Another group of more preferred compounds of the invention are those compounds of formula I wherein $R_4$ is H, $COR_7$, $OR_{14}$ or an alkyl, haloalkyl, alkoxy, haloalkoxy, alkynyl or cycloalkyl group each group optionally substituted; and $R_5$ and $R_6$ are each independently H or halogen. In one embodiment $R_4$ is optionally substituted with one or more groups selected from alkenyl, alkynyl, halo, hydroxy, alkoxy or cycloalkyl. In another embodiment $R_4$ is at the 3-position of the phenyl ring.

A further group of more preferred compounds of the invention are those compounds of formula I wherein $R_1$ and $R_2$ are H; $R_3$ is methyl; $R_4$ is H, $COR_7$ or an alkyl, haloalkyl, alkoxy, haloalkoxy, alkynyl or cycloalkyl group each group optionally substituted; $R_5$ and $R_6$ are each independently H or halogen; and $R_4$ is at the 3-position of the phenyl ring.

Preferred compounds of the invention include:
(5S)-2-Amino-5-[4-(difluoromethoxy)phenyl]-3-methyl-5-phenyl-3,5-dihydro-4H-imidazol-4-one;
(5R)-2-Amino-5-[4-(difluoromethoxy)-phenyl]-3-methyl-5-phenyl-3,5-dihydro-4H-imidazol-4-one;
(5R)-2-amino-5-(3-bromophenyl)-5-[4-(difluoromethoxy)phenyl]-3-methyl-3,5-dihydro-4H-imidazol-4-one;
(5S)-2-amino-5-(3-bromophenyl)-5-[4-(difluoromethoxy)phenyl]-3-methyl-3,5-dihydro-4H-imidazol-4-one;
(5R)-2-Amino-5-(3-bromo-4-fluorophenyl)-5-[4-(difluoromethoxy)phenyl]-3-methyl-3,5-dihydro-4H-imidazol-4-one;
(5S)-2-Amino-5-(3-bromo-4-fluorophenyl)-5-[4-(difluoromethoxy)phenyl]-3-methyl-3,5-dihydro-4H-imidazol-4-one;
(5R)-2-Amino-5-[4-(difluoromethoxy)phenyl]-3-methyl-5-(3-propylphenyl)-3,5-dihydro-4H-imidazol-4-one;
(5S)-2-Amino-5-[4-(difluoromethoxy)phenyl]-3-methyl-5-(3-propylphenyl)-3,5-dihydro-4H-imidazol-4-one;
2-Amino-5-[4-(difluoromethoxy)phenyl]-5-[3-(3-fluoropropyl)phenyl]-3-methyl-3,5-dihydro-4H-imidazol-4-one;
2-Amino-5-[4-(difluoromethoxy)phenyl]-5-[3-(3,3-difluoropropyl)phenyl]-3-methyl-3,5-dihydro-4H-imidazol-4-one;
2-Amino-5-[4-(difluoromethoxy)phenyl]-5-[3-(4-fluorobutyl)phenyl]-3-methyl-3,5-dihydro-4H-imidazol-4-one;
2-Amino-5-[3-(4,4-difluorobutyl)phenyl]-5-[4-(difluoromethoxy)phenyl]-3-methyl-3,5-dihydro-4H-imidazol-4-one;
2-Amino-5-[4-(difluoromethoxy)phenyl]-5-[3-(2-fluoroethyl)phenyl]-3-methyl-3,5-dihydro-4H-imidazol-4-one;
2-Amino-5-[3-(2,2-difluoroethyl)phenyl]-5-[4-(difluoromethoxy)phenyl]-3-methyl-3,5-dihydro-4H-imidazol-4-one;
2-Amino-5-[4-(difluoromethoxy)phenyl]-3-methyl-5-[3-(2,2,2-trifluoroethyl)phenyl]-3,5-dihydro-4H-imidazol-4-one;
2-Amino-5-[4-(difluoromethoxy)phenyl]-3-methyl-5-[3-(3,3,3-trifluoropropyl)phenyl]-3,5-dihydro-4H-imidazol-4-one;
2-Amino-5-[4-(difluoromethoxy)phenyl]-3-methyl-5-[3-(4,4,4-trifluorobutyl)phenyl]-3,5-dihydro-4H-imidazol-4-one;
(5R)-2-amino-5-(3-butylphenyl)-5-[4-(difluoromethoxy)phenyl]-3-methyl-3,5-dihydro-4H-imidazol-4-one;
(5S)-2-amino-5-(3-butylphenyl)-5-[4-(difluoromethoxy)phenyl]-3-methyl-3,5-dihydro-4H-imidazol-4-one;
2-Amino-5-[4-(difluoromethoxy)phenyl]-3-methyl-5-(3-pentylphenyl)-3,5-dihydro-4H-imidazol-4-one;
2-Amino-5-[4-(difluoromethoxy)phenyl]-3-methyl-5-[3-(2-methylbutyl)phenyl]-3,5-dihydro-4H-imidazol-4-one;
2-Amino-5-(3-but-3-en-1-ylphenyl)-5-[4-(difluoromethoxy)phenyl]-3-methyl-3,5-dihydro-4H-imidazol-4-one;
2-Amino-5-[3-(cyclopropylmethyl)phenyl]-5-[4-(difluoromethoxy)phenyl]-3-methyl-3,5-dihydro-4H-imidazol-4-one;

3-(3-{2-Amino-4-[4-(difluoromethoxy)phenyl]-1-methyl-5-oxo-4,5-dihydro-1H-imidazol-4-yl}phenyl)propanenitrile;

(5R)-2-Amino-5-[4-(difluoromethoxy)phenyl]-3-methyl-5-(3-pent-4-en-1-ylphenyl)-3,5-dihydro-4H-imidazol-4-one;

(5S)-2-Amino-5-[4-(difluoromethoxy)phenyl]-3-methyl-5-(3-pent-4-en-1-ylphenyl)-3,5-dihydro-4H-imidazol-4-one;

N-(3-{(4R)-2-Amino-4-[4-(difluoromethoxy)phenyl]-1-methyl-5-oxo-4,5-dihydro-1H-imidazol-4-yl}phenyl)-2-methoxyacetamide;

N-(3-{(4S)-2-Amino-4-[4-(difluoromethoxy)phenyl]-1-methyl-5-oxo-4,5-dihydro-1H-imidazol-4-yl}phenyl)-2-methoxyacetamide;

(5S)-2-amino-5-[4-(difluoromethoxy)phenyl]-3-methyl-5-phenyl-3,5-dihydro-4H-imidazol-4-one;

2-amino-5-[4-(difluoromethoxy)phenyl]-5-[3-(4-hydroxybut-1-yn-1-yl)phenyl]-3-methyl-3,5-dihydro-4H-imidazol-4-one;

2-amino-5-[4-(difluoromethoxy)phenyl]-5-[3-(4-hydroxybutyl)phenyl]-3-methyl-3,5-dihydro-4H-imidazol-4-one;

2-amino-5-[4-(difluoromethoxy)phenyl]-5-[3-(5-fluoropentyl)phenyl]-3-methyl-3,5-dihydro-4H-imidazol-4-one;

2-amino-5-[4-(difluoromethoxy)phenyl]-5-[3-(4-fluorobutyl)phenyl]-3-methyl-3,5-dihydro-4H-imidazol-4-one;

2-amino-5-[4-(difluoromethoxy)phenyl]-5-[3-(6-fluorohexyl)phenyl]-3-methyl-3,5-dihydro-4H-imidazol-4-one;

2-amino-5-[4-(difluoromethoxy)phenyl]-5-[3-(4-methoxybutyl)phenyl]-3-methyl-3,5-dihydro-4H-imidazol-4-one;

2-amino-5-[4-(difluoromethoxy)phenyl]-5-{3-[(1Z)-3-methoxyprop-1-en-1-yl]phenyl}-3-methyl-3,5-dihydro-4H-imidazol-4-one;

2-amino-5-[4-(difluoromethoxy)phenyl]-5-[3-(3-methoxypropyl)phenyl]-3-methyl-3,5-dihydro-4H-imidazol-4-one;

2-amino-5-[3-(4,4-difluorobutyl)phenyl]-5-[4-(difluoromethoxy)phenyl]-3-methyl-3,5-dihydro-4H-imidazol-4-one;

3-{2-amino-4-[4-(difluoromethoxy)phenyl]-1-methyl-5-oxo-4,5-dihydro-1H-imidazol-4-yl}-N-propylbenzamide;

(1E)-3-chloroprop-1-enyl 2,5-dichlorophenyl sulfone;

2-amino-5-[4-(difluoromethoxy)phenyl]-5-{3-[(2-fluoroethoxy)methyl]phenyl}-3-methyl-3,5-dihydro-4H-imidazol-4-one;

2-amino-5-[4-(difluoromethoxy)phenyl]-3-methyl-5-{3-[(3,3,3-trifluoropropoxy)methyl]phenyl}-3,5-dihydro-4H-imidazol-4-one;

2-amino-5-[4-(difluoromethoxy)phenyl]-5-[3-(methoxymethyl)phenyl]-3-methyl-3,5-dihydro-4H-imidazol-4-one;

2-amino-5-[3-(butoxymethyl)phenyl]-5-[4-(difluoromethoxy)phenyl]-3-methyl-3,5-dihydro-4H-imidazol-4-one;

2-amino-5-{3-[(cyclopropylmethoxy)methyl]phenyl}-5-[4-(difluoromethoxy)phenyl]-3-methyl-3,5-dihydro-4H-imidazol-4-one;

2-amino-5-[4-(difluoromethoxy)phenyl]-5-[3-(ethoxymethyl)phenyl]-3-methyl-3,5-dihydro-4H-imidazol-4-one;

2-amino-5-[4-(difluoromethoxy)phenyl]-3-methyl-5-[3-(propoxymethyl)phenyl]-3,5-dihydro-4H-imidazol-4-one;

2-amino-5-[4-(difluoromethoxy)phenyl]-5-(3-{[2-fluoro-1-(fluoromethyl)ethoxy]methyl}phenyl)-3-methyl-3,5-dihydro-4H-imidazol-4-one;

2-amino-5-[4-(difluoromethoxy)phenyl]-3-methyl-5-{3-[(2,2,2-trifluoroethoxy)methyl]phenyl}-3,5-dihydro-4H-imidazol-4-one;

2-amino-5-[4-(difluoromethoxy)phenyl]-3-methyl-5-{3-[(2,2,3,3-tetrafluoropropoxy)methyl]phenyl}-3,5-dihydro-4H-imidazol-4-one;

4-[4-(difluoromethoxy)phenyl]-4-[3-(3-methoxyprop-1-yn-1-yl)phenyl]-1-methyl-4,5-dihydro-1H-imidazol-2-amine;

2-amino-5-[3-(1,4-difluorobutyl)phenyl]-5-[4-(difluoromethoxy)phenyl]-3-methyl-3,5-dihydro-4H-imidazol-4-one;

2-amino-5-[4-(difluoromethoxy)phenyl]-5-[3-(3-fluorobut-3-en-1-yl)phenyl]-3-methyl-3,5-dihydro-4H-imidazol-4-one;

2-amino-5-[3-(4,4-difluorobut-3-en-1-yl)phenyl]-5-[4-(difluoromethoxy)phenyl]-3-methyl-3,5-dihydro-4H-imidazol-4-one;

2-amino-5-[4-(difluoromethoxy)phenyl]-3-methyl-5-[3-(4,4,4-trifluorobutyl)phenyl]-3,5-dihydro-4H-imidazol-4-one;

5-(3-{2-amino-4-[4-(difluoromethoxy)phenyl]-1-methyl-5-oxo-4,5-dihydro-1H-imidazol-4-yl}phenyl)pentanenitrile;

4-(3-{2-amino-4-[4-(difluoromethoxy)phenyl]-1-methyl-5-oxo-4,5-dihydro-1H-imidazol-4-yl}phenyl)butanenitrile;

2-amino-5-{3-[(1E)-4,4-difluorobut-1-en-1-yl]phenyl}-5-[4-(difluoromethoxy)phenyl]-3-methyl-3,5-dihydro-4H-imidazol-4-one;

2-amino-5-[4-(difluoromethoxy)phenyl]-5-[3-(3-hydroxyhex4-yn-1-yl)phenyl]-3-methyl-3,5-dihydro-4H-imidazol-4-one;

2-amino-5-[4-(difluoromethoxy)phenyl]-5-{3-[(1E)-6-methoxyhex-1-en-1-yl]phenyl}-3-methyl-3,5-dihydro-4H-imidazol-4-one;

2-amino-5-[4-(difluoromethoxy)phenyl]-5-{3-[(1E)-5-methoxypent-1-en-1-yl]phenyl}-3-methyl-3,5-dihydro-4H-imidazol-4-one;

2-amino-5-[4-(difluoromethoxy)phenyl]-5-{3-[2-(methoxymethyl)cyclopropyl]phenyl}-3-methyl-3,5-dihydro-4H-imidazol-4-one;

2-amino-5-[4-(difluoromethoxy)phenyl]-5-{3-[(1E)-5-hydroxypent-1-en-1-yl]phenyl}-3-methyl-3,5-dihydro-4H-imidazol-4-one;

2-amino-5-[4-(difluoromethoxy)phenyl]-5-{3-[(1E)-3-methoxyprop-1-en-1-yl]phenyl}-3-methyl-3,5-dihydro-4H-imidazol-4-one;

2-amino-5-[4-(difluoromethoxy)phenyl]-5-{3-[(1E)-4-methoxybut-1-en-1-yl]phenyl}-3-methyl-3,5-dihydro-4H-imidazol-4-one;

2-amino-5-[4-(difluoromethoxy)phenyl]-5-{3-[(1E)-4-hydroxybut-1-en-1-yl]phenyl}-3-methyl-3,5-dihydro-4H-imidazol-4-one;

2-amino-5-[4-(difluoromethoxy)phenyl]-5-{3-[2-(2-methoxyethyl)cyclopropyl]phenyl}-3-methyl-3,5-dihydro-4H-imidazol-4-one;

2-amino-5-[4-(difluoromethoxy)phenyl]-5-{3-[(1E)-4-fluorobut-1-en-1-yl]phenyl}-3-methyl-3,5-dihydro-4H-imidazol-4-one;

2-amino-5-[4-(difluoromethoxy)phenyl]-5-{3-[(1E)-5-fluoropent-1-en-1-yl]phenyl}-3-methyl-3,5-dihydro-4H-imidazol-4-one;

5-(3-acetylphenyl)-2-amino-5-[4-(difluoromethoxy)phenyl]-3-methyl-3,5-dihydro-4H-imidazol-4-one;

2-amino-5-[4-(difluoromethoxy)phenyl]-5-{4-fluoro-3-[(1E)-4-fluorobut-1-en-1-yl]phenyl}-3-methyl-3,5-dihydro-4H-imidazol-4-one;

2-amino-5-[4-(difluoromethoxy)phenyl]-5-[3-(3-fluoroprop-1-yn-1-yl)phenyl]-3-methyl-3,5-dihydro-4H-imidazol-4-one;

2-amino-5-[4-(difluoromethoxy)phenyl]-5-(3-hydroxyphenyl)-3-methyl-3,5-dihydro-4H-imidazol-4-one;

2-amino-5-[4-(difluoromethoxy)phenyl]-5-[3-(3-fluoropropoxy)phenyl]-3-methyl-3,5-dihydro-4H-imidazol-4-one;

2-amino-5-[3-(cyclopropylmethoxy)phenyl]-5-[4-(difluoromethoxy)phenyl]-3-methyl-3,5-dihydro-4H-imidazol-4-one;

2-amino-5-[4-(difluoromethoxy)phenyl]-3-methyl-5-[3-(4,4,4-trifluorobutoxy)phenyl]-3,5-dihydro-4H-imidazol-4-one;

2-amino-5-[3-(2,2-difluoroethoxy)phenyl]-5-[4-(difluoromethoxy)phenyl]-3-methyl-3,5-dihydro-4H-imidazol-4-one;

2-amino-5-[4-(difluoromethoxy)phenyl]-5-[3-(4-fluorobutoxy)phenyl]-3-methyl-3,5-dihydro-4H-imidazol-4-one;

2-amino-5-[4-(difluoromethoxy)phenyl]-3-methyl-5-[3-(3-phenoxypropoxy)phenyl]-3,5-dihydro-4H-imidazol-4-one;

4-(3-{2-amino-4-[4-(difluoromethoxy)phenyl]-1-methyl-5-oxo-4,5-dihydro-1H-imidazol-4-yl}phenoxy)butanenitrile;

2-amino-5-[4-(difluoromethoxy)phenyl]-5-[4-fluoro-3-(3-fluoropropoxy)phenyl]-3-methyl-3,5-dihydro-4H-imidazol-4-one;

2-amino-5-[3-(but-2-yn-1-yloxy)-4-fluorophenyl]-5-[4-(difluoromethoxy)phenyl]-3-methyl-3,5-dihydro-4H-imidazol-4-one;

2-amino-5-[4-(difluoromethoxy)phenyl]-5-[4-fluoro-3-(4-fluorobutoxy)phenyl]-3-methyl-3,5-dihydro-4H-imidazol-4-one;

2-amino-5-[3-(2,2-difluoroethoxy)-4-fluorophenyl]-5-[4-(difluoromethoxy)phenyl]-3-methyl-3,5-dihydro-4H-imidazol-4-one;

(5R)-2-amino-5-[4-(difluoromethoxy)phenyl]-5-[4-fluoro-3-(3-fluoropropoxy)phenyl]-3-methyl-3,5-dihydro-4H-imidazol-4-one;

(5S)-2-amino-5-[4-(difluoromethoxy)phenyl]-5-[4-fluoro-3-(3-fluoropropoxy)phenyl]-3-methyl-3,5-dihydro-4H-imidazol-4-one;

2-amino-5-{3-[(4,4-difluorobut-3-en-1-yl)oxy]phenyl}-5-[4-(difluoromethoxy)phenyl]-3-methyl-3,5-dihydro-4H-imidazol-4-one;

(5S)-2-amino-5-[3-(2,2-difluoroethoxy)-4-fluorophenyl]-5-[4-(difluoromethoxy)phenyl]-3-methyl-3,5-dihydro-4H-imidazol-4-one;

(5R)-2-amino-5-[3-(2,2-difluoromethoxy)-4-fluorophenyl]-5-[4-(difluoromethoxy)phenyl]-3-methyl-3,5-dihydro-4H-imidazol-4-one;

2-amino-5-[4-(difluoromethoxy)phenyl]-5-[3-(2-fluoroethyl)phenyl]-3-methyl-3,5-dihydro-4H-imidazol-one;

2-amino-5-[4-(difluoromethoxy)phenyl]-5-[3-(5-fluoropentanoyl)phenyl]-3-methyl-3,5-dihydro-4H-imidazol-4-one;

2-amino-5-[4-(difluoromethoxy)phenyl]-5-[3-(4-fluorobutanoyl)phenyl]-3-methyl-3,5-dihydro-4H-imidazol-4-one;

2-amino-5-[3-(but-3-en-1-yloxy)phenyl]-5-[4-(difluoromethoxy)phenyl]-3-methyl-3,5-dihydro-4H-imidazol-4-one;

2-amino-5-[3-(but-3-en-1-yloxy)-4-fluorophenyl]-5-[4-(difluoromethoxy)phenyl]-3-methyl-3,5-dihydro-4H-imidazol-4-one;

(5R)-2-amino-5-[3-(but-3-en-1-yloxy)phenyl]-5-[4-(difluoromethoxy)phenyl]-3-methyl-3,5-dihydro-4H-imidazol-4-one;

(5S)-2-amino-5-[3-(but-3-en-1-yloxy)phenyl]-5-[4-(difluoromethoxy)phenyl]-3-methyl-3,5-dihydro-4H-imidazol-4-one;

2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one;

2-amino-5-[4-(difluoromethoxy)phenyl]-5-(4-fluoro-3-pent-4-en-1-ylphenyl)-3-methyl-3,5-dihydro-4H-imidazol-4-one;

2-amino-5-(3-but-3-en-1-yl-4-fluorophenyl)-5-[4-(difluoromethoxy)phenyl]-3-methyl-3,5-dihydro-4H-imidazol-4-one;

3-{2-amino-4-[4-(difluoromethoxy)phenyl]-1-methyl-5-oxo-4,5-dihydro-1H-imidazol-4-yl}benzaldehyde;

2-amino-5-[4-(difluoromethoxy)phenyl]-5-[3-(1-hydroxybut-2-yn-1-yl)phenyl]-3-methyl-3,5-dihydro-4H-imidazol-4-one;

2-amino-5-[4-(difluoromethoxy)phenyl]-5-[3-(1,4-dihydroxybut-2-yn-1-yl)phenyl]-3-methyl-3,5-dihydro-4H-imidazol-4-one;

(5R)-2-amino-5-[3-(difluoromethoxy)phenyl]-5-[4-(difluoromethoxy)phenyl]-3-methyl-3,5-dihydro-4H-imidazol-4-one;

2-amino-5-[4-(difluoromethoxy)phenyl]-5-[3-(2,2-dimethyl-3-oxocyclobutyl)phenyl]-3-methyl-3,5-dihydro-4H-imidazol-4-one;

2-amino-5-[4-(difluoromethoxy)phenyl]-3-methyl-5-[3-(3-oxocyclobutyl)phenyl]-3,5-dihydro-4H-imidazol-4-one;

2-amino-5-[4-(difluoromethoxy)phenyl]-5-[3-(3-hydroxycyclobutyl)phenyl]-3-methyl-3,5-dihydro-4H-imidazol-4-one;

methyl [3-(3-{2-amino-4-[4-(difluoromethoxy)phenyl]-1-methyl-5-oxo-4,5-dihydro-1H-imidazol-4-yl}phenyl)cyclobutyl]acetate;

methyl (3-(3-{2-amino-4-[4-(difluoromethoxy)phenyl]-1-methyl-5-oxo-4,5-dihydro-1H-imidazol-4-yl}phenyl)cyclobutylidene]acetate;

or a tautomer thereof, a stereoisomer thereof or a pharmaceutically acceptable salt thereof.

More preferred compounds of the invention include:

(5S)-2-amino-5-[4-(difluoromethoxy)phenyl]-3-methyl-5-phenyl-3,5-dihydro-4H-imidazol-4-one;

(5R)-2-amino-5-[4-(difluoromethoxy)phenyl]-3-methyl-5-(3-pent-4-en-1-ylphenyl)-3,5-dihydro-4H-imidazol-4-one;

(5R)-2-amino-5-[4-(difluoromethoxy)phenyl]-3-methyl-5-(3-prop-1-yn-1-ylphenyl)-3,5-dihydro-4H-imidazol-4-one;

(5R)-2-amino-5-[4-(difluoromethoxy)phenyl]-3-methyl-5-(3-pent-1-yn-1-ylphenyl)-3,5-dihydro-4H-imidazol-4-one;

(5R)-2-amino-5-[4-(difluoromethoxy)phenyl]-3-methyl-5-[3-(3-methylbut-1-yn-1-yl)phenyl]-3,5-dihydro-4H-imidazol-4-one;

(5R)-2-amino-5-[4-(difluoromethoxy)phenyl]-5-[3-(3-methoxyprop-1-yn-1-yl)phenyl]-3-methyl-3,5-dihydro-4H-imidazol-4-one;

(5R)-2-amino-5-[4-(difluoromethoxy)phenyl]-5-[3-(4-methoxybut-1-yn-1-yl)phenyl]-3-methyl-3,5-dihydro-4H-imidazol-4-one;

(5R)-2-amino-5-[4-(difluoromethoxy)phenyl]-5-[3-(5-fluoropent-1-yn-1-yl)phenyl]-3-methyl-3,5-dihydro-4H-imidazol-4-one;

(5R)-2-amino-5-[4-(difluoromethoxy)phenyl]-5-{3-[(3S)-3-hydroxybut-1-yn-1-yl]phenyl}-3-methyl-3,5-dihydro-4H-imidazol-4-one;

(5R)-2-amino-5-[4-(difluoromethoxy)phenyl]-5-[4-fluoro-3-(3-methoxyprop-1-yn-1-yl)phenyl]-3-methyl-3,5-dihydro-4H-imidazol-4-one;

(5R)-2-amino-5-[4-(difluoromethoxy)phenyl]-5-[4-fluoro-3-(4-methoxybut-1-yn-1-yl)phenyl]-3-methyl-3,5-dihydro-4H-imidazol-4-one;

(5R)-2-amino-5-[4-(difluoromethoxy)phenyl]-5-[4-fluoro-3-(3-fluoropropoxy)phenyl]-3-methyl-3,5-dihydro-4H-imidazol-4-one;

(5R)-2-amino-5-[3-(2,2-difluoroethoxy)-4-fluorophenyl]-5-[4-(difluoromethoxy)phenyl]-3-methyl-3,5-dihydro-4H-imidazol-4-one;

(5R)-2-amino-5-{3-[(4,4-difluorobut-3-en-1-yl)oxy]phenyl}-5-[4-(difluoromethoxy)phenyl]-3-methyl-3,5-dihydro-4H-imidazol-4-one;

or a tautomer thereof, a stereoisomer thereof or a pharmaceutically acceptable salt thereof.

Compounds of formula I may be prepared using conventional synthetic methods and, if required, standard separation or isolation techniques. For example, compounds of formula I may be prepared by reacting a diketone of formula II with an aminoguanidine derivative of formula III in the presence of a base such as a metal carbonate to give the desired formula I compound. The reaction is shown below in flow diagram I.

Flow Diagram I

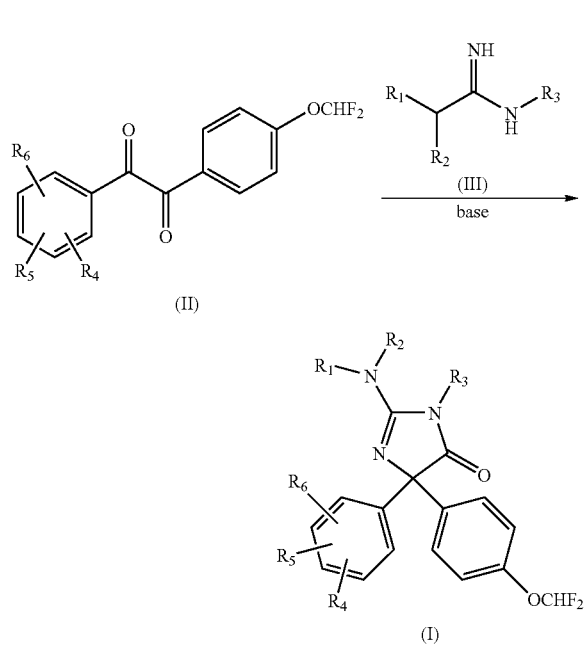

Diketone compounds of formula II may be prepared by reacting an alkyne of formula IV with an oxidizing agent such as Pd(II)Cl$_2$/DMSO, N-bromosuccinimide/DMSO, ozone, sodium periodate with ruthenium (IV) oxide hydrate, sulfur trioxide, KMnO$_4$, I$_2$/DMSO, or combinations thereof, preferable KMnO$_4$ and I$_2$/DMSO. The reaction is shown in flow diagram II.

Flow Diagram II

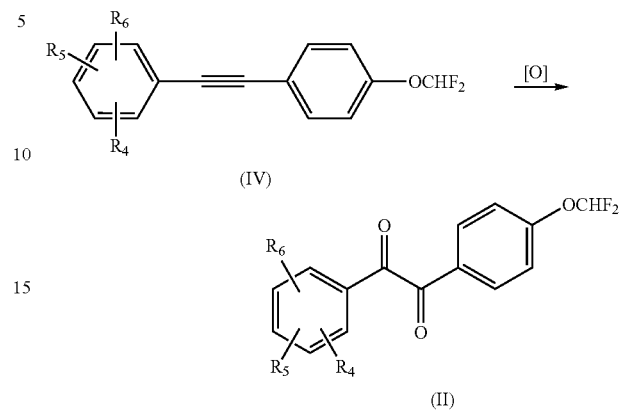

Alkyne compounds of formula IV may be prepared by reacting an ethynylbenzene compound of formula V with 4-(difluoromethoxy)-1-iodobenzene in the presence of a Pd catalyst, such as dichlorobis(triphenylphosphine)palladium (II), and CuI to give the desired phenylethynylbenzene compound of formula IV. The reaction is shown in flow diagram III.

Flow Diagram III

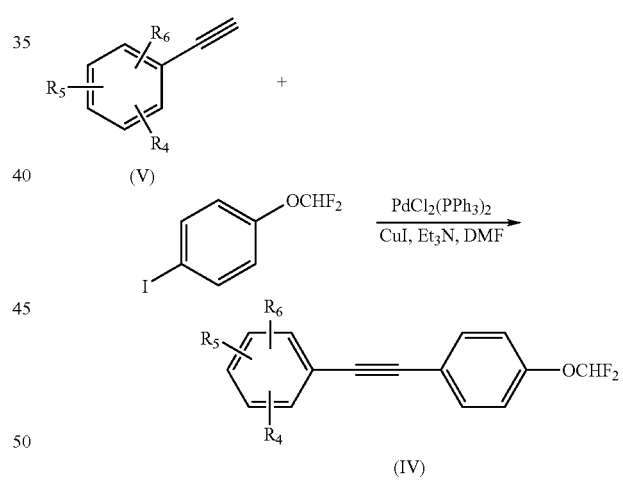

Advantageously, the compounds of formula I act as BACE inhibitors for the treatment of β-amyloid deposits and neurofibrillary tangles associated with such diseases as Alzheimer's disease, Trisomy 21 (Down's Syndrome), Hereditary Cerebral Hemorrhage with Amyloidosis of the Dutch-type (HCHWA-D), and other neurodegenerative disorders. Accordingly, the present invention provides methods for modulating BACE and treating, preventing, or ameliorating β-amyloid deposits and neurofibrillary tangles associated with diseases and disorders such as Alzheimer's disease, Trisomy 21 (Down's Syndrome), Hereditary Cerebral Hemorrhage with Amyloidosis of the Dutch-type (HCHWA-D), or other neurodegenerative disorders. Such methods include providing a patient suffering from or being susceptible to a disease or injury associated with excessive BACE activity an effective amount of a compound of formula I. Also according to the present invention there is provided a method of treating Alzheimer's disease and related senile dementia's in humans or other mammals which comprises administering to a human or other mammal an effective amount of a compound of the present invention.

The present invention also provides a method for the treatment of a disorder related to or associated with excessive BACE activity in a patient in need thereof which comprises providing said patient a therapeutically effective amount of at least one compound of formula I. Representative disorders include Alzheimer's disease, cognitive impairment, Down's Syndrome, HCHWA-D, cognitive decline, senile dementia, cerebral amyloid angiopathy, degenerative dementia, or other neurodegenerative disorders. Certain of these diseases are characterized by production of β-amyloid deposits or neurofibrillary tangles.

The present invention also provides a method for inhibiting the activity of BACE, comprising administering to a patient or contacting a receptor thereof with an effective amount of at least one compound of formula I. Certain methods further comprise determining BACE activity, either before or after said contacting step.

The present invention also provides a method of ameliorating β-amyloid deposits or neurofibrillary tangles in a mammal which comprises providing said mammal an effective amount of at least one compound of formula I.

Also provided are methods of ameliorating symptoms of Alzheimer's disease, cognitive impairment, Down's Syndrome, HCHWA-D, cognitive decline, senile dementia, cerebral amyloid angiopathy, degenerative dementia, or other neurodegenerative disorders in a mammal which comprises providing said mammal an effective amount of at least one compound of formula I.

Further methods prevent Alzheimer's disease, cognitive impairment, Down's Syndrome, HCHWA-D, cognitive decline, senile dementia, cerebral amyloid angiopathy, degenerative dementia, or other neurodegenerative disorders in a mammal that is known to suffer from or suspected to be at risk of suffering from such diseases. These methods comprise providing said mammal an effective amount of at least one compound of formula I.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The term "patient", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The terms "effective amount", "therapeutically effective amount" and "effective dosage" as used herein, refer to the amount of a compound that, when administered to a patient, is effective to at least partially ameliorate (and, in preferred embodiments, cure) a condition from which the patient is suspected to suffer.

It is understood that the effective dosage of the active compounds of this invention may vary depending upon the particular compound utilized, the mode of administration, the condition, and severity thereof, of the condition being treated, as well as the various physical factors related to the individual being treated. For treating Alzheimer's disease and other related senile dementia's, generally, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg preferably from about 3.5 to about 5 mg. In the case of a 70 kg human adult, the total daily dose will generally be from about 7 mg to about 70 mg and may be adjusted to provide the optimal therapeutic result. This regimen may be adjusted to provide the optimal therapeutic response.

In one aspect, the present invention is directed to compositions comprising one or more compounds of formula I and one or more pharmaceutically acceptable carriers.

The present invention also comprises pharmaceutical compositions comprising compounds of the above-described formula I and a pharmaceutically acceptable carrier.

The term "carrier", as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, thransdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

For a more clear understanding, and in order to illustrate the invention more clearly, specific examples thereof are set forth hereinbelow. The following examples are merely illustrative and are not to be understood as limiting the scope and underlying principles of the invention in any way.

Unless otherwise stated, all parts are parts by weight. The terms TEA, DMSO and DMF designate triethyl amine, dimethyl sulfoxide and N,N-dimethylformamide, respectively. The terms EtOAc and THF designate ethyl acetate and tetrahydrofuran, respectively. The term NMR designates proton nuclear magnetic resonance and the term MS designates mass spectroscopy with (+) referring to the positive mode which generally gives a M+1 (or M+H) absorption where M=the molecular mass. All compounds are analyzed at least by MS and NMR.

In the chemical drawings, the term Ph represents phenyl.

Proton nuclear magnetic resonance spectra were obtained on a Bruker AVANCE 300 spectrometer at 300 MHz or VARIAN 400 spectrometer at 400 MHz. Spectra are given in ppm (δ) and coupling constants, J values, are reported in Hertz. Tetramethylsilane was used as an internal reference standard. Mass spectra were obtained on a Perkin Elmer Sciex 100.

EXAMPLE 1

Preparation of (5S)-2-Amino-5-[4-(difluoromethoxy) phenyl]-3-methyl-5-phenyl-3,5-dihydro-4H-imidazol-4-one [A] and (5R)-2-Amino-5-[4-(difluoromethoxy)-phenyl]-3-methyl-5-phenyl-3,5-dihydro-4H-imidazol-4-one [B]

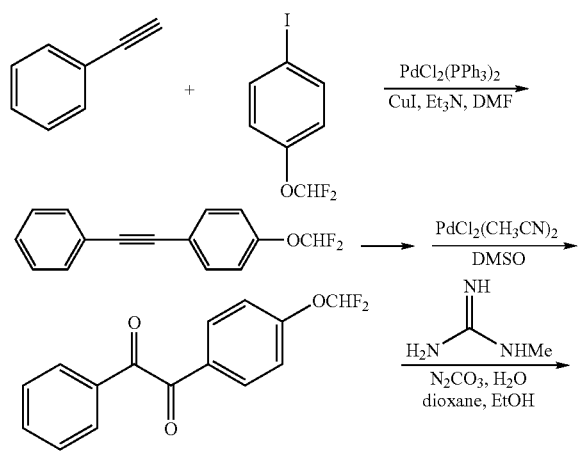

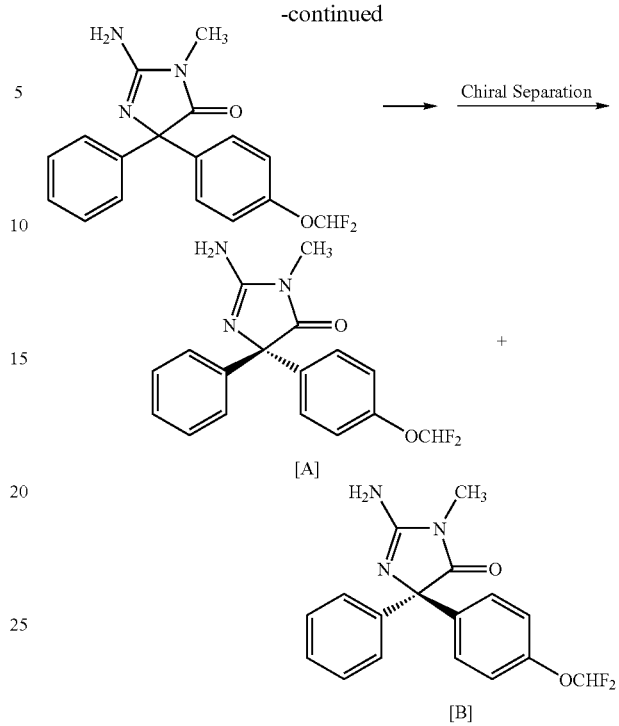

Step a)
1-(Difluoromethoxy)-4-(phenylethynyl)benzene

Into a mixture of ethynylbenzene (1.9 g, 18.5 mmol), 1-(difluoromethoxy)-4-iodobenzene (5 g, 18.5 mmol), N,N-dimethylformamide (35 mL), and triethylamine (12.8 mL, 92.6 mmol) was introduced anhydrous argon for 5 minutes. Then, copper(I) iodide (1.85 mmol, 351 mg) and dichlorobis(triphenylphosphine)palladium(II) (1.11, 0.71 g) were added into the mixture and the new mixture was stirred at 60° C. for 3 hours. The mixture cooled to room temperature, poured into water and extracted with ethyl ether. The organic extracts were dried over MgSO$_4$. Evaporation and purification on silica gel (ISCO) using hexanes/EtOAc (100/1) as the eluting solvent, gave 1-(difluoromethoxy)-4-(phenylethynyl)benzene as a clear oil (3.45 g, 76% yield). MS m/e M$^+$ 244; $^1$H NMR (400 MHz, DMSO-d$_6$) δ7.2 (d, J=8.78 Hz, 2H), 7.28-7.45 (m, 4H), 7.5-7.55 (m, 2H), 7.6 (d, J=7.78 Hz, 2H).

Step b) 1-[4-(Difluoromethoxy)phenyl]-2-phenylethane-1,2-dione

Into a mixture of 1-(difluoromethoxy)-4-(phenylethynyl) benzene (2.85 g, 11.68 mmol) and dimethylsulfoxide (40 mL) was introduced anhydrous argon gas for 5 minutes. Then, bis(acetonitrile)dichloropalladium(II) (1.16, 0.3 g) was added into the mixture and the new mixture was stirred at 145° C. for 20 hours. The mixture cooled to room temperature, poured into water and extracted with EtOAc. The organic extracts were dried over MgSO$_4$. Evaporation and purification on silica gel (ISCO) using hexanes/EtOAc (30/1) as the eluting solvent gave 1-[4-(difluoromethoxy)phenyl]-2-phenylethane-1,2-dione as a clear oil (2.92 g, 91% yield). MS m/e M$^+$ 276; $^1$H NMR (400 MHz, DMSO-d$_6$) δ7.2 (d, J=8.78 Hz, 2H), 7.6 (m, 3H), 7.75 (t J=8.54 Hz, 1H), 7.88 (d, J=8.54 Hz, 2H), 7.98 (d, J=8.78 Hz, 2H).

Step c) 2-Amino-5-[4-(difluoromethoxy)phenyl]-3-methyl-5-phenyl-3,5-dihydro-4H-imidazol-4-one Into a mixture of 1-[4-(difluoromethoxy)phenyl]-2-phenylethane-1,2-dione (3.7 g, 13.4 mmol), dioxane (180 mL) and EtOH (240 mL) were added 1-methylguanidine hydrochloride (6.6 g, 60.3 mmol), and a solution of Na$_2$CO$_3$ (6.4 g, 60.3 mmol) in H$_2$O (20 mL). The new mixture was stirred at 95° C. for 3 hours. Then, the volatiles were removed under vacuum and the residue was taken in water and extracted with EtOAc. The organic extracts were dried over MgSO$_4$. Evaporation and purification on silica gel (ISCO) using MeOH/EtOAc (1/20) as the eluting solvent gave 2-amino-5-[4-(difluoromethoxy)phenyl]-3-methyl-5-phenyl-3,5-dihydro-4H-imidazol-4-one as a white solid (3.65 g, 94% yield). MS m/e (M+H)$^+$ 332; $^1$H NMR (400 MHz, DMSO-d$_6$) δ2.93 (s, 3H), 6.61 (brs, 2H), 7.1 (d, J=8.54 Hz, 2H), 7.15-7.31 (m, 4H), 7.38 (m, 2H), 7.42 (d, J=8.54 Hz, 2H).

Step d) (5S)-2-Amino-5-[4-(difluoromethoxy)phenyl]-3-methyl-5-phenyl-3,5-dihydro-4H-imidazol-4-one [A] and (5R)-2-Amino-5-[4-(difluoromethoxy)phenyl]-3-methyl-5-phenyl-3,5-dihydro-4H-imidazol-4-one [B]

A racemic mixture of 2-amino-5-[4-(difluoromethoxy)phenyl]-3-methyl-5-phenyl-3,5-dihydro-4H-imidazol-4-one was separated by chiral chromatography technique (Chiralcel OJ, 0.46×10 cm, using 15% ethanol in 85% hexane and diethylamine as the mobile phase) to produce the two enantiomers as white solids; [A] (5S)-2-amino-5-[4-(difluoromethoxy)phenyl]-3-methyl-5-phenyl-3,5-dihydro-4H-imidazol-4-one, MS m/e (M+H)$^+$ 332; $^1$H NMR (400 MHz, DMSO-d$_6$) δ2.93 (s, 3H), 6.61 (brs, 2H), 7.1 (d, J=8.54 Hz, 2H), 7.15-7.31 (m, 4H), 7.38 (m, 2H), 7.42 (d, J=8.54 Hz, 2H); [α]$_{25}$=+20 (C=1% in MeOH), and [B] (5R)-2-amino-5-[4-(difluoromethoxy)phenyl]-3-methyl-5-phenyl-3,5-dihydro-4H-imidazol-4-one, MS m/e (M+H)$^+$ 332; $^1$H NMR (400 MHz, DMSO-d$_6$) δ2.93 (s, 3H), 6.61 (brs, 2H), 7.1 (d, J=8.54 Hz, 2H), 7.15-7.31 (m, 4H), 7.38 (m, 2H), 7.42 (d, J=8.54 Hz, 2H); [α]$_{25}$=−22 (C=1% in MeOH).

EXAMPLE 2

Preparation of (5R)-2-amino-5-(3-bromophenyl)-5-[4-(difluoromethoxy)phenyl]-3-methyl-3,5-dihydro-4H-imidazol-4-one

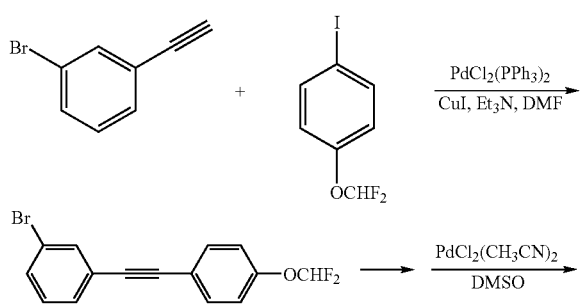

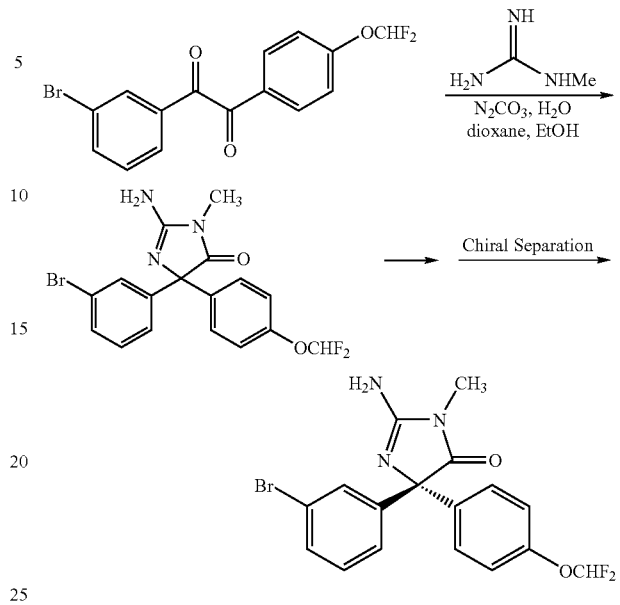

Using essentially the same procedure described in Example 1, steps a-d, and employing 1-bromo-3-ethynylbenzene in step a, the racemic mixture of 2-amino-5-(3-bromophenyl)-5-[4-(difluoromethoxy)phenyl]-3-methyl-3,5-dihydro-4H-imidazol-4-one was obtained and separated by chiral chromatography technique (Chiralcel OJ, 2×25 cm, using 5% ethanol in 95% hexane and diethylamine as the mobile phase) to give the title enantiomer, MS m/e (M+H)$^+$ 332; $^1$H NMR (400 MHz, DMSO-d$_6$) δ2.94 (s, 3H), 6.72 (brs, 2H), 7.1 (d, J=8.66 Hz, 2H), 7.13-7.35 (m, 2H), 7.38-7.43 (m, 4H), 7.56 (t, J=1.72 Hz, 1H); [α]$_{25}$=−4 (C=1% in MeOH).

EXAMPLE 3

Preparation of (5R)-2-Amino-5-(3-bromo-4-fluorophenyl)-5-[4-(difluoromethoxy)phenyl]-3-methyl-3,5-dihydro-4H-imidazol-4-one

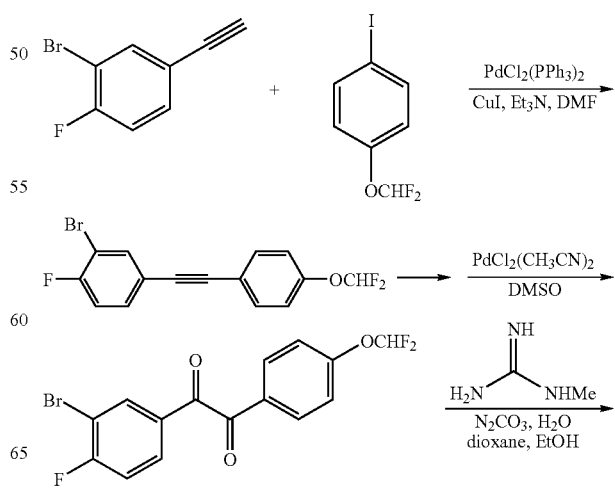

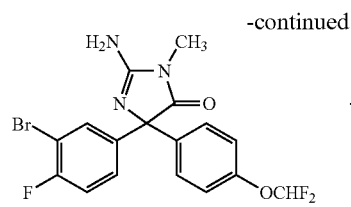

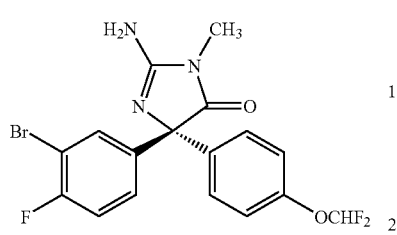

Using essentially the same procedure described in Example 1, steps a-c, and employing 3-bromo-4-fluoro-1-ethynylbenzene the racemic mixture of 2-amino-5-(3-bromo-4-fluorophenyl)-5-[4-(difluoromethoxy)phenyl]-3-methyl-3,5-dihydro-4H-imidazol-4-one was obtained and separated by chiral chromatography technique (Chiralcel OJ, 0.46×10 cm, using 15% ethanol in 85% hexane and diethylamine as the mobile phase) to give the title enantiomer, MS m/e (M+H)+ 332; $^1$H NMR (400 MHz, DMSO-d$_6$) δ2.94 (s, 3H), 6.74 (brs, 2H), 7.1 (d, J=8.75 Hz, 2H), 7.13-7.65 (m, 5H), 7.67 (d, J=2.2 Hz, 1H); [a]$_{25}$=−22 (C=1% in MeOH).

EXAMPLE 4

Preparation of (5R)-2-Amino-5-[4-(difluoromethoxy)phenyl]-3-methyl-5-(3-propylphenyl)-3,5-dihydro-4H-imidazol-4-one [A] and (5S)-2-Amino-5-[4-(difluoromethoxy)phenyl]-3-methyl-5-(3-propylphenyl)-3,5-dihydro-4H-imidazol-4-one [B]

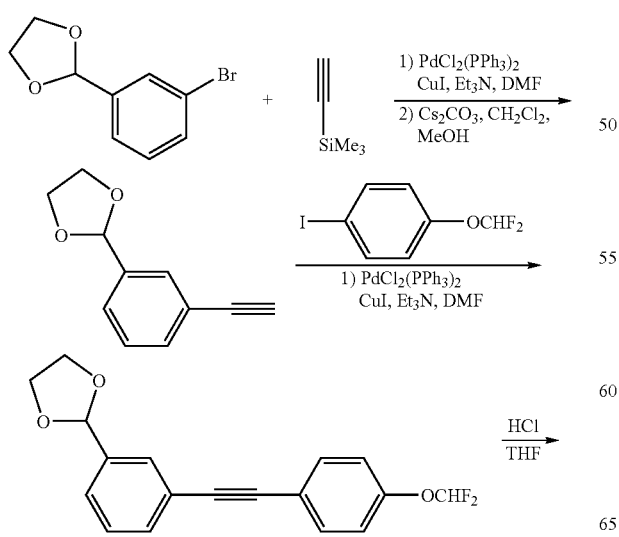

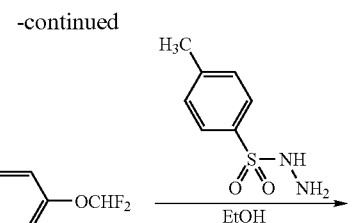

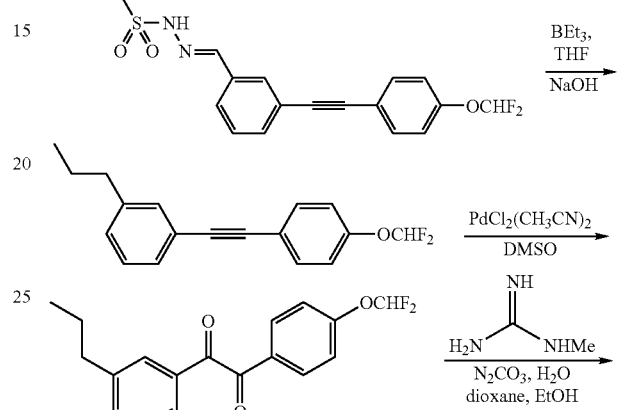

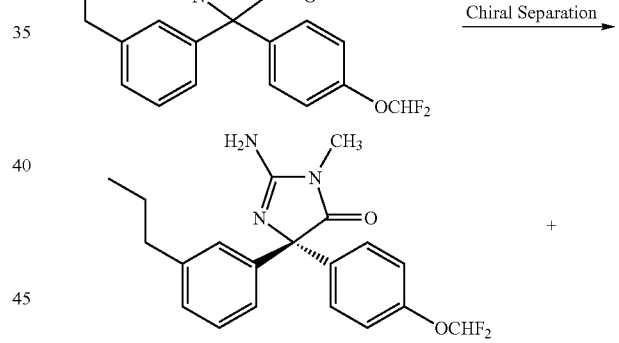

Step a) 2-(3-Ethynylphenyl)-1,3-dioxolane

A mixture of ethynyl(trimethyl)silane (36 g, 367 mmol), 2-(3-bromophenyl)-1,3-dioxolane (78 g, 342 mmol), N,N-dimethylformamide (400 mL), and triethylamine (1.1 81 mL, mmol) was bubbled with anhydrous argon for 5 minutes, treated with copper iodide (0.94 g, 4.96 mmol) and dichlorobis(triphenylphosphine) palladium(II) (7.7 g, 11.01 mmol), stirred at 60° C. for 3 hours, cooled to room temperature, poured into water and extracted with ethyl ether. The organic extracts were combined, dried over MgSO$_4$ and concentrated in vacuo to give {[3-(1,3-dioxolan-2-yl)phenyl]ethynyl}-(trimethyl)silane as a yellow oil (63 g, 256 mmol). The yellow oil was dissolved in MeOH (600 mL) and CH$_2$Cl$_2$ (600 mL), treated with cesium carbonate (91.8 g, 281.6 mmol), stirred at room temperature for 10 h, poured into water and extracted with ethyl ether. The ether extracts were combined, dried over MgSO$_4$, concentrated in vacuo and distilled to give 2-(3-ethynylphenyl)-1,3-dioxolane as a yellow oil (42 g, 71% yield), MS m/e M$^+$ 174; $^1$H NMR (400 MHz, DMSO-d$_6$) δ3.9-4.05 (m, 4H), 4.15 (s, 1H), 5.7 (s, 1H), 7.35-7.45 (m, 4H).

Step b) 2-(3-{[4-(Difluoromethoxy)phenyl]ethynyl}phenyl)-1,3-dioxolane

Using essentially the same procedure described in Example 1, step a, and employing 2-(3-ethynylphenyl)-1,3-dioxolane and 1-(difluoromethoxy)-4-iodobenzene, the coupled product was obtained. This product was purified on silica gel (ISCO) using hexanes/EtOAc 5/1 as the eluting solvents to give 2-(3-{[4-(difluoromethoxy)phenyl]ethynyl}phenyl)-1,3-dioxolane as a yellow oil (7.9 g, 85% yield), MS m/e (M+H)$^+$ 317; $^1$H NMR (400 MHz, DMSO-d$_6$) δ3.9-4.05 (m, 4H), 5.72 (s, 1H), 7.1-7.3 (m, 3H), 7.4 (m, 2H), 7.5-7.6 (m, 4H).

Step c) 3-{[4-(Difluoromethoxy)phenyl]ethynyl}benzaldehyde

Into a mixture of 2-(3-{[4-(difluoromethoxy)phenyl]ethynyl}phenyl)-1,3-dioxolane, (1.0 g, 3.1 mmol) and THF (5 mL) was added HCl (2N, 1 mL). The mixture was stirred at room temperature for 2 hours, poured into water and extracted with EtOAc/ethyl ether 1/1. The organic extracts were dried over MgSO$_4$. Evaporation and purification on silica gel (ISCO) using hexanes/EtOAc (3/1) as the eluting solvents gave 3-{[4-(difluoromethoxy)phenyl]ethynyl}benzaldehyde as a yellow oil (3.65 g, 95% yield), MS m/e M$^+$ 272; $^1$H NMR (400 MHz, DMSO-d$_6$) δ3.9-4.05 (m, 4H), 5.72 (s, 1H), 7.1-7.3 (m, 4H), 7.62 (m, 2H), 7.8-7.9 (m, 2H), 8.03 (s, 1H), 9.99 (s, 1H).

Step d) N'-[(1E)-(3-{[4-(Difluoromethoxy)phenyl]ethynyl}phenyl)methylene]-4-methylbenzenesulfonohydrazide A mixture of 3-{[4-(difluoromethoxy)phenyl]ethynyl}benzaldehyde (3.69 g, 13.57 mmol), 4-methylbenzenesulfonohydrazide (2.9 g, 15.6 mmol) and EtOH (11 mL) was refluxed for 30 minutes. cooled to room temperature, poured into water and extracted with ethyl ether. The organic extracts were combined dried over MgSO$_4$ and concentrated in vacuo. The resultant residue was purified on silica gel (Biotage) using hexanes/EtOAc (2/1) as the eluting solvents to give N'-[(1E)-(3-{[4-(difluoromethoxy)phenyl]ethynyl}phenyl)methylene]-4-methylbenzenesulfonohydrazide as a tan solid (5.4 g, 90% yield), MS m/e (M+H)$^+$ 441; $^1$H NMR (400 MHz, DMSO-d$_6$) δ2.32 (s, 3H), 7.2 (d, J=8.66 Hz, 2H), 7.3-7.6 (m, 8H), 7.72 (d, J=8.3 Hz, 2H), 7.88 (s, 1H), 11.54 (s, 1H).

Step e) 1-{[4-(Difluoromethoxy)phenyl]ethynyl}-3-propylbenzene

A mixture of N'-[(1E)-(3-{[4-(difluoromethoxy)phenyl]ethynyl}phenyl)methylene]-4-methylbenzenesulfonohydrazide (0.67 mg, 1.52 mmol) in THF was treated with triethyl borane (1.0 M in THF, 1.52 mL, 1.52 mmol), stirred for 2 minutes, treated with NaOH (2.5 N, 0.61 mL, 1.52 mmol), refluxed for 2 hours, cooled to room temperature, poured into water and extracted with EtOAc. The organic extracts were combined, dried over MgSO$_4$ and concentrated in vacuo. The resultant residue was purified on silica gel (ISCO) using hexanes/EtOAc (50/1) as the eluting solvents to give 1-{[4-(difluoromethoxy)phenyl]ethynyl}-3-propylbenzene as a clear oil (386 mg, 89% yield), MS m/e (M+H)$^+$ 286; $^1$H NMR (400 MHz, DMSO-d$_6$) δ0.85 (t, J=7.32 Hz, 3H), 1.57 (m, 2H), 2.6 (t, J=7.32 Hz, 2H), 7.2 (m, 3H), 7.35-7.45 (m, 4H), 7.58 (d, J=8.79 Hz, 2H).

Step f) 1-[4-(Difluoromethoxy)phenyl]-2-(3-propylphenyl)ethane-1,2-dione

Using essentially the same procedure described in Example 1, step b, and employing 1-{[4-(difluoromethoxy)phenyl]ethynyl}-3-propylbenzene, the dione product was obtained. This product was purified on silica gel (ISCO) using hexanes/EtOAc 30/1 as the eluting solvents to give 1-[4-(difluoromethoxy)phenyl]-2-(3-propylphenyl)-ethane-1,2-dione a yellow oil (82% yield), MS m/e (M−H)$^+$ 317; $^1$H NMR (400 MHz, DMSO-d$_6$) δ0.85 (t, J=7.32 Hz, 3H), 1.57 (m, 2H), 2.6 (t, J=7.32 Hz, 2H), 7.35 (d, J=8.78 Hz, 2H), 7.4-7.5 (m, 3H), 7.65-7.7 (m, 2H), 7.95(d, J=8.78 Hz, 2H).

Step g) 2-Amino-5-[4-(difluoromethoxy)phenyl]-3-methyl-5-(3-propylphenyl)-3,5-dihydro-4H-imidazol-4-one Using essentially the same procedure described in Example 1, step c and employing 1-[4-(difluoromethoxy)phenyl]-2-(3-propylphenyl)ethane-1,2-dione, the hydantoin product was obtained. This product was purified on silica gel (ISCO) using hexanes/MeOH 20/1 as the eluting solvents to give 2-amino-5-[4-(difluoromethoxy)-phenyl]-3-methyl-5-(3-propylphenyl)-3,5-dihydro-4H-imidazol-4-one as a white solid (91% yield), MS m/e (M+H)$^+$ 374; $^1$H NMR (400 MHz, DMSO-d$_6$) δ0.85 (t, J=7.2 Hz, 3H), 1.44 (m, 2H), 2.45 (m, 2H), 2.93 (s, 3H), 6.6 (brs, 2H), 7.0 (d, J=7.2 Hz, 1H), 7.06 (d, J=8.4 Hz, 2H), 7.1-7.3 (m, 4H), 7.4 (d, J=8.54 Hz, 2H).

Step h) (5R)-2-Amino-5-[4-(difluoromethoxy)phenyl]-3-methyl-5-(3-propylphenyl)-3,5-dihydro-4H-imidazol-4-one [A] and (5S)-2-Amino-5-[4-(difluoromethoxy)phenyl]-3-methyl-5-(3-propylphenyl)-3,5-dihydro-4H-imidazol-4-one [B]

The racemic mixture of 2-amino-5-[4-(difluoromethoxy)phenyl]-3-methyl-5-(3-propylphenyl)-3,5-dihydro-4H-imidazol-4-one was separated by chiral chromatography technique (Chiralcel OJ, 0.46×10 cm, using 20% ethanol in CO2 (100 bar) and diethylamine as the mobile phase) to produce the two enantiomers:

[A] (5R)-2-amino-5-[4-(difluoromethoxy)phenyl]-3-methyl-5-(3-propylphenyl)-3,5-dihydro-4H-imidazol-4-one, MS m/e (M+H)$^+$ 374; $^1$H NMR (400 MHz, DMSO-d$_6$) δ 0.85 (t, J=7.2 Hz, 3H), 1.44 (m 2H), 2.45 (m, 2H), 2.93 (s, 3H), 6.6 (brs, 2H), 7.0 (d, J=7.2 Hz, 1H), 7.06 (d, J=8.4 Hz, 2H), 7.1-7.3 (m, 4H), 7.4 (d, J=8.54 Hz, 2H); [a]$_{25}$=+28 (C=1% in MeOH); and

[B] (5S)-2-amino-5-[4-(difluoromethoxy)phenyl]-3-methyl-5-(3-propylphenyl)-3,5-dihydro-4H-imidazol-4-one MS m/e (M+H)+ 374; $^1$H NMR (400 MHz, DMSO-$d_6$) δ0.85 (t, J=7.2 Hz, 3H), 1.44 (m 2H), 2.45 (m, 2H), 2.93 (s, 3H), 6.6 (brs, 2H), 7.0 (d, J=7.2 Hz, 1H), 7.06 (d, J=8.4 Hz, 2H), 7.1-7.3 (m, 4H), 7.4 (d, J=8.54 Hz, 2H); $[a]_{25}$=−26.6 (C=1% in MeOH).

EXAMPLE 5

Preparation of (5R)-2-amino-5-(3-butylphenyl)-5-[4-(difluoromethoxy)phenyl]-3-methyl-3,5-dihydro-4H-imidazol-4-one [A] and (5S)-2-amino-5-(3-butylphenyl)-5-[4-(difluoromethoxy)phenyl]-3-methyl-3,5-dihydro-4H-imidazol-4-one [B]

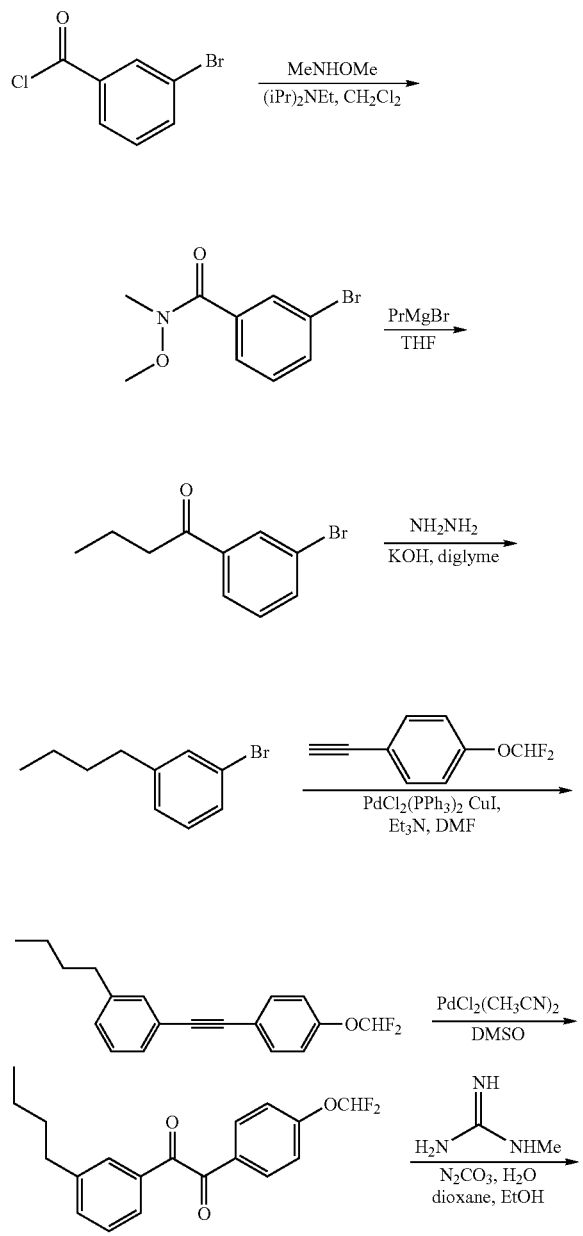

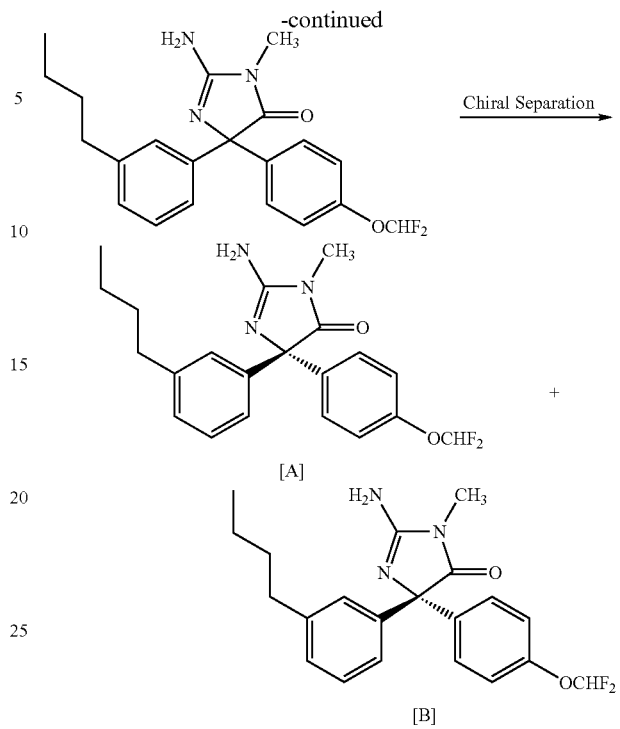

Step a) 3-Bromo-N-methoxy-N-methylbenzamide

A mixture of N-methoxymethanamine hydrochloride (22.1 g, 228.5 mmol), diisopropyl ethyl amine (63.5 mL, 365.6 mmol) and $CH_2Cl_2$ was treated dropwise with 3-bromobenzoyl chloride (15 g, 68.5 mmol) in $CH_2Cl_2$, stirred at room temperature for 30 minutes, and concentrated under vacuum. The resultant residue was dispersed in water and extracted with ethyl ether. The organic extracts were combined, dried over $MgSO_4$ and concentrated in vacuo. The resultant residue was purified on silica gel (Biotage) using hexanes/EtOAc (2/1) as the eluting solvents to give 3-bromo-N-methoxy-N-methylbenzamide as a tan solid (15.1 g, 90% yield).

Step b) 1-(3-Bromophenyl)butan-1-one

A cold (0° C.) solution of 3-bromo-N-methoxy-N-methylbenzamide (3 g, 12.3 mmol) in THF was treated with propylmagnesium bromide (6.15 mL, 12.3 mmol), stirred at room temperature for 1 hour, quenched with aqueous $NH_4Cl$, acidified with HCl (2N) and extracted with ethyl ether. The organic extracts were combined, dried over $MgSO_4$ and concentrated under vacuum. Purification of the resultant residue on silica gel (Biotage) using hexanes/EtOAc (20/1) as the eluting solvents gave 1-(3-bromophenyl)butan-1-one as a tan solid (2.1 g, 75% yield).

Step c) 1-Bromo-3-butylbenzene

A mixture of 1-(3-bromophenyl)butan-1-one (1.0 g, 4.4 mmol) and diglyme (10 mL) was treated with hydrazine (1.49 g, 44 mmol), stirred at 100° C. for 2 h, treated with KOH (1.23 g, 22 mmol), stirred at 150° C. for 6 hours, cooled to room temperature, poured into water and extracted with ethyl ether. The organic extracts were combined, dried over $MgSO_4$ and concentrated under vacuum. Purification of the resultant residue on silica gel (ISCO) using hexanes as the eluting solvent gave 1-bromo-3-butylbenzene as a clear oil (0.81 g, 86% yield).

Step d) 1-Butyl-3-{[4-(difluoromethoxy)phenyl]ethynyl}benzene

Using essentially the same procedure described in Example 1, step a, and employing 1-bromo-3-butylbenzene and 1-(difluoromethoxy)-4-ethynylbenzene, the phenylethynylbenzene product was obtained. This product was purified on silica gel (Biotage) using hexanes/EtOAc 50/1 as the eluting solvents to give 1-butyl-3-{[4-(difluoromethoxy)phenyl]ethynyl}benzene as a colorless oil (0.56 g, 28% yield), MS m/e M+ 300; $^1$H NMR (400 MHz, DMSO-$d_6$) $\delta$0.82 (t, J=7.19 Hz, 3H), 1.25 (m, 2H), 1.55 (m, 2H), 2.56 (t, J=7.56 Hz, 2H), 7.2 (m, 3H), 7.35-7.45 (m, 4H), 7.58 (d, J=8.79 Hz, 2H).

Step e) 1-(3-Butylphenyl)-2-[4-(difluoromethoxy)phenyl]ethane-1,2-dione

Using essentially the same procedure described in Example 1, step b, and employing 1-butyl-3-{[4-(difluoromethoxy)phenyl]ethynyl}benzene, The dione product was obtained. This product was purified on silica gel (ISCO) using hexanes/EtOAc 30/1 as the eluting solvents to yield 1-(3-butylphenyl)-2-[4-(difluoromethoxy)phenyl]-ethane-1,2-dione as a yellow oil (0.39 g, 92% yield), MS m/e (M+H)+ 331; $^1$H NMR (400 MHz, DMSO-$d_6$) $\delta$0.84 (t, J=7.32 Hz, 3H), 1.26 (m, 2H), 1.51 (m, 2H), 2.63 (t, J=7.56 Hz, 2H), 7.35 (d, J=8.78 Hz, 2H), 7.4-7.5 (m, 3H), 7.65-7.7 (m, 2H), 7.95 (d, J=8.78 Hz, 2H).

Step f) 2-Amino-5-(3-butylphenyl)-5-[4-(difluoromethoxy)phenyl]-3-methyl-3,5-dihydro-4H-imidazol-4-one Using essentially the same procedure described in Example 1, step c, and employing 1-(3-butylphenyl)-2-[4-(difluoromethoxy)phenyl]ethane-1,2-dione, the hydantoin product was obtained. This product was purified on silica gel (ISCO) using EtOAc/MeOH 20/1 as the eluting solvents to yield 2-amino-5-(3-butylphenyl)-5-[4-(difluoromethoxy)phenyl]-3-methyl-3,5-dihydro-4H-imidazol-4-one as a white solid, MS m/e (M+H)+ 388; $^1$H NMR (400 MHz, DMSO-$d_6$) $\delta$0.82 (t, J=7.32 Hz, 3H), 1.25 (m 2H), 1.45 (m, 2H), 2.48 (m, 2H), 2.93 (s, 3H), 6.6 (brs, 2H), 7.0 (d, J=7.44 Hz, 1H), 7.1 (d, J=8.78 Hz, 2H), 7.12-7.32 (m, 4H), 7.4 (d, J=8.78 Hz, 2H).

Step g) (5R)-2-Amino-5-(3-butylphenyl)-5-[4-(difluoromethoxy)phenyl]-3-methyl-3,5-dihydro-4H-imidazol-4-one [A] and (5S)-2-Amino-5-(3-butylphenyl)-5-[4-(difluoromethoxy)phenyl]-3-methyl-3,5-dihydro-4H-imidazol-4-one [B]

A racemic mixture of 2-amino-5-(3-butylphenyl)-5-[4-(difluoromethoxy)-phenyl]-3-methyl-3,5-dihydro-4H-imidazol-4-one was separated by chiral chromatography technique [Chiralcel OJ, 0.46×10 cm, using 20% ethanol in $CO_2$ (100 bar) and diethylamine as the mobile phase] to produce the two enantiomers:

[A] (5R)-2-amino-5-(3-butylphenyl)-5-[4-(difluoromethoxy)phenyl]-3-methyl-3,5-dihydro-4H-imidazol-4-one; MS m/e (M+H)+ 388; $^1$H NMR (400 MHz, DMSO-$d_6$) $\delta$ 0.82 (t, J=7.32 Hz, 3H), 1.25 (m 2H), 1.45 (m, 2H), 2.48 (m, 2H), 2.93 (s, 3H), 6.6 (brs, 2H), 7.0 (d, J=7.44 Hz, 1H), 7.1 (d, J=8.78 Hz, 2H), 7.12-7.32 (m, 4H), 7.4 (d, J=8.78 Hz, 2H); [a]$_{25}$=+25 (C=1% in MeOH); and

[B] (5S)-2-amino-5-(3-butylphenyl)-5-[4-(difluoromethoxy)phenyl]-3-methyl-3,5-dihydro-4H-imidazol-4-one; MS m/e (M+H)+ 388, $^1$H NMR (400 MHz, DMSO-$d_6$) $\delta$ 0.82 (t, J=7.32 Hz, 3H), 1.25 (m 2H), 1.45 (m, 2H), 2.48 (m, 2H), 2.93 (s, 3H), 6.6 (brs, 2H), 7.0 (d, J=7.44 Hz, 1H), 7.1 (d, J=8.78 Hz, 2H), 7.12-7.32 (m, 4H), 7.4 (d, J=8.78 Hz, 2H); [a]$_{25}$=−28.8 (C=1% in MeOH).

EXAMPLES 6-10

Preparation of 2-Amino-5-[4-(difluoromethoxy)phenyl]-3-methyl-5-(3-substituted-phenyl)-3,5-dihydro-4H-imidazol-4-one Compounds Using essentially the same procedure described in Example 5, steps d-f, and employing the appropriate 1-bromo-3-alkylbenzene and 1-(difluoromethoxy-4-ethynylbenzene, the compounds shown below were obtained and identified by HNMR and mass spectral analyses.

EXAMPLE 6

2-Amino-5-[4-(difluoromethoxy)phenyl]-3-methyl-5-(3-pentylphenyl)-3,5-dihydro-4H-imidazol-4-one

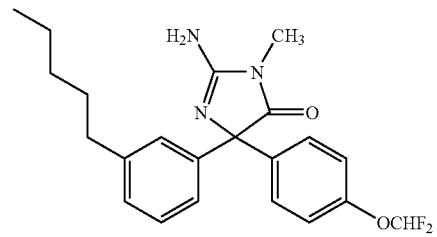

MS m/e (M+H)+ 402; $^1$H NMR (400 MHz, DMSO-$d_6$) $\delta$0.72 (t, J=6.83 Hz, 3H), 1.22 (m 4H), 1.44(m, 2H), 2.48 (m, 2H), 2.93 (s, 3H), 6.6 (brs, 2H), 7.0 (d, J=7.08 Hz, 1H), 7.1 (d, J=8.66 Hz, 2H), 7.12-7.32 (m, 4H), 7.4 (d, J=8.66 Hz, 2H).

EXAMPLE 7

2-Amino-5-[4-(difluoromethoxy)phenyl]-3-methyl-5-[3-(2-methylbutyl)phenyl]-3,5-dihydro-4H-imidazol-4-one

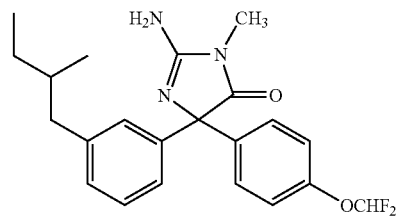

MS m/e (M+H)+ 402; $^1$H NMR (400 MHz, DMSO-$d_6$) $\delta$0.7 (d, J=6.58 Hz, 3H), 0.78 (t, J=7.45 Hz, 3H), 1.05 (m, 1H), 1.24 (m, 1H), 1.48(m, 1H), 2.23 (m, 1H), 2.51 (m, 2H), 2.93 (s, 3H), 6.61 (brs, 2H), 7.0 (d, J=7.07 Hz, 1H), 7.1 (d, J=8.54 Hz, 2H), 7.12-7.32 (m, 4H), 7.4 (d, J=8.54 Hz, 2H).

EXAMPLE 8

2-Amino-5-(3-but-3-en-1-ylphenyl)-5-[4-(difluoromethoxy)phenyl]-3-methyl-3,5-dihydro-4H-imidazol-4-one

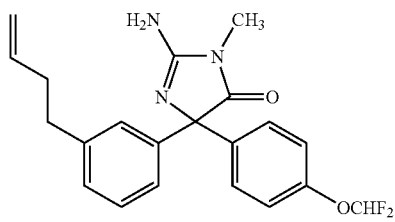

MS m/e (M+H)+ 386; ¹H NMR (400 MHz, DMSO-d₆) δ 2.2 (m, 2H), 2.58 (m, 2H), 2.93 (s, 3H), 4.9 (m, 2H), 5.8 (m, 1H), 6.6 (brs, 2H), 7.8 (m, 3H), 7.1-7.25 (m, 4H), 7.4 (d, J=8.79 Hz, 2H).

EXAMPLE 9

2-Amino-5-[3-(cyclopropylmethyl)phenyl]-5-[4-(difluoromethoxy)phenyl]-3-methyl-3,5-dihydro-4H-imidazol-4-one

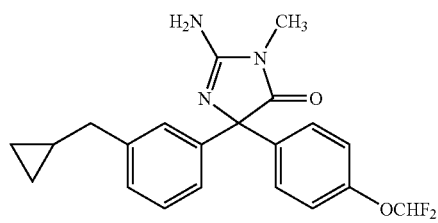

MS m/e (M+H)+ 386; ¹H NMR (400 MHz, DMSO-d₆) δ 0.08 (m, 2H), 0.38 (m, 2H), 0.87 (m, 1H), 2.41 (d, J=6.96 Hz, 1H), 2.93 (s, 3H), 6.6 (brs, 2H), 7.04 (d, J=8.67 Hz, 2H), 7.1-7.3 (m, 5H), 7.44 (d, J=8.67 Hz, 2H).

EXAMPLE 10

3-(3-{2-Amino-4-[4-(difluoromethoxy)phenyl]-1-methyl-5-oxo-4,5-dihydro-1H-imidazol-4-yl}phenyl)propanenitrile

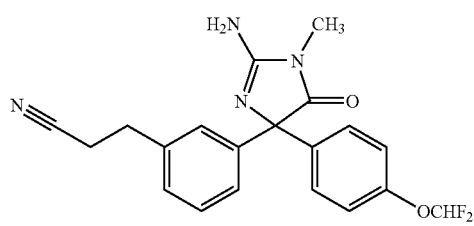

MS m/e (M−H)+ 383; ¹H NMR (400 MHz, DMSO-d₆) δ 2.7 (m, 2H), 2.8 (m, 2H), 2.93 (s, 3H), 6.62 (brs, 2H), 7.05 (d, J=8.66 Hz, 2H), 7.15 (m, 2H), 7.21 (t, J=7.45 Hz, 1H), 7.3 (m, 2H), 7.43 (d, J=8.66 Hz, 2H).

EXAMPLE 11

Preparation of (5R)-2-Amino-5-[4-(difluoromethoxy)phenyl]-3-methyl-5-(3-pent-4-en-1-ylphenyl)-3,5-dihydro-4H-imidazol-4-one [A] and (5S)-2-Amino-5-[4-(difluoromethoxy)phenyl]-3-methyl-5-(3-pent-4-en-1-ylphenyl)-3,5-dihydro-4H-imidazol-4-one [B]

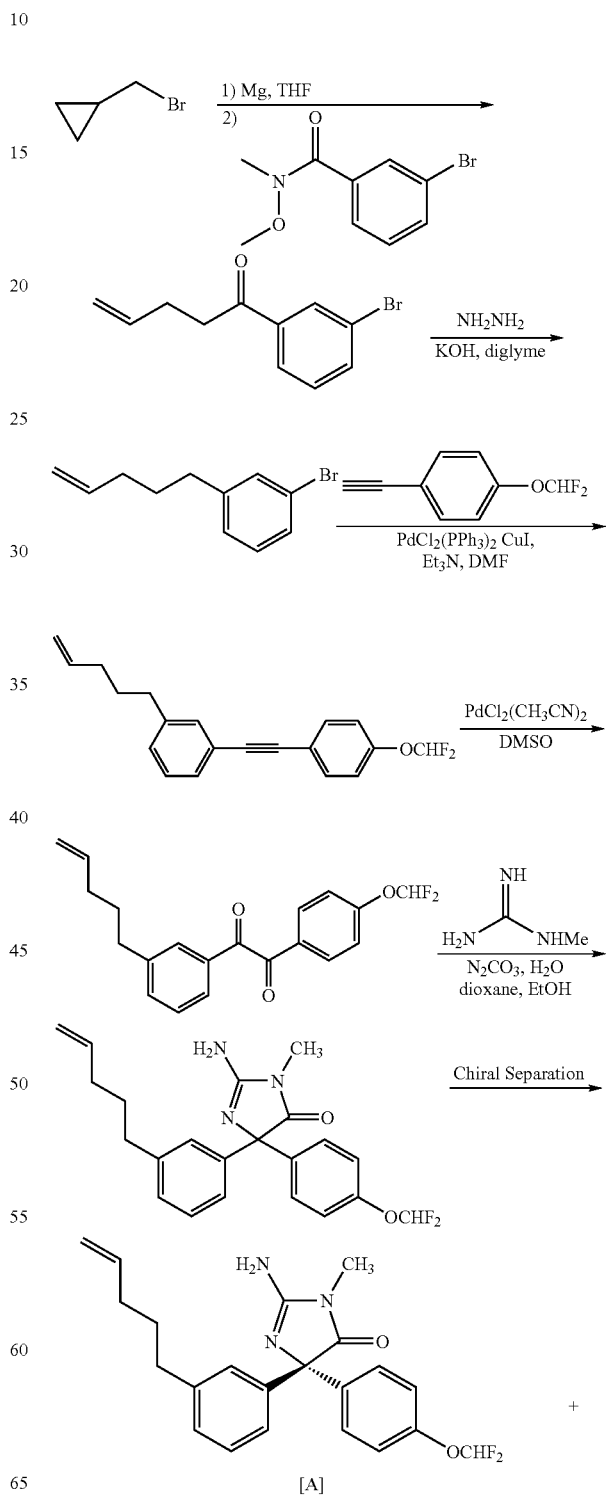

[A]

+

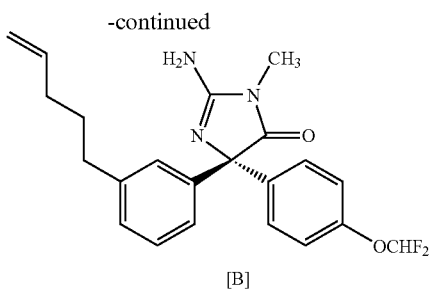

[B]

Step a) 1-(3-Bromophenyl)pent-4-en-1-one

A mixture of magnesium (0.48 g, 20.29 mmol) in THF was treated dropwise with (bromomethyl)cyclopropane (2.49 g, 18.45 mmol) in THF, heated at reflux temperature for 1 hour, poured into a cold (0° C.) mixture of 3-bromo-N-methoxy-N-methylbenzamide (2.5 g, 10.24 mmol) and THF, allowed to come to room temperature, stirred for 10 min, quenched with aqueous NH$_4$Cl and extracted with ethyl ether. The organic extracts were combined, dried over MgSO$_4$ and concentrated in vacuo. Purification of the resultant residue on silica gel (ISCO) using hexanes/EtOAc 10/1 as the eluting solvents gave a clear oil (2.4 g, 54% yield), MS m/e (M−H)$^+$ 239; $^1$H NMR (400 MHz, DMSO-d$_6$) δ2.3 (m, 2H), 3.1 (t, J=7.19 Hz, 2H), 5.02 (m, 2H), 5.8 (m, 1H), 7.47 (t, J=7.93 Hz, 2H), 7.77 (dd, J=7.08, 2.2 Hz), 7.94 (dd, J=7.81, 1.58 Hz), 8.04 (t, J=1.83 Hz, 1H).

Step b) 2-Amino-5-[4-(difluoromethoxy)phenyl]-3-methyl-5-(3-pent-4-en-1-ylphenyl)-3,5-dihydro-4H-imidazol-4-one Using essentially the same procedure described in Example 5, steps d-f, and employing 1-(3-bromophenyl)pent-4-en-1-one and 1-(difluoromethoxy)-4-ethynylbenzene, 2-amino-5-[4-(difluoromethoxy)phenyl]-3-methyl-5-(3-pent-4-en-1-ylphenyl)-3,5-dihydro-4H-imidazol-4-one is obtained, MS m/e (M+H)$^+$ 400, $^1$H NMR (400 MHz, DMSO-d$_6$) δ21.6 (m, 2H), 1.9 (m, 2H), 2.5 (m, 1H), 2.93 (s, 3H), 4.9 (m, 2H), 5.78 (m, 1H), 6.6 (brs, 2H), 7-7.08 (m, 3H), 7.1-7.3 (m, 4H), 7.4 (d, J=8.67 Hz, 2H)

Step c) (5R)-2-Amino-5-[4-(difluoromethoxy)phenyl]-3-methyl-5-(3-pent-4-en-1-ylphenyl)-3,5-dihydro-4H-imidazol-4-one[A] and (5S)-2-Amino-5-[4-(difluoromethoxy)phenyl]-3-methyl-5-(3-pent-4-en-1-ylphenyl)-3,5-dihydro-4H-imidazol-4-one[B]

A racemic mixture of 2-amino-5-[4-(difluoromethoxy)phenyl]-3-methyl-5-phenyl-3,5-dihydro-4H-imidazol-4-one was separated by chiral chromatography technique (Chiralpak AD, 0.46×25 cm, using 10% ethanol in 90% hexane and diethylamine as the mobile phase) to produce the two enantiomers:

[A] (5R)-2-amino-5-[4-(difluoromethoxy)phenyl]-3-methyl-5-(3-pent-4-en-1-ylphenyl)-3,5-dihydro-4H-imidazol-4-one, MS m/e (M+H)$^+$ 400, $^1$H NMR (400 MHz, DMSO-d$_6$) δ 21.6 (m, 2H), 1.9 (m, 2H), 2.5 (m, 1H), 2.93 (s, 3H), 4.9 (m, 2H), 5.78 (m, 1H), 6.6 (brs, 2H), 7-7.08 (m, 3H), 7.1-7.3 (m, 4H), 7.4 (d, J=8.67 Hz, 2H); [a]$_{25}$=+23 (C=1% in MeOH); and

[B] (5S)-2-amino-5-[4-(difluoromethoxy)phenyl]-3-methyl-5-(3-pent-4-en-1-ylphenyl)-3,5-dihydro-4H-imidazol-4-one, MS m/e (M+H)$^+$ 400, $^1$H NMR (400 MHz, DMSO-d$_6$) δ 21.6 (m, 2H), 1.9 (m, 2H), 2.5 (m, 1H), 2.93 (s, 3H), 4.9 (m, 2H), 5.78 (m, 1H), 6.6 (brs, 2H), 7-7.08 (m, 3H), 7.1-7.3 (m, 4H), 7.4 (d, J=8.67 Hz, 2H); [a]$_{25}$=−19 (C=1% in MeOH).

EXAMPLE 12

Preparation of N-(3-{(4R)-2-Amino-4-[4-(difluoromethoxy)phenyl]-1-methyl-5-oxo-4,5-dihydro-1H-imidazol-4-yl}phenyl)-2-methoxyacetamide [A] and N-(3-{(4S)-2-Amino-4-[4-(difluoromethoxy)phenyl]-1-methyl-5-oxo-4,5-dihydro-1H-imidazol-4-yl}phenyl)-2-methoxyacetamide [B]

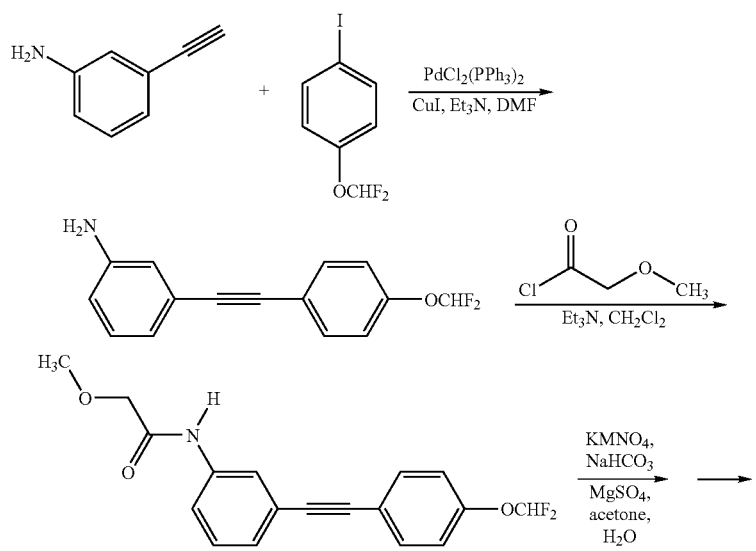

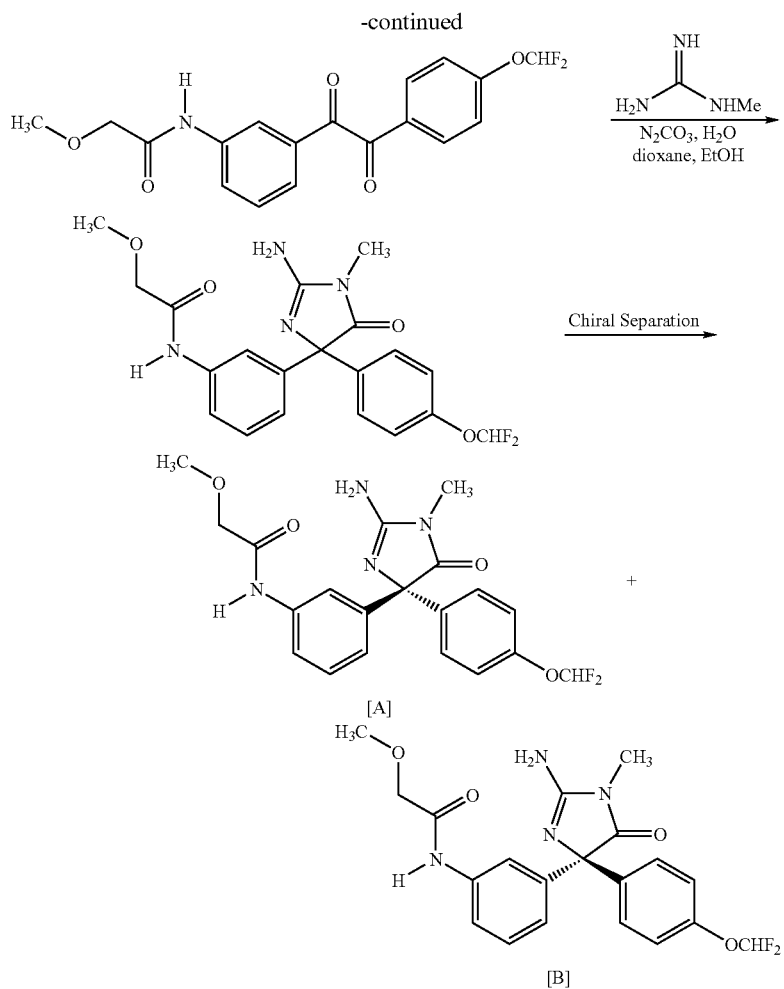

Step a) 3-{[4-(difluoromethoxy)phenyl]ethynyl}aniline

Using essentially the same procedure described in Example 1, step a, and employing 3-ethynylaniline and 1-(difluoromethoxy)-4-iodobenzene, the phenylethynylaniline product was obtained. This product was purified on silica gel (ISCO) using EtOAc/hexanes 1/3 as the eluting solvents to give 3-{[4-(difluoromethoxy)phenyl]ethynyl}aniline as a yellow solid (95% yield), MS m/e (M+H)+ 260; $^1$H NMR (400 MHz, DMSO-$d_6$) δ5.26 (brs, 2H), 6.6 dd(, J=8.17, 2.31 Hz, 1H), 6.67 (dd, 7.44, 2.43 Hz, 1H), 6.72 (d, J=2.4 Hz, 1H), 7.05 (t, J=7.81 Hz, 1H), 7.43 (d, J=6.1 Hz, 2H), 8.55 (d, J=6.1 Hz, 2H).

Step b) N-(3-{[4-(Difluoromethoxy)phenyl]ethynyl}phenyl)-2-methoxyacetamide

A cold (0° C.) solution of 3-{[4-(difluoromethoxy)phenyl]ethynyl}aniline (1 g, 3.86 mmol), triethylamine (0.65 mL, 4.63 mmol) in CH$_2$Cl$_2$ was treated dropwise with methoxyacetyl chloride (0.5 g, 4.63 mmol), allowed to come to room temperature, stirred for 2 hours, poured into water and extracted with EtOAc/ethyl ether 1/1. The organic extracts were combined, dried over MgSO$_4$ and concentrated in vacuo. Purification of the resultant residue on silica gel (Biotage) using hexanes/EtOAc (1/1) as the eluting solvent gave N-(3-{[4-(difluoromethoxy)phenyl]ethynyl}phenyl)-2-methoxyacetamide as a yellow solid (1.25 g, 94% yield), MS m/e (M+H)+ 332; $^1$H NMR (400 MHz, DMSO-$d_6$) δ3.30 (s, 3H), 3.97 (s, 2H), 7.2 (m, 3H), 7.3 (m, 2H), 7.6 (m, 3H), 7.9(t, J=1.7 Hz, 1H), 9.84 (s, 1H).

Step c) N-{3-[[4-(Difluoromethoxy)phenyl](oxo)acetyl]phenyl}-2-methoxyacetamide A mixture of N-(3-{[4-(difluoromethoxy)phenyl]ethynyl}phenyl)-2-methoxyacetamide (0.68 g, 2.05 mmol), acetone, H$_2$O, NaHCO$_3$ (0.1 g, 1.23 mmol), and MgSO$_4$ (0.37 g, 3.07 mmol) was treated with KMnO4 (0.32 g, 2.05 mmol), stirred at room temperature for 4 h and filtered. The filtrate was diluted with water and extracted with ethyl ether. The organic extracts were combined, dried over MgSO$_4$ and concentrated in vacuo. Purification of the resultant residue on silica gel (Biotage) using hexanes/EtOAc (1/1) as the eluting solvent gave N-{3-[[4-(difluoromethoxy)phenyl](oxo)acetyl]phenyl}-2-methoxyacetamide as a yellow oil (0.73 g, 98% yield), MS m/e (M+H)+ 364; $^1$H NMR (400 MHz, DMSO-$d_6$) δ3.32 (s, 3H), 3.96 (s, 2H), 7.34 (d, J=8.91 Hz, 2H), 7.5-7.6 (m, 3H), 7.97 (d, J=8.91 Hz, 2H), 8.05 (dd, J=7.81, 1.7 Hz, 1H), 8.27 (t, J=1.7 Hz, 1H), 10.06 (s, 1H).

Step d) N-(3-{2-Amino-4-[4-(difluoromethoxy)phenyl]-1-methyl-5-oxo-4,5-dihydro-1H-imidazol-4-yl}phenyl)-2-methoxyacetamide Using essentially the same procedure described in Example 1, step c, and employing N-{3-[[4-(difluoromethoxy)phenyl](oxo)acetyl]phenyl}-2-methoxyacetamide, the hydantoin product is obtained. This product was purified on silica gel (ISCO) using EtOAc/MeOH 10/1 as the eluting solvents to give N-(3-{2-amino-4-[4-(difluoromethoxy)phenyl]-1-methyl-5-oxo-4,5-dihydro-1H-imidazol-4-yl}phenyl)-2-methoxyacetamide as a white solid (0.15 g, 70% yield), MS m/e (M+H)$^+$ 419; $^1$H NMR (400 MHz, DMSO-d$_6$) δ2.93 (s, 3H), 3.30 (s, 3H), 3.90 (s, 2H), 6.61 (brs, 2H), 7.08 (m, 3H), 7.2 (m, 2H), 7.44 (d, J=8.78 Hz, 2H), 7.55 (d, J=7.93 Hz, 1H), 7.62 (s, 1H), 9.71 (s, 1H).

Step e) N-(3-{(4R)-2-Amino-4-[4-(difluoromethoxy)phenyl]-1-methyl-5-oxo-4,5-dihydro-1H-imidazol-4-yl}phenyl)-2-methoxyacetamide A racemic mixture of N-(3-{2-amino-4-[4-(difluoromethoxy)phenyl]-1-methyl-5-oxo-4,5-dihydro-1H-imidazol-4-yl}phenyl)-2-methoxyacetamide was separated by chiral chromatography technique (Chiralcel AD, 2×25 cm, using 25% isopropanol in 75% hexane and diethylamine as the mobile phase) to produce the two enantiomers as white solids:

[A] N-(3-{(4R)-2-amino-4-[4-(difluoromethoxy)phenyl]-1-methyl-5-oxo-4,5-dihydro-1H-imidazol-4-yl}phenyl)-2-methoxyacetamide, MS m/e (M+H)$^+$ 419; $^1$H NMR (400 MHz, DMSO-d$_6$) δ2.93 (s, 3H), 3.30 (s, 3H), 3.90 (s, 2H), 6.61 (brs, 2H), 7.08 (m, 3H), 7.2 (m, 2H), 7.44 (d, J=8.78 Hz, 2H), 7.55 (d, J=7.93 Hz, 1H), 7.62 (s, 1H), 9.71 (s, 1H); [a]$_{25}$=+18 (C=1% in MeOH); and

[B] N-(3-{(4S)-2-amino-4-[4-(difluoromethoxy)phenyl]-1-methyl-5-oxo-4,5-dihydro-1H-imidazol-4-yl}phenyl)-2-methoxyacetamide, MS m/e (M+H)$^+$ 419; $^1$H NMR (400 MHz, DMSO-d$_6$) δ2.93 (s, 3H), 3.30 (s, 3H), 3.90 (s, 2H), 6.61 (brs, 2H), 7.08 (m, 3H), 7.2 (m, 2H), 7.44 (d, J=8.78 Hz, 2H), 7.55 (d, J=7.93 Hz, 1H), 7.62 (s, 1H), 9.71 (s, 1H); [a]$_{25}$=−16 (C=1% in MeOH).

EXAMPLE 13

Preparation of 2-Amino-5-[4-(difluoromethoxy)phenyl]-3-methyl-5-[3-(4,4,4-trifluorobutyl)phenyl]-3,5-dihydro-4H-imidazol-4-one

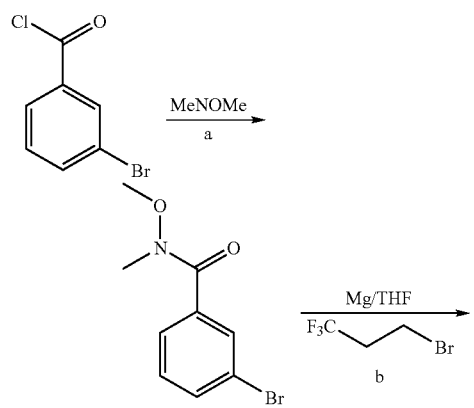

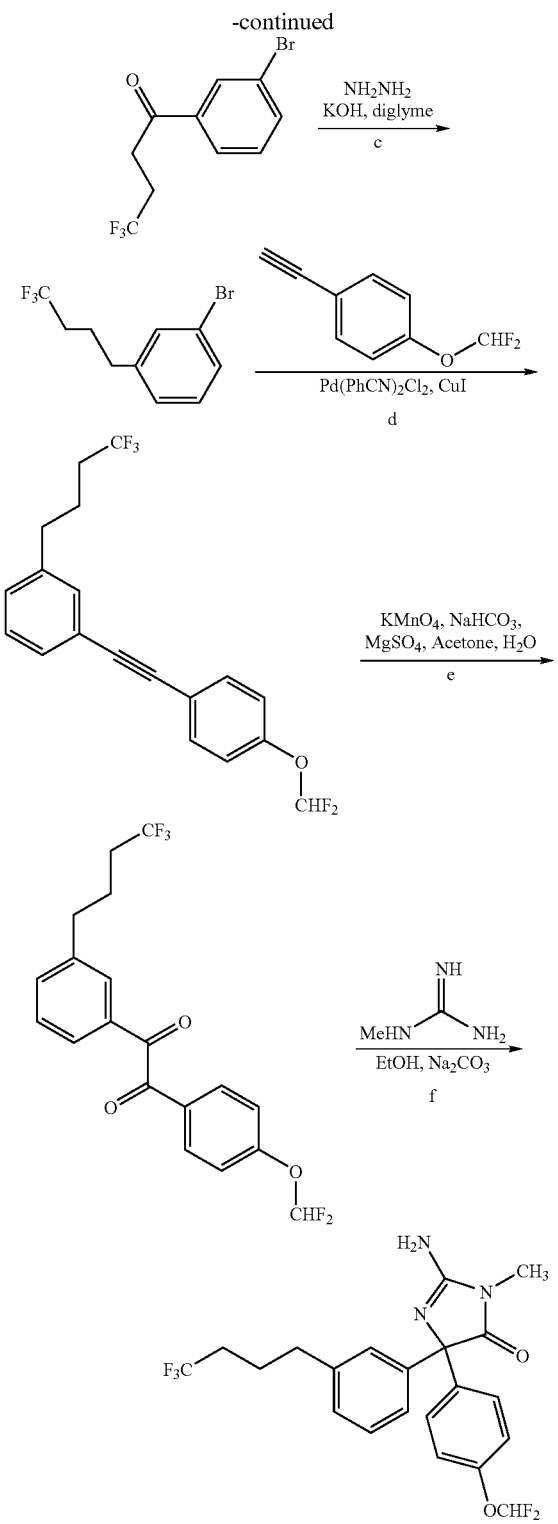

Step a) 3-Bromo-N-methoxy-N-methylbenzamide

A solution of 3-bromobenzoyl chloride (20 g, 91.1 mmol) in CH$_2$Cl$_2$ was added dropwise to a cold (0° C.) solution of N,O-dimethylhydroxylamine hydrochloride (33.6 g, 319 mmol), diisopropylamine (98 mL, 551 mmol) in CH$_2$Cl$_2$ over 1 hour. The stirring continued at room temperature for 30 minutes then concentrated under vacuo. The resultant residue was dispersed in water and extracted with ethyl ether. The organic extracts were combined, dried over $MgSO_4$ and concentrated in vacuo. This residue was purified on silica gel (ISCO) using hexanes/EtOAc (4/1) as the eluting solvent to give 3-bromo-N-methoxy-N-methylbenzamide as light yellow solid (20 g, 89% yield). m/e $(M+H)^+$ 244. $^1H$ NMR (400 MHZ, DMSO-$d_6$) δ ppm, 3.21 (s, 3H), 3.50 (s, 3H), 7.37-7.39, (m, 1H), 7.53-7.55 (m, 1H), 7.64-7.66 (m, 1H), 7.67-7.69 (m, 1H).

Step b) 1-(3-Bromo-phenyl)-4,4,4-trifluoro-butan-1-one

A prepared solution of trifluoromethyl ethane-magnesium bromide (made by refluxing Mg with 1-bromo, 2-trifluoromethyl ethane in THF for 2 hours; 4.6 g=25.82 mmol) in THF was added slowly to a cold (0° C.) solution of 3-bromo-N-methoxy-N-methylbenzamide (3.5 g, 14.3 mmol) in THF. The stirring continued at room temperature for 1 hour, quenched with cold saturated aqueous $NH_4Cl$, acidified with 1 N HCl and extracted with ethyl ether. The organic extracts were combined, dried over $MgSO_4$ and concentrated in vacuo. The crude product was purified on silica gel (ISCO) using hexanes/EtOAc (10/1) as the eluting solvent to give 1-(3-Bromo-phenyl)-4,4,4-trifluoro-butan-1-one as a colorless oil (3.1 g, 77% yield). m/e $(M-H)^-$ 279, 1H NMR (400 MHz, DMSO-$d_6$) δ ppm, 2.5-2.6 (m, 2 H), 3.3-3.4 (m, 2 H), 7.5 (t, J=7.9 Hz, 1 H), 7.8-7.8 (m, 1 H), 7.9-8.0 (m, 1 H), 8.1 (t, J=1.7 Hz, 1 H).

Step c) 1-Bromo-3-(4,4,4-trifluoro-butyl)-benzene

A mixture of 1-(3-bromo-phenyl)-4,4,4-trifluoro-butan-1-one (3.1 g, 11 mmol) and diglyme was treated with hydrazine mono hydrate (5.5 g, 110.3 mmol), and stirred at 100° C. for 2 hours then treated with powder KOH (3.1 g, 55.1 mmol). The stirring continued at 150° C. for 6 hours. The mixture was cooled to room temperature, poured into a mixture of ice/water and extracted with ethyl ether. The extracts were combined, dried over $MgSO_4$ and concentrated in vacuo. The crude product was purified on silica gel (ISCO) using hexanes as the eluting solvent to give 1-Bromo-3-(4,4,4-trifluoro-butyl)-benzene as a colorless oil (2.4 g, 88% yield). m/e $(M)^+$ 266; $^1H$ NMR (400 MHZ, DMSO-$d_6$) δ ppm, 1.7-1.8 (m, 2 H), 2.1-2.2 (m, 2 H), 2.6 (t, J=7.6 Hz, 2 H), 7.2-7.25 (m, 2 H), 7.3-7.35 (m, 1 H), 7.4 (s, 1 H)

Step d) 1-Difluoromethoxy-4-[3-(4,4,4-trifluorobutyl)phenylethynyl]benzene

Using essentially the same procedure described in Example 1, Step a, 1-difluoromethoxy-4-[3-(4,4,4-trifluorobutyl)phenylethynyl]benzene was obtained as a colorless oil (0.19 g, 30% yield). m/e $(M)^+$ 354; $^1H$ NMR (400 MHZ, DMSO-$d_6$) δ ppm, 1.74-1.78 (m, 2H), 2.17-2.21 (m, 2H), 2.62-266 (t, J=7.65 Hz, 2H), 7.17-7.20 (d, J=8.8 Hz, 2H), 7.23-7.39 (m, 5H), 7.56-7.58 (d, J=8.8 Hz, 2H).

Step e) 1-(4-Difluoromethoxyphenyl)-2-[3-(4,4,4-trifluorobutyl)phenyl]ethane-1,2-dione A solution of 1-difluoromethoxy-4-[3-(4,4,4-trifluorobutyl)phenylethynyl]-benzene (7.62 mmol) in acetone is treated with $MgSO_4$ (1.83 g, 15.25 mmol) followed by an aqueous solution of $NaHCO_3$ (0.38 g, 4.57 mmol) in $H_2O$ and $KMnO_4$ (2.41 g, 15.24 mmol). The suspension is stirred for 20 hours, diluted with $H_2O$ and ether and filtered through a pad of solka floc. The filtrate is extracted with ether. The extracts are washed with brine, dried over $MgSO_4$ and concentrated in vacuo to give 1-(4-difluoromethoxyphenyl)-2-[3-(4,4,4-trifluorobutyl)phenyl]ethane-1,2-dione as a yellow oil. m/e $(M-H)^-$ 385; $^1H$ NMR (400 MHZ, $CDCl_3$) δ ppm, 1.8-1.9 (m, 2 H), 2.0-2.1 (m, 2 H), 2.7 (t, J=7.8 Hz, 2 H), 6.6 (t, J=72.6 Hz, 1 H), 7.2-7.2 (m, 2 H), 7.4-7.5 (m, 2 H), 7.7-7.8 (m, 2 H), 8.0-8.0 (m, 2 H),

Step f) 2-Amino-5-[4-(difluoromethoxy)phenyl]-3-methyl-5-[3-(4,4,4-trifluorobutyl)phenyl]-3,5-dihydro-4H-imidazol-4-one Using essentially the same procedure described in Example 1, Step c, the title product was obtained as a white solid, 0.11 g (55% yield), mp 70° C.; m/e $(M-H)^-$ 440.1; $^1H$ NMR (400 MHZ, DMSO-$d_6$) δ ppm, 1.64-1.68 (dd, J=7.9 Hz, 2H), 2.16-219 (m, 2H), 2.54-2.58 (t, J=7.76 Hz, 2H), 2.93 (s, 3H), 6.61 (bs, 2H), 6.93+7.3 (s, 1H), 7.04-7.06 (d, J=8.81 Hz, 2H), 7.18-7.19 (t, J=7.6 Hz, 1H), 7.23 (m, 3H), 7.40-7.42 (d, J=8.81 Hz, 2H).

EXAMPLE 14

Preparation of 5-(3-{2-Amino-4-[4-(difluoromethoxy)phenyl]-1-methyl-5-oxo-4,5-dihydro-1H-imidazol-4-yl}phenyl)pentanenitrile

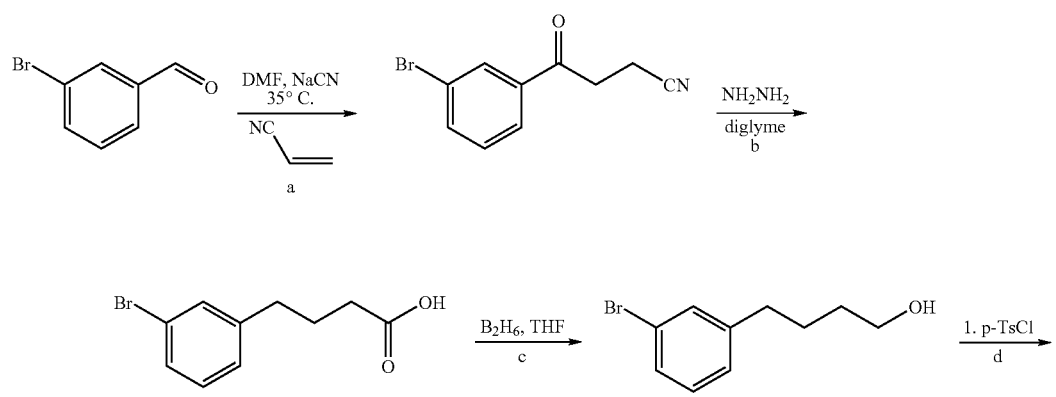

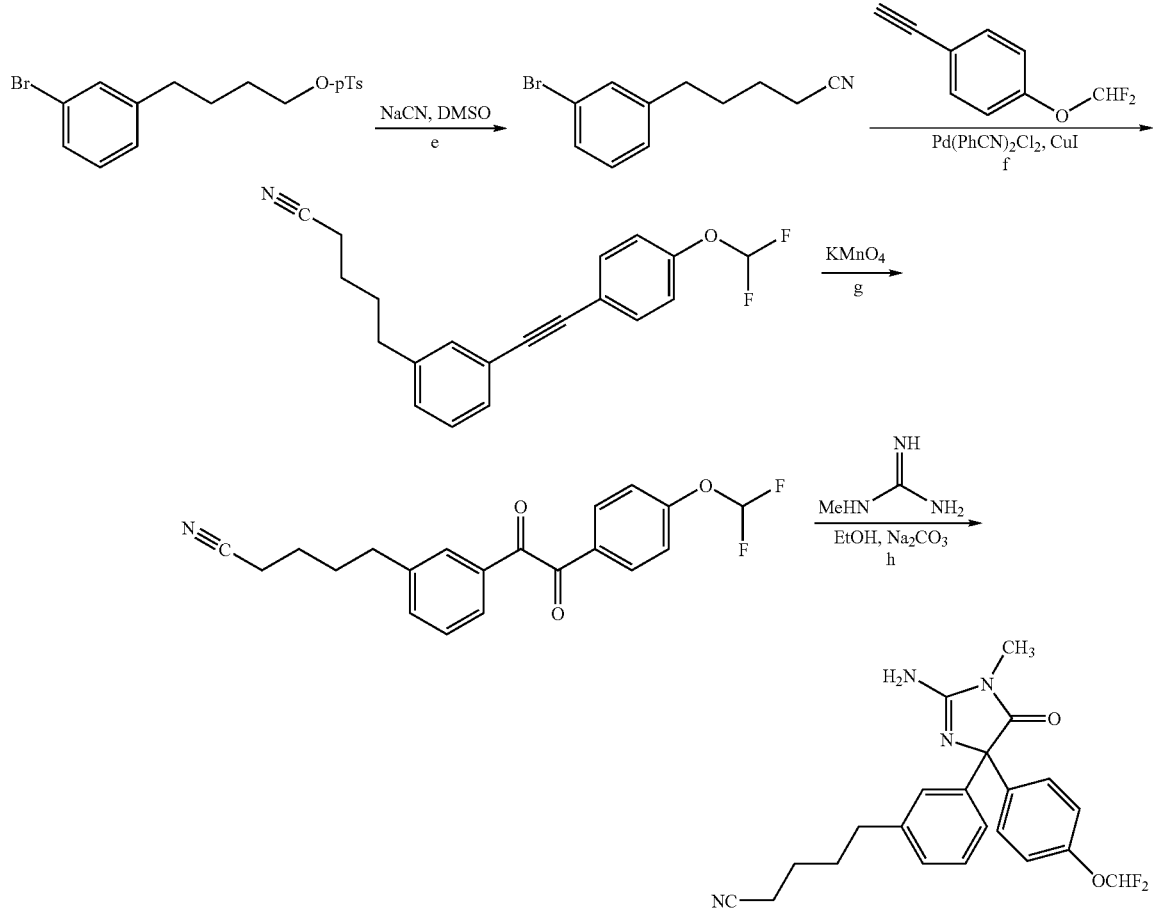

Step a) 4-(3-Bromophenyl)-4-oxo-butyronitrile

A mixture of powder sodium cyanide (1.23 g, 25 mmol) in DMF was treated slowly with a solution of 3-bromo-benzaldehyde in DMF, stirred at 35° C. for 3 hours, cooled to room temperature, poured into a cold 0.5 N HCl solution and extracted with ethyl ether. The extracts were combined, washed with saturated aqueous sodium bicarbonate, brine, dried over MgSO$_4$ and concentrated in vacuo. The resultant residue was triturated in ethyl ether and filtered. The filtercake was dried to give 4-(3-bromophenyl)-4-oxo-butyronitrile as a yellow solid (4 g, 58% yield). m/e (M)$^+$ 237. $^1$H NMR (400 MHZ, DMSO-d$_6$) δ ppm, 2.7 (t, J=6.7 Hz, 2 H), 3.5 (t, J=6.7 Hz, 2 H), 7.5 (t, J=7.8 Hz, 1 H), 7.9 (ddd, J=7.9, 2.1, 0.9 Hz, 1 H), 8.0 (ddd, J=7.8, 1.7, 0.9 Hz, 1 H), 8.1 (t, J=1.7 Hz, 1 H).

Step b) 4-(3-Bromophenyl)butyric acid

The title compound was prepared in substantially the same manner as described in (example 3 step c) and was obtained as light brown oil (2.85 g, 93% yield. m/e (M−H)$^−$ 241. $^1$H NMR (400 MHZ, DMSO-d$_6$) δppm, 1.7-1.8 (m, 2 H), 2.2 (t, J=7.4 Hz, 2 H), 2.6 (t, J=7.9 Hz, 2 H), 7.2-7.2 (m, 1 H), 7.3 (t, J=7.5 Hz, 1 H), 7.4-7.4 (m, 1 H), 7.4-7.4, (m, 1 H), 12.1 (s, 1 H).

Step c) 4-(3-Bromophenyl)butan-1-ol

A cold (0° C.) solution of 4-(3-bromophenyl)butyric acid (2.85 g, 11.7 mmol) in THF was treated slowly with a solution of B$_2$H$_6$-THF (35 mL), stirred at room temperature for 18 hours, poured into ice/water, basified with 2.5 N NaOH to pH=11 and extracted with CH$_2$Cl$_2$. The extracts were combined, washed with brine, dried over MgSO$_4$ and concentrated in vacuo. Purification of the resultant residue by column chromatography using hexanes/CH$_2$Cl$_2$/MeOH (4/4.5/0.5) as the eluting solvent afforded 4-(3-bromophenyl)butan-1-ol as a colorless oil (1.9 g, 70% yield. m/e (M)$^+$ 228; $^1$H NMR (400 MHZ, DMSO-d$_6$) δ ppm, 1.3-1.4 (m, 2 H) 1.5-1.6 (m, 2 H), 2.55-2.59 (m, 2 H), 3.3-3.38 (m, 2H), 4.3 (t, J=7.5, 1H), 7.2-7.2 (m, 1 H), 7.3 (t, J=7.5 Hz, 1 H), 7.4-7.4 (m, 1 H), 7.4-7.4 (m, 1 H).

Step d) Toluene-4-sulfonic acid 4-(3-bromo-phenyl)butyl ester

A cold (0° C.) solution of 4-(3-bromophenyl)butan-1-ol (1.08 g, 4.7 mmol) and p-toluenesulfonyl chloride (1.2 g, 6.3 mmol) in THF was treated slowly with triethyl amine (1.8 mL, 12.3 mmol), stirred at room temperature for 4 hours, poured into cold saturated aqueous NH$_4$Cl and extracted with ether. The organic extracts were combined, washed with brine, dried over MgSO$_4$ and concentrated in vacuo. Purification of the resultant residue on silica gel (ISCO) using (hexanes/EtOAC 9.5/0.5) as the eluting solvent afforded toluene-4-sulfonic acid 4-(3-bromophenyl)-butyl ester as a colorless oil (2.4 g, 76% yield). m/e (M+NH$_4$)$^+$ 400.1. $^1$H NMR (400 MHZ, DMSO-d$_6$) δ ppm, 1.4-1.6 (m, 4 H), 2.4 (s, 3 H), 2.4-2.5 (m, 2 H), 4.0 (t, J=6.0 Hz, 2 H), 7.2 (t, J=7.8 Hz, 1 H), 7.3-7.3 (m, 1 H), 7.3-7.3 (m, J=8.0, 1.0 Hz, 1 H), 7.4-7.5 (m, J=8.6 Hz, 2 H), 7.7-7.8 (m, 2 H).

Step e) 5-(3-Bromophenyl)pentanenitrile

A mixture of toluene-4-sulfonic acid 4-(3-bromophenyl) butyl ester (2.3 g, 6 mmol) and powdered sodium cyanide (0.65 g, 13 mmol) in DMSO was heated up to 80° C., stirred for 1.5 hours and monitored by NMR. When the reaction was complete, the reaction mixture was cooled to room temperature, diluted with $H_2O$ and extracted with $CH_2Cl_2$. The combined organic extracts were washed with brine, dried over $MgSO_4$ and concentrated in vacuo. Purification of this residue on silica gel (ISCO) using (hexanes/EtOAC 9.5/0.5) as the eluting solvent gave 5-(3-bromo-phenyl)pentanenitrile as a colorless oil (1.12 g, 78% yield). m/e (M)+ 237; $^1$H NMR (400 MHZ, DMSO-$d_6$) δ ppm, 2.63-2.65 (m, 2H), 2.75-2.78 (m, 2H), 2.35-2.38 (m, 2H), 2.60-2.63 (m, 2H), 7.05-7.10 (m, 2H), 7.25-7.28 (m, 2H).

Step f) 5-[3-(4-Difluoromethoxyphenylethynyl)phenyl]pentanenitrile

Using essentially the same procedure described in Example 1, Step a, 5-[3-(4-difluoromethoxyphenylethynyl)phenyl]pentanenitrile was obtained as a light brown oil (0.54 g, 88% yield). m/e (M+H)+ 326. $^1$H NMR (400 MHZ, DMSO-$d_6$) δ ppm, 1.5-1.6 (m, 2 H), 1.6-1.7 (m, 2 H), 2.5 (t, J=7.0 Hz, 2 H), 2.6 (t, J=7.5 Hz, 2 H), 7.3 (dd, J=73.7 Hz, 1 H), 7.2-7.3 (m, 2 H), 7.3 (t, J=7.4 Hz, 1 H), 7.4-7.4 (m, 1 H), 7.4-7.4 (m, 1 H).

Step g) 5-{3-[2-(4-Difluoromethoxyphenyl)-2-oxo-acetyl]phenyl}pentanenitrile Using essentially the same procedure described in Example 13, Step e, 5-{3-[2-(4-difluoromethoxyphenyl)-2-oxo-acetyl]phenyl}pentanenitrile was obtained as a light yellow oil (0.46 g, 77% yield). m/e (M+H)+ 358; $^1$H NMR (400 MHZ, CDCl$_3$) δ 1.20 ppm, 1.6-1.8 (m, 2 H), 1.7-2.0 (m, 2 H), 2.3-2.5 (m, J=7.0, 7.0 Hz, 2 H), 2.6-2.9 (m, J=7.5, 7.5 Hz, 2 H), 6.6 (t, J=72.7 Hz, 1 H), 7.2-7.4 (m, 2 H) 7.4-7.6, (m, 2 H) 7.6-7.9, (m, 2 H), 7.9-8.2 (m, 2 H).

Step h) 5-(3-{2-Amino-4-[4-(difluoromethoxy)phenyl]-1-methyl-5-oxo-4,5-dihydro-1H-imidazol-4-yl}phenyl)pentanenitrile Using essentially the same procedure described in Example 1, Step c, the title product was obtained as a white solid, 0.23 g (43% yield), mp 65° C.; m/e (M+H)+ 413 $^1$H NMR (400 MHZ, DMSO-$d_6$) δ ppm, 1.4-1.6 (m, 4 H), 2.4-2.5 (m, 2 H), 2.5 (t, J=7.2 Hz, 2 H), 2.9 (s, 3 H), 6.6 (bs., 2 H), 7.1 (t, J=74.2 Hz, 1 H), 7.0-7.1 (m, 3 H), 7.2 (t, J=7.8 Hz, 1 H), 7.2-7.2, (m, 2 H), 7.4-7.5 (m, 2 H).

EXAMPLE 15

Preparation of 4-(3-{2-amino-4-[4-(difluoromethoxy)phenyl]-1-methyl-5-oxo-4,5-dihydro-1H-imidazol-4-yl}phenyl)butanenitrile

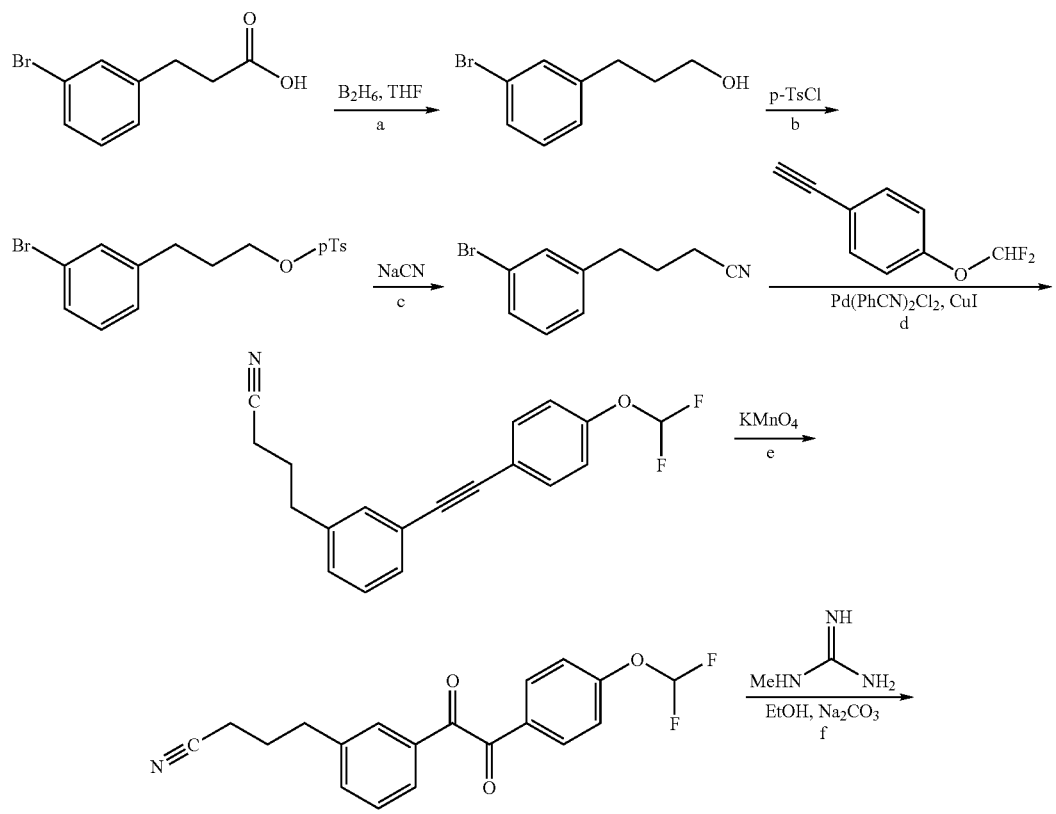

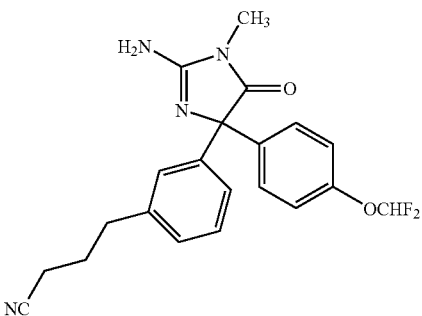

Using essentially the same procedure described in Example 14 and employing 3-(3-bromophenyl)propanoic acid, the title product was obtained as a white solid, 0.23 g (48% yield), mp 75° C.; m/e (M+H)+ 399. $^1$H NMR (400 MHZ, DMSO-d$_6$) δ ppm, 1.73-1.76 (m, 2 H), 2.44-2.46 (m, 2 H), 2.55-2.59 (t, J=7.8 Hz, 2 H), 2.9 (s, 3 H), 6.6 (bs., 2 H), 7.05-7.07 (d, J=8.7 Hz, 2 H), 7.13-7.32 (m, 5 H), 7.41-7.43 (d, J=8.7 Hz, 2 H).

EXAMPLE 16

Preparation of 2-Amino-5-[3-(1,4-difluorobutyl)phenyl]-5-[4-(difluoromethoxy)phenyl]-3-methyl-3,5-dihydro-4H-imidazol-4-one

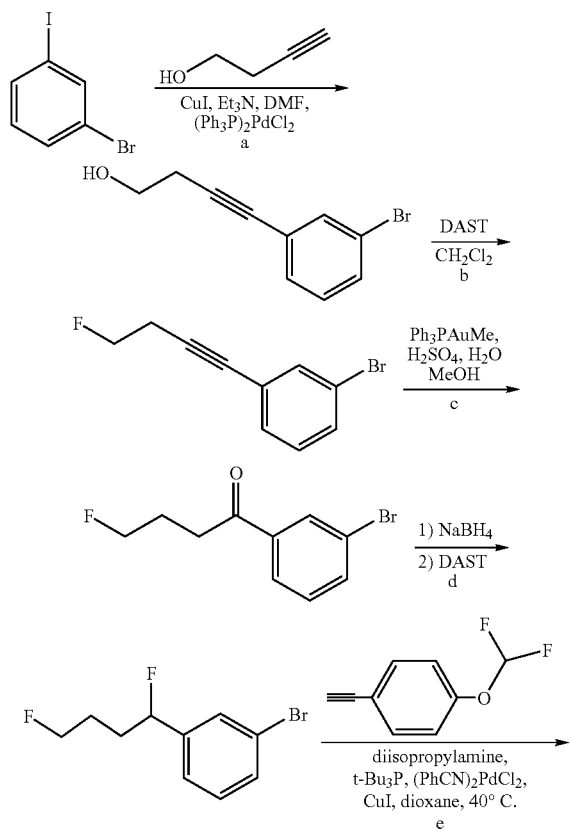

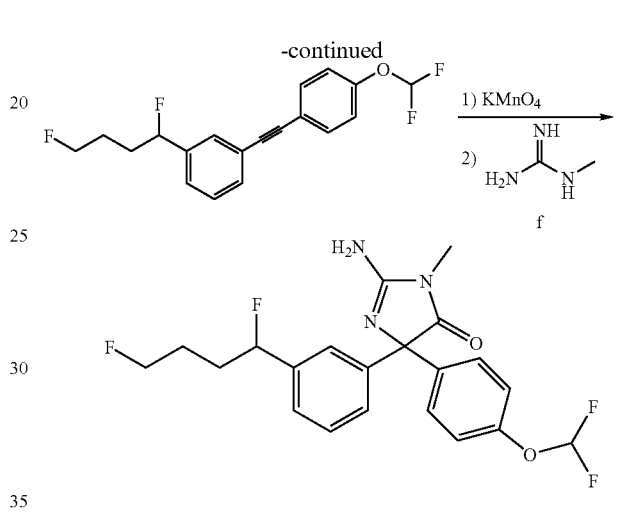

Step a) 4-(3-Bromophenyl)but-3-yn-1-ol

A solution of 10.0 gm (35.3 mmol) of 3-iodo-bromobenzene in DMF was treated with 2.95 mL (88 mmol) of 4-butyne-1-ol, 0.2 gm (1.06 mmol) of copper (I) iodide, 1.23 gm of dichlorobis(triphenylphosphine)-palladium(II), and 49 mL (0.35 mol) of triethylamine, stirred at room temperature for 18 h, poured into water and extracted with EtOAc. The combined extracts were washed sequentially with water and brine, dried over Na$_2$SO$_4$ and concentrated at reduced pressure. Chromatography of the resultant concentrate on silica gel with a gradient of 5% to 30% EtOAc-hexanes afforded 4-(3-bromophenyl)but-3-yn-1-ol as an orange oil, 7.3 gm (92% yield); $^1$H NMR (400 MHz, CDCl$_3$) δ: 1.79 (s, 1H), 2.67 (t, 2H, J=6.3 Hz), 3.80 (t, 2H, J=6.3 Hz), 7.14 (t, 1H, J=7.9 Hz), 7.30 (d, 1H, J=7.9 Hz), 7.41 (m, 1H), 7.54 (t, 1H, J=1.6 Hz).

Step b) 1-Bromo-3-(4-fluoro-but-1-ynyl)benzene

A solution of 1.5 gm (6.67 mmol) of 4-(3-bromophenyl)but-3-yn-1-ol in CH$_2$Cl$_2$ at 0° C. was treated with 2.0 mL (15.3 mmol) of DAST, stirred at 0° C. for 1 h, allowed to warm to room temperature for 1 h, poured into saturated sodium bicarbonate and extracted with EtOAc. The combined extracts were washed sequentially with water and brine, dried over Na$_2$SO$_4$ and concentrated under reduced pressure. Chromatography of the resultant concentrate on silica gel with a gradient of 0% to 24% EtOAc-hexanes gave 1-Bromo-3-(4-fluoro-but-1-ynyl)benzene as a volatile liquid, 0.96 gm (64% yield); ¹H NMR (400 MHz, CDCl₃) δ: 2.82 (dt, 2H, J=6.6, 19.8 Hz), 4.56 (dt, 2H, J=6.6,46.4 Hz), 7.14 (t, 2H, J=7.9 Hz), 7.31 (m, 1H), 7.41 (m, 1H), 7.55 (t, 1H, J=1.7 Hz).

Step c) 1-(3-Bromophenyl)-4-fluorobutan-1-one

A mixture of 0.2 gm (0.89 mmol) of 1-bromo-3-(4-fluorobut-1-ynyl)benzene, 2 mL of MeOH, 1 mg of methyl(triphenylphosphine)gold (I), 25 μL of conc. H₂SO₄ and 0.44 mL of H₂O was placed in a sealed tube, flushed with argon, heated to 72° C. for 2 h and was cooled. The reaction mixture was diluted with EtOAc, washed sequentially with water and brine, dried over Na₂SO₄ and concentrated under reduced pressure. Chromatography of the concentrate on silica gel with a gradient of 0% to 20% EtOAc-hexanes gave 1-(3-bromophenyl)-4-fluorobutan-1-one as an oil, 0.086 gm (40% yield); ¹H NMR (400 MHz, CDCl₃) δ: 2.13 (m, 2H), 3.09 (t, 2H, J=7.1 Hz), 4.53 (dt, 2H, J=5.8, 47.1 Hz), 7.33 (t, 1H, J=7.8 Hz), 7.66 (dq, 1H, J=1.0, 7.8 Hz), 7.55 (dq, 1H, J=1.0, 7.8 Hz), 8.07 (t, 1H, J=1.7 Hz).

Step d) 1-Bromo-3-(1,4-difluoro-butyl)benzene

A solution of 0.3 gm (1.22 mmol) of 1-(3-bromo-phenyl)-4-fluorobutan-1-one in THF at 0° C. was treated with 0.055 gm (1.47 mmol) of solid NaBH₄, stirred at 0° C. for 0.5 h, allowed to warm to room temperature, stirred for 18 h, quenched with aqueous NH₄Cl and poured into EtOAC. The phases were separated. The organic phase was washed sequentially with water and brine, dried over Na₂SO₄ and concentrated under reduced pressure to give 1-(3-bromophenyl)-4-fluorobutan-1-ol as an oil, 0.29 gm (96% yield) of an oil. This oil was dissolved in CH₂Cl₂, cooled to 0° C., treated with 0.23 mL (1.75 mmol) of DAST, stirred at 0° C. for 0.5 h, allowed to warm to room temperature, and stirred at room temperature for 18 h, quenched with water and poured into EtOAc. The phases were separated. The organic phase was washed sequentially with water and brine, dried over Na₂SO₄ and carefully concentrated at reduced pressure. The concentrate was used without further purification in Step e.

Step e) 1-(3-{[4-(Difluoromethoxy)phenyl] ethynyl}phenyl)-1,4-difluorobutane

To a degassed solution of 13 mg (0.034 mmol) of bis (benzonitrile)dichloropalladium (II) in dioxane was added 0.145 gm (0.072 mmol) of a 10% (wt/wt) tri-t-butylphosphine in hexanes. The reaction mixture was stirred for 15 minutes at room temperature, treated with 4.3 mg of copper(I) iodide followed by 0.21 mL of diisopropylamine, stirred for 10 min, treated with 0.28 gm (1.14 mmol) of 1-bromo-3-(1,4-difluoro-butyl)benzene and 0.25 gm (1.48 mmol) of 1-difluoromethoxy-4-ethynylbenzene dissolved in 2 mL of dioxane. The reaction mixture was heated to 35° C. for 0.5 h, allowed to cool to room temperature, stirred at room temperature for 3 h, poured into EtOAc. The organic phase was separated, washed sequentially with water and brine, dried over Na₂SO₄ and concentrated under reduced pressure. Chromatography of the concentrate on silica gel with a gradient of 0% to 25% EtOAc-hexanes afforded 1-(3-{[4-(difluoromethoxy)phenyl]ethynyl}phenyl)-1,4-difluorobutane as an oil, 0.314 gm (82% yield); ¹H NMR (400 MHz, CDCl₃) δ: 1.77-2.07 (m, 4H), 4.51 (m, 2H), 5.48 (dq, 1H, J=4.4, 47.6 Hz), 6.51 (t, 1H, J=73.5 Hz), 7.08 (d, 1H, J=8.6 Hz), 7.22-7.36 (m, 3H), 7.45-7.52 (m, 3H).

Step f) 2-Amino-5-[3-(1,4-difluorobutyl)phenyl]-5-[4-(difluoromethoxy)phenyl]-3-methyl-3,5-dihydro-4H-imidazol-4-one Using essentially the same procedures described in Example 13, Step e, and Example 1, Step c, and employing 1-(3-{[4-(difluoromethoxy)phenyl]ethynyl}phenyl)-1,4-difluorobutane as starting material, the title product was obtained as a foamy solid, mp 54-57° C.; ¹H NMR (400 MHz, DMSO-d₆) δ: 1.61-1.91 (m, 4H), 2.94 (s, 3H), 4.34-4.50 (m, 2H), 5.43-5.58 (m, 1H), 6.67 (br s, 2H), 7.06 (d, 2H, J=8.8 Hz), 7.12 (t, 1H, J=74.2 Hz), 7.2 (d, 1H, J=7.4 Hz), 7.28 (d, 1H, J=7.7 Hz), 7.40 (m, 4H). MS (ESI) m/z 424.2 ([M+H])⁺ and MS (ESI) m/z 422.2 ([M−H])⁻

EXAMPLE 17

Preparation of 2-Amino-5-[4-(difluoromethoxy)phenyl]-5-[3-(3-fluorobut-3-en-1-yl)phenyl]-3-methyl-3, 5-dihydro-4H-imidazol-4-one

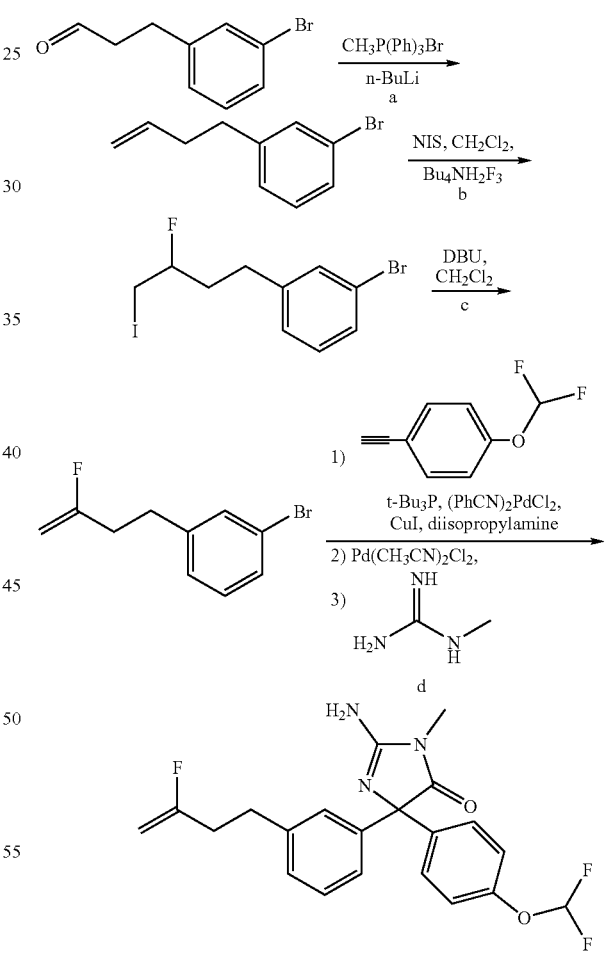

Step a) 1-Bromo-3-but-3-enylbenzene

A solution of 1.34 gm (3.77 mmol) of methyltriphenylphosphonium bromide in THF at 0° C. was treated dropwise with 2.3 mL of 1.6 M n-BuLi in hexanes (3.77 mmol), stirred at 0° C. for 0.25 h, cooled to −78° C., treated dropwise with a solution of 3-(3-bromophenyl)propionaldehyde (0.7 gm, 3.28 mmol) in THF, stirred at −78° C. for 1 h, allowed to warm to room temperature, quenched with aqueous NH$_4$Cl and concentrated under reduced pressure. The resultant residue was taken up in EtOAc, washed sequentially with water and brine, dried over Na$_2$SO$_4$ and concentrated under reduced pressure. Chromatography of this concentrate on silica gel with a gradient of 0.5% EtOAc-hexanes to 2.0% EtOAc-hexanes gave 1-bromo-3-but-3-enylbenzene as an oil, 0.35 gm (50% yield); $^1$H NMR (400 MHz, CDCl$_3$) δ: 2.33 (m, 2H), 2.66 (t, 2H, J=7.4 Hz), 4.98 (m, 2H), 5.79 (m, 1H), 7.12 (m, 2H), 7.30 (m, 2H).

Step b) 1-Bromo-3-(3-fluoro-4-iodo-butyl)-benzene

A solution of 0.245 gm (1.16 mmol) of 1-bromo-3-but-3-enylbenzene in CH$_2$Cl$_2$ at 0° C. was treated with 0.39 gm (1.74 mmol) of N-iodosuccinimide and 1.05 gm (1.74 mmol) of 50% wt/wt tetrabutylammoniumdihydrogen trifluoride in CH$_2$Cl$_2$, stirred at 0° C. for 2 h, warmed to room temperature over a 1 h period and poured into CH$_2$Cl$_2$. The resultant organic phase was washed sequentially with water and brine, dried over Na$_2$SO$_4$ and concentrated under reduced pressure. Chromatography of the concentrate on silica gel with a gradient of hexanes to 7.0% EtOAc-hexanes afforded 1-bromo-3-(3-fluoro-4-iodo-butyl)-benzene as an oil, 0.40 gm (50% yield); $^1$H NMR (400 MHz, CDCl$_3$) δ: 2.03 (m, 2H), 2.74 (m, 2H), 3.29 (dd, 2H, J=5.4, 19.1 Hz), 4.47 (m, 1H), 7.12 (m, 2H), 7.32 (m, 2H).

Step c) 1-Bromo-3-(3-fluorobut-3-enyl)benzene

A solution of 0.405 gm (1.1 mmol) of 1-bromo-3-(3-fluoro-4-iodobutyl)-benzene in CH$_2$Cl$_2$ was treated with 0.82 mL (5.5 mmol) of DBU at room temperature, stirred at room temperature for 24 h and poured into EtOAc. The resultant organic phase was washed sequentially with water and brine, dried over Na$_2$SO$_4$ and concentrated under reduced pressure. Chromatography of the concentrate on silica gel with a gradient of hexanes to 7.0% EtOAc-hexanes gave 1-bromo-3-(3-fluorobut-3-enyl)benzene as an oil, 0.20 gm (80% yield); $^1$H NMR (400 MHz, CDCl$_3$) δ: 2.45 (m, 2H), 2.78 (t, 2H, J=7.8 Hz), 3.29 (dd, 1H, J=2.8, 50.1 Hz), 4.50 (dd, 1H, J=2.8, 7.3 Hz), 7.12 (m, 2H), 7.32 (m, 2H).

Step d) 2-Amino-5-[4-(difluoromethoxy)phenyl]-5-[3-(3-fluorobut-3-en-1-yl)phenyl]-3-methyl-3,5-dihydro-4H-imidazol-4-one Using essentially the same procedure described in Example 1, Steps a, b and c, and employing 1-bromo-3-(3-fluorobut-3-enyl)benzene as starting material, the title product was obtained as a yellow-tan foamy solid, mp 58-60° C.; $^1$H NMR (400 MHz, DMSO-d$_6$) δ: 2.39 (m, 2H), 2.64 (m, 2H), 2.93 (s, 3H), 4.29 (dd, 1H, J=8.8, 52.0 Hz), 4.47 (dd, 1H, J=2.9, 18.2 Hz), 7.05 (brs, 2H), 7.12 (t, 1H, J=74.2 Hz), 7.08 (m, 3H), 7.15 (m, 1H), 7.25 (m, 1H), 7.40 (m, 2H), 7.54 (m, 1H); MS (ESI) m/z 404.1 ([M+H])$^+$ and MS (ESI) m/z 402.1 ([M−H])$^-$.

EXAMPLE 18

Preparation of 2-Amino-5-[3-(4,4-difluorobut-3-en-1-yl)phenyl]-5-[4-(difluoromethoxy)phenyl]-3-methyl-3,5-dihydro-4H-imidazol-4-one

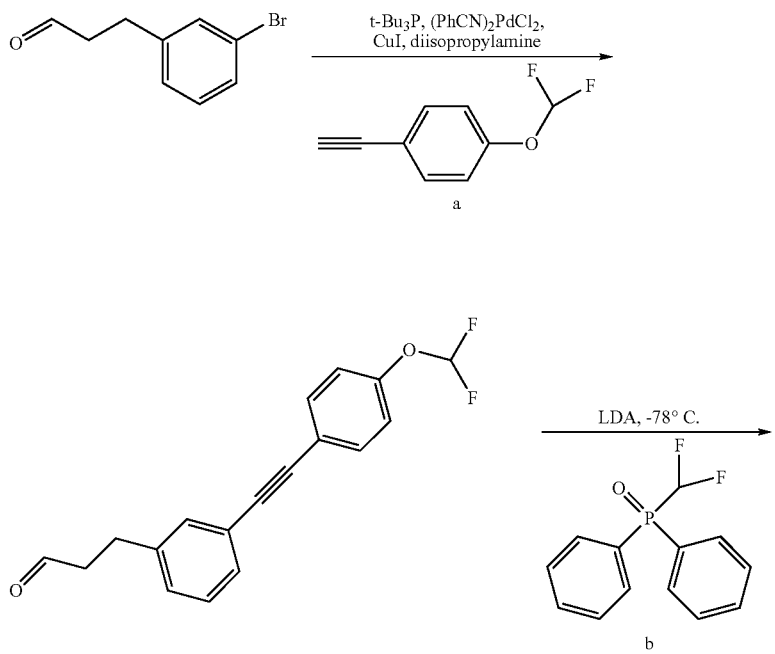

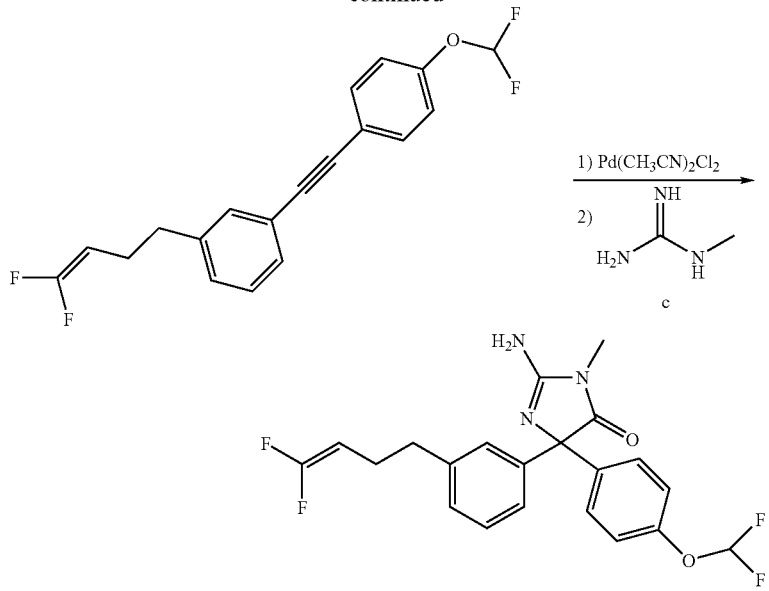

Step a) 3-[3-(4-Difluoromethoxyphenylethynyl)phenyl]propionaldehyde

Using essentially the same procedure described in Example 16, step e, and employing 3-(3-bromophenyl)propionaldehyde in place of 1-bromo-3-(1,4-difluorobutyl)benzene afforded 3-[3-(4-difluoromethoxy-phenylethynyl)phenyl]propionaldehyde as an oil in 42% yield. This oil was used without further purification in the next step.

Step b) 1-(3-{[4-(Difluoromethoxy)phenyl]ethynyl}phenyl)-4,4-difluorobut-3-ene A solution of 0.122 mL (0.86 mmol) of diisopropylamine in THF at −78° C. was treated with 0.54 mL (0.54 mmol) of 1.6 M n-BuLi in hexanes, stirred at −78° C. for 0.5 h, treated dropwise with a solution of 0.22 gm (0.86 mmol) of difluoromethyldiphenylphosphine oxide in THF, stirred at −78° C. for 45 min, treated with a solution of 3-[3-(4-difluoromethoxyphenylethynyl)phenyl]propionaldehyde 0.17 gm (0.58 mmol) in THF, stirred at −78° C. for 4 h, warmed to room temperature, stirred at room temperature for 18 h and diluted with $CH_2Cl_2$. The organic phase was washed sequentially with water and brine, dried over $Na_2SO_4$ and concentrated under reduced pressure. Chromatography of this concentrate on silica gel with a gradient of hexanes to 10% EtOAc-hexanes yielded 1-(3-{[4-(difluoromethoxy)phenyl]ethynyl}-phenyl)-4,4-difluorobut-3-ene as an oil, 0.09 gm (52% yield); $^1$H NMR (400 MHz, $CDCl_3$) δ: 2.29 (m, 2H), 2.66 (t, 2H, J=7.6 Hz), 4.13 (m, 1H), 6.50 (t, 1H, J=73.6 Hz), 7.07 (d, 2H, J=8.8 Hz), 7.13 (m, 1H), 7.26 (d, 1H, J=8.8 Hz), 7.34 (m, 2H), 7.49 (dt, 2H, J=2.1, 2.6, 8.3 Hz).

Step c) 2-Amino-5-[3-(4,4-difluorobut-3-en-1-yl)phenyl]-5-[4-(difluoromethoxy)phenyl]-3-methyl-3,5-dihydro-4H-imidazol-4-one Using essentially the same procedure described in Example 1, Steps b and c, and employing 1-(3-{[4-(difluoromethoxy)phenyl]ethynyl}phenyl)-4,4-difluorobut-3-ene as starting material, the title compound is obtained as a light yellow solid, mp 59-62° C.; $^1$H NMR (400 MHz, DMSO-$d_6$) δ: 2.14 (q, 2H, J=7.4 Hz), 2.49 (m, 2H), 2.93 (s, 3H), 4.37 (m, 1H), 6.60 (brs, 2H), 7.05 (d, 2H, J=8.7 Hz), 7.12 (t, 1H, J=74.2 Hz), 7.18 (m, 2H), 7.21 (m, 2H), 7.40 (d, 2H, J=8.7 Hz); MS (ESI) m/z 422.1 ([M+H])$^+$ and MS (ESI) m/z 420.1 ([M−H])$^-$.

EXAMPLE 19

Preparation of 2-Amino-5-[3-(4,4-difluorobutyl)phenyl]-5-[4-(difluoromethoxy)phenyl]-3-methyl-3,5-dihydro-4H-imidazol-4-one

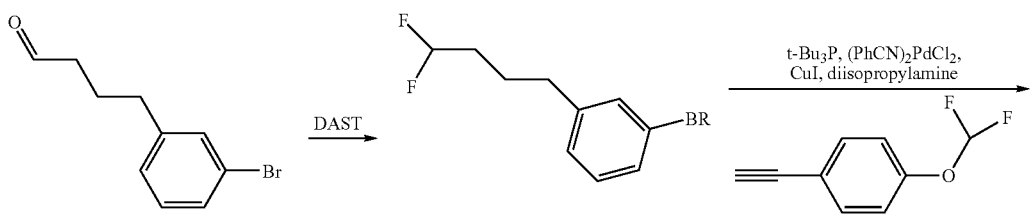

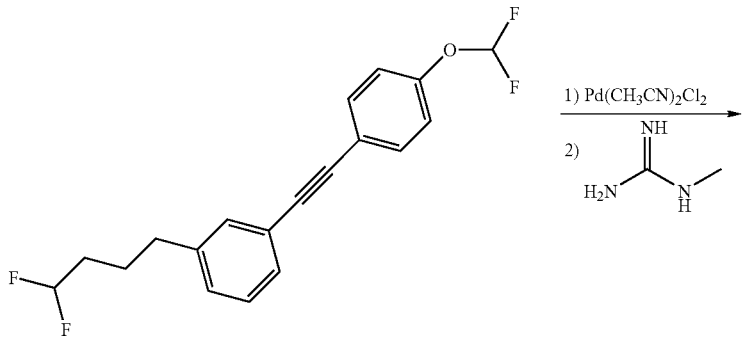

Step a) 1-Bromo-3-(4,4-difluorobutyl)benzene

A solution of 4-(3-bromophenyl)butyraldehyde (0.6 g, 2.6 mmol) in pentane was treated with a solution diethylaminosulfur trifluoride (DAST) (0.38 mL, 2.8 mmol) in pentane, stirred at room temperature for 1 hr, poured into water and extracted with ether. The extracts were combined, washed with brine, dried over magnesium sulfate and concentrated in vacuo. The resultant residue was purified by flash chromatography on silica gel in hexane) to afford 1-bromo-3-(4,4-difluorobutyl)benzene as a clear oil, 0.36 g (54% yield); $^1$H NMR (DMSO-$d_6$) δ 1.7 (m, 4H); 2.6 (t, 2H); 6.6 (txd, 1H); 7.2 (m, 2H); 7.38 (d, 1H), 7.39 (s, 1H). mass spectrum [(+)ESI] m/z=248 [M–H]$^+$.

Step b) 2-Amino-5-[3-(4,4-difluorobutyl)phenyl]-5-[4-(difluoromethoxy)-phenyl]-3-methyl-3,5-dihydro-4H-imidazol-4-one Using essentially the same procedure described in Example 18, Steps a and c, and employing 1-bromo-3-(4,4-difluorobutyl)-benzene and 1-difluoromethoxy-4-ethynyl-benzene as reactants, the title compound was obtained as a white solid, 0.17 g (42% yield), mp 54-57° C.; $^1$H NMR (DMSO-$d_6$) δ 1.6 (m, 2H); 1.8 (m, 2H); 2.5 (t, 2H); 2.95 (s, 3H); 6.0 (txd, 1H); 6.6 (b, 2H); 7.1 (m, 4H); 7.4 (d, 2H). MS [(+)ESI] m/z 424 [M–H]$^+$.

EXAMPLE 20

Preparation of 2-Amino-5-[4-(difluoromethoxy)phenyl]-5-[3-(4-hydroxybut-1-yn-1-yl)phenyl]-3-methyl-3,5-dihydro-4H-imidazol-4-one

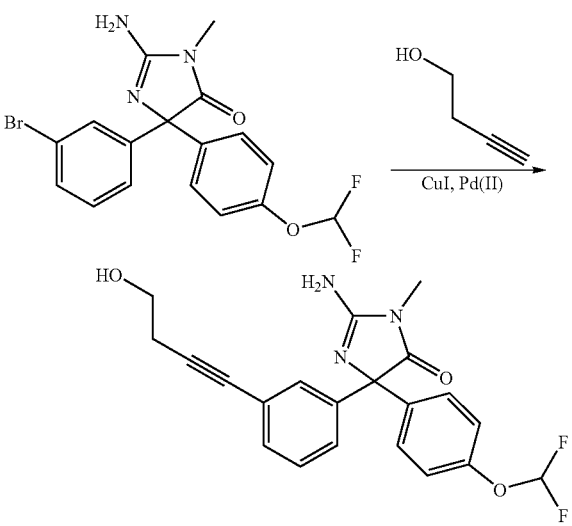

A mixture of copper iodide (8 mg, 0.04 mmol), bis(benzonitrile)dichloro palladium(II) (23 mg, 0.06 mmol) and anhydrous dioxane under argon was stirred for 3 min., treated with tri-t-butyl phosphine (10% in hexane) (240 mg, 0.12 mmol), stirred for 5 min. treated with diisopropyl amine (0.33 mL, 2.4 mmol) followed by a solution of 2-amino-5-(3-bromophenyl)-5-[4-(difluoromethoxy)phenyl]-3-methyl-3,5-dihydro-4H-imidazol-4-one (0.82 g, 2 mmol) in dioxane and 1-hydroxy-2-propyne (0.47 mL, 0.006 mmol). The reaction mixture was heated to 35° C. for 30 min., poured into water and extracted with ethyl acetate. The extracts were combined, washed with brine, dried over sodium sulfate and concentrated under reduced pressure. The resultant residue was purified by flash chromatography on silica gel, 1$^{st}$ in ethyl acetate 2$^{nd}$ 5% methanol/ethyl acetate as eluent to afford the title compound as a white solid, 0.39 g (48% yield), mp 90-93° C.; $^1$H NMR (DMSO-d$_6$) δ 2.5 ((2H, under DMSO peak); 2.95 (s, 3 H); 3.5 (q, 2 H); 4.8 (t, 1 H); 6.6 (b, 2H); 7.1 (d, 2H); 7.15 (t, 2F); 7.2 (m, 2 H); 7.3 (m, 4 H); MS [(+)ESI] m/z=400.2 [M–H]$^+$.

EXAMPLE 21

Preparation of 2-Amino-5-[4-(difluoromethoxy)phenyl]-5-[3-(4-hydroxybutyl)phenyl]-3-methyl-3,5-dihydro-4H-imidazol-4-one

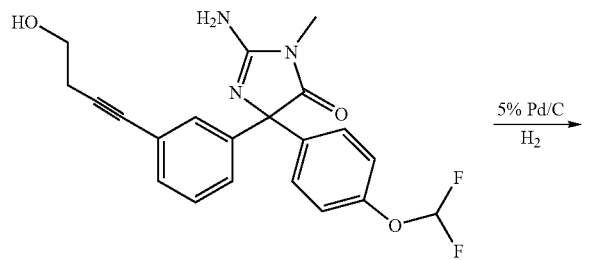

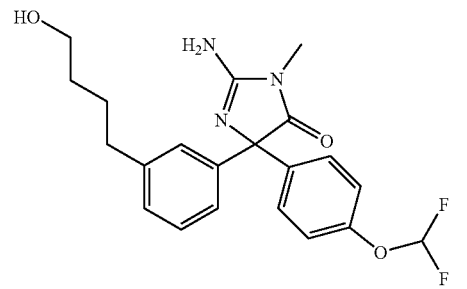

A mixture of a solution of 2-amino-5-[4-(difluoromethoxy)phenyl]-5-[3-(4-hydroxybut-1-yn-1-yl)phenyl]-3-methyl-3,5-dihydro-4H-imidazol-4-one (0.26 g, 0.65 mmol) in ethanol and 5% palladium on charcoal (26 mg) was placed on a Paar hydrogenator at 40 psi hydrogen for 8 hrs. The reaction mixture was filtered through a celite pad. The filtrate was concentrated in vacuo. The resultant residue was purified by flash chromatography on silica gel, 5% methanol/ethyl acetate as eluent, to give the title product as a white solid, 0.16 g (61% yield), mp 63-66° C.; $^1$H NMR (DMSO-d$_6$) δ 1.4 ((2H, 2H); 1.5 (m, 1 H); 2.5 (2H, under DMSO peak) 2.95 (s, 3 H); 3.3 (q, 2 H); 4.3 (t, 1 H); 6.6 (b, 2H); 7.1 (m, 3H); 7.15 (t, 2F); 7.2 (m, 3 H); 7.4 (d, 2 H); MS [(+)ESI] m/z=404 [M–H]$^+$.

EXAMPLE 22

Preparation of 2-Amino-5-[4-(difluoromethoxy)phenyl]-5-[3-(3-methoxyprop-1-yn-1-yl)-phenyl]-3-methyl-3,5-dihydro-4H-imidazol-4-one

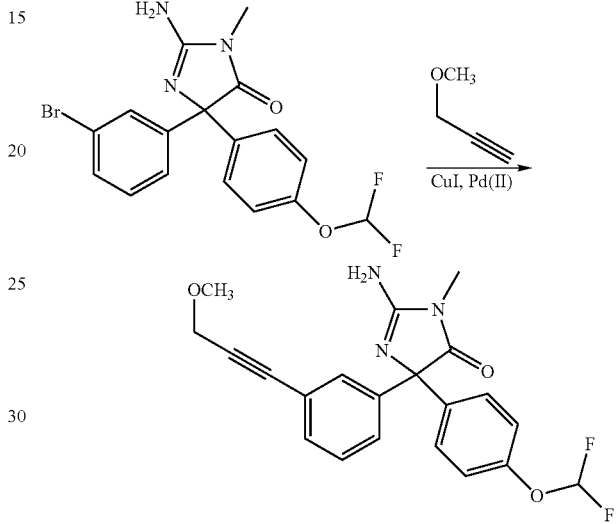

A solution of 2-amino-5-(3-bromophenyl)-5-[4-(difluoromethoxy)phenyl]-3-methyl-3,5-dihydro-4H-imidazol-4-one (0.65 g, 1.6 mmol) in pyrrolidine was treated with 3-methoxy-propyne (0.27 mL, 3.2 mmol) followed by tetrakis(triphenylphosphine) palladium(0) (90 mg, 0.08 mmole), heated to 80° C. for 4 hrs, poured into water and extracted with ethyl acetate. The extracts were combined, washed sequentially with water and brine, dried over magnesium sulfate and concentrated in vacuo. The resultant residue was purified by flash chromatography on silica gel in ethyl acetate to give the title product as a brown wax, 0.4 g (63% yield), identified by NMR and mass spectral analyses.

EXAMPLE 23

Preparation of 2-Amino-5-[4-(difluoromethoxy)phenyl]-5-{3-[(1Z)-3-methoxyprop-1-en-1-yl]phenyl}-3-methyl-3,5-dihydro-4H-imidazol-4-one

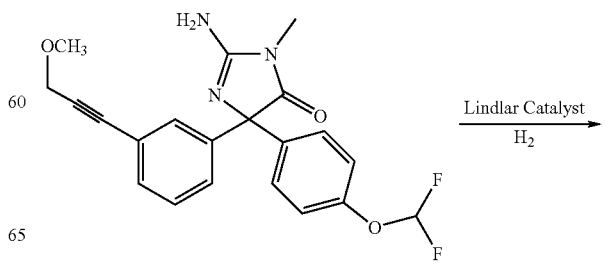

-continued

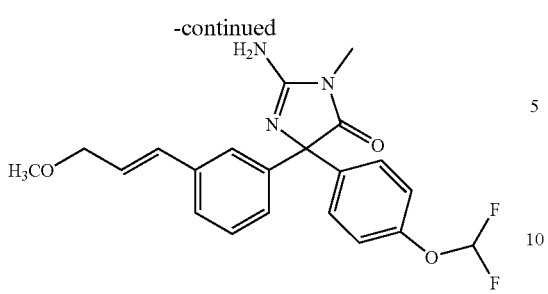

A mixture of a solution of 2-amino-5-[4-(difluoromethoxy)phenyl]-5-[3-(3-methoxyprop-1-yn-1-yl)phenyl]-3-methyl-3,5-dihydro-4H-imidazol-4-one (0.1 g, 0.25 mmol) in ethanol (1.5 mL), quinoline (1 drop) and Lindlar catalyst (24 mg. 10% mol) was placed under a hydrogen filled balloon, stirred for 16 hr filtered through celite. The filtrate was concentrated in vacuo. The resultant residue was purified by flash chromatography on silica ge,l ethyl acetate as eluent, to afford the title compound as a white solid, 0.05 g (50% yield), mp 41-44° C.; $^1$H NMR (DMSO-d$_6$) δ 2.95 (s, 3H); 3.2 (s, 3H); 4.0 (d, 2H); 5.7 (q, 1H) 6.5 (d, 1H); 6.6 (b, 2H); 7.1 (m, 3H); 7.3 (m, 4H); 7.4 (d, 2H); MS [(+)ESI] m/z=402 [M−H]$^+$.

EXAMPLE 24

Preparation of 2-Amino-5-[4-(difluoromethoxy)phenyl]-5-[3-(3-methoxypropyl)phenyl]-3-methyl-3,5-dihydro-4H-imidazol-4-one

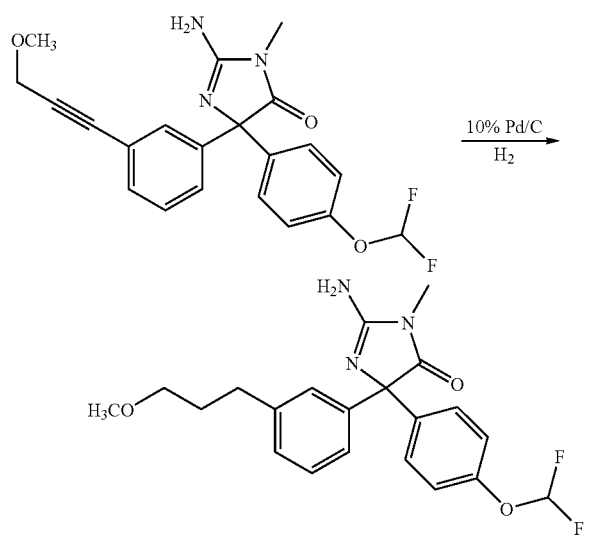

A mixture of an ethanolic solution of 2-amino-5-[4-(difluoromethoxy)phenyl]-5-[3-(3-methoxyprop-1-yn-1-yl) phenyl]-3-methyl-3,5-dihydro-4H-imidazol-4-one (0.1 g, 0.25 mmol) and 10% palladium on charcoal (10 mg) was placed under a hydrogen filled balloon for 16 h and filtered thru celite. The filtrate was concentrated to dryness in vacuo. The resultant residue was purified by flash chromatography on silica gel, ethyl acetate as eluent, to give the title product as a white solid, 0.04 g (40% yield), mp 48-50° C.; $^1$H NMR (DMSO-d$_6$) δ 2.4 (m, 2H); 2.95 (s, 3H); 3.2 (s, 3H); 3.3 (t, 2H); 6.6 (b, 2H); 7.1 (m, 3H); 7.2 (m, 4H); 7.4 (d, 2H); MS [(+)ESI] m/z=404 [M−H]$^+$.

EXAMPLE 25

Preparation of 2-Amino-5-[4-(difluoromethoxy)phenyl]-5-[3-(5-fluoropentyl)phenyl]-3-methyl-3,5-dihydro-4H-imidazol-4-one

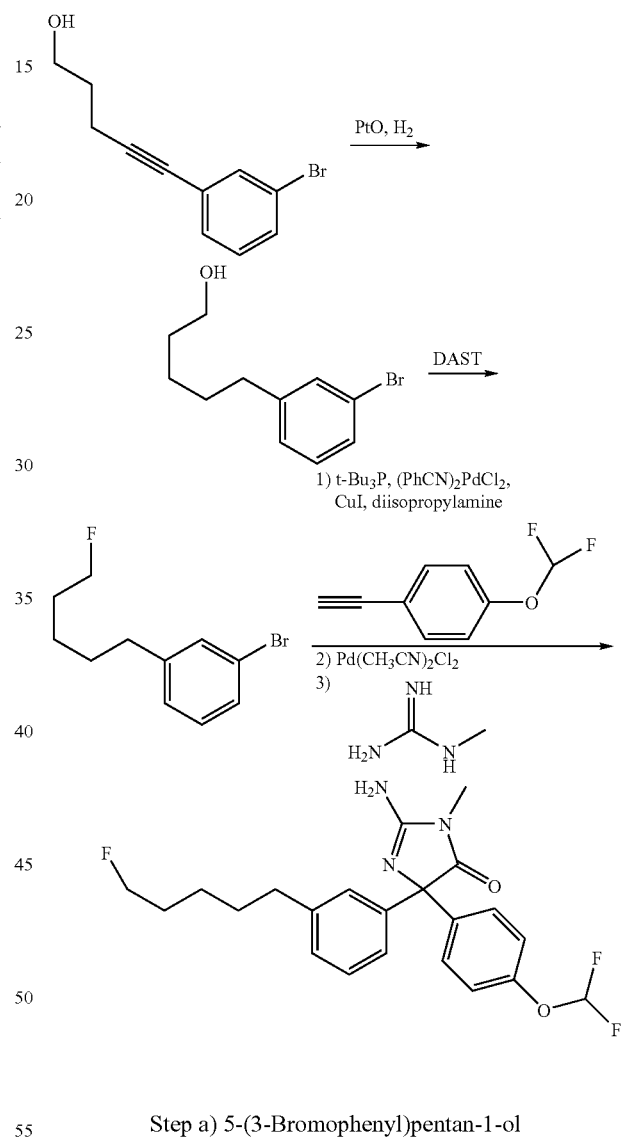

Step a) 5-(3-Bromophenyl)pentan-1-ol

A mixture of an ethanolic solution of 5-(3-Bromo-phenyl)-pent-4-yn-1-ol (Example 3, step a) (1 g, 4.2 mmol) and platinum oxide (24 mg, 10% mol) was placed on a parr shaker for 4 hrs under 40 psi of hydrogen. The reaction mixture was filtered through celite. The filtrate was concentrated in vacuo. The resultant residu was purified by flash chromatography on silica gel, 1$^{st}$ 10:1 hexane/ ethyl acetate, 2$^{nd}$ 2:1 hexane/ethyl acetate as eluent, to give 5-(3-bromophenyl)pentan-1-ol as a clear oil, 0.75 g (74% yield); $^1$H NMR (DMSO-d$_6$) δ 1.2 (m, 2H); 1.3 (m, 2H); 1.5 (m, 2 H); 3.3 (q, 2H); 4.3 (t, 1 H); 7.2 (m, 2 H); 7.4 (m, 2 H) MS [(+)ESI] m/z=243 [M−H]$^+$.

Step b) 1-Bromo-3-(5-fluoropentyl)benzene

A solution of 5-(3-bromophenyl)pentan-1-ol (0.63 g, 2.6 mmol) in methylene chloride at −78° C. was treated with a solution of diethylamino sulfur trifluoride (DAST) (0.7 mL, 5.2 mmol) in methylene chloride, allowed to warm to room temperature, stirred for 0.5 h at room temperature, poured into water and extracted with ether. The extracts were combined washed sequentially with saturated sodium bicarbonate and water, dried over magnesium sulfate and concentrated under reduced pressure. The concentrate was purified by flash chromatography on silica gel, 40:1 hexane/ethyl acetate as eluent to give 1-bromo-3-(5-fluoropentyl)benzene as a pale yellow oil, 0.4 g (63% yield); $^1$H NMR (DMSO-$d_6$) δ 1.3 (m, 2H); 1.6 (m, 4H); 2.5 (t, 2 H); 4.4 (dxt, 2H); 7.2 (m, 2 H); 7.4 (m, 2 H); MS [(+)ESI] m/z=245 [M−H]$^+$.

Step c) 2-amino-5-[4-(difluoromethoxy)phenyl]-5-[3-(5-fluoropentyl)phenyl]-3-methyl-3,5-dihydro-4H-imidazol-4-one Using essentially the same procedure described in Example 18, Steps a and c, and employing 1-bromo-3-(5-fluoropentyl)benzene and 1-difluoromethoxy-4-ethynylbenzene as reactants, the title compound was obtained as a white solid, 0.04 g (18% yield); $^1$H NMR (DMSO-$d_6$) δ 1.3 (m, 2H); 1.6 (m, 4H); 2.6 (t, 2 H); 2.95 (s, 3H); 4.4 (dxt, 2H); 6.6 (b, 2H); 7.0 (m, 3H); 7.2 (m, 4H); 7.4 (d, 2H); MS [(+)ESI] m/z 420 [M−H]$^+$.

EXAMPLE 26

Preparation of 2-Amino-5-[4-(difluoromethoxy)phenyl]-5-[3-(4-fluorobutyl)phenyl]-3-methyl-3,5-dihydro-4H-imidazol-4-one

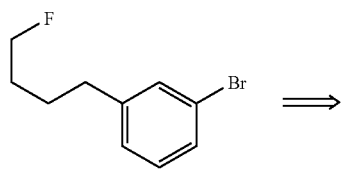

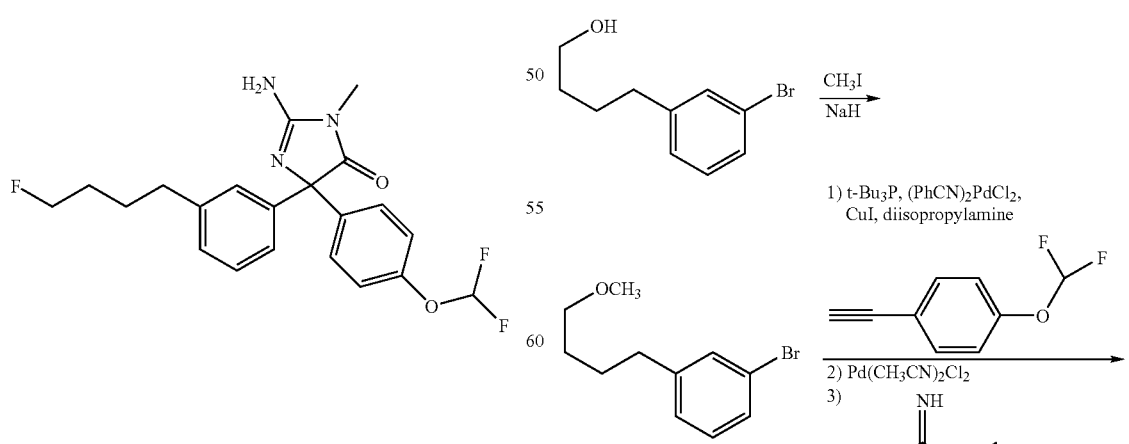

Using essentially the same procedure described in Example 25 and employing 1-bromo-3-(4-fluorobutyl)benzene, the title compound is obtained as a white solid; $^1$H NMR (DMSO-$d_6$) δ 1.6 (m, 4H); 2.5 (m, 2 H); 2.95 (s, 3H); 4.4 (dxt, 2H); 6.6 (b, 2H); 7.0 (m, 3H); 7.2 (m, 4H); 7.4 (d, 2H); MS [(+)ESI] m/z=406 [M−H]$^+$.

EXAMPLE 27

Preparation of 2-Amino-5-[4-(difluoromethoxy)phenyl]-5-[3-(6-fluorohexyl)phenyl]-3-methyl-3,5-dihydro-4H-imidazol-4-one

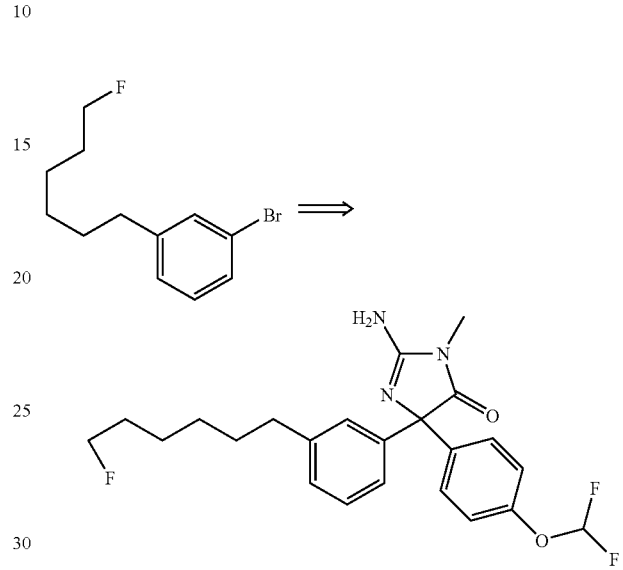

Using essentially the same procedure described in Example 25 and employing 1-bromo-3-(6-fluorohexyl)benzene, the title compound is obtained as a white solid, $^1$H NMR (DMSO-$d_6$) δ 1.3 (m, 4H); 1.6 (m, 4H); 2.5 (m, 2 H); 2.95 (s, 3H); 4.4 (dxt, 2H); 6.6 (b, 2H); 7.0 (m, 3H); 7.2 (m, 4H); 7.4 (d, 2H); MS [(+)ESI] m/z 434 [M−H]$^+$.

EXAMPLE 28

Preparation of 2-Amino-5-[4-(difluoromethoxy)phenyl]-5-[3-(6-fluorohexyl)phenyl]-3-methyl-3,5-dihydro-4H-imidazol-4-one -continued

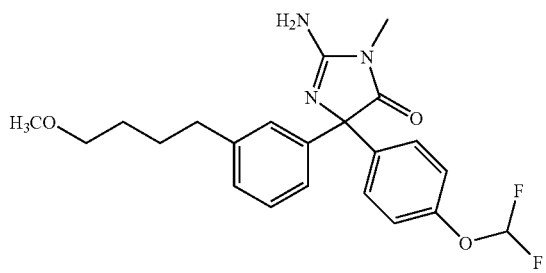

Step a) 1-bromo-3-(4-methoxybutyl)benzene

A mixture of sodium hydride [60% in oil] (130, mg, 3.3 mmol) and THF was cooled to −5° C., was treated via a syringe over a 1 min. period with a solution of 4-(3-romophenyl)butan-1-ol (0.7 g, 3.0 mmol) in THF, warmed to room temperature and stirred at room temperature for 0.5 h, treated with methyl iodide (4.6 g, 35 mmol), stirred for 2 h, poured into saturated ammonium chloride and extracted with ether. The extracts were combined, washed with brine, dried over magnesium sulfate adn concentrated in vacuo. The resultant residue was purified by flash chromatography on silica gel, 40:1 hexane/ethyl acetate as eluent, to afford 1-bromo-3-(4-methoxybutyl)benzene as a clear oil, 0.38 g (51% yield); $^1$H NMR (DMSO-$d_6$) δ 1.4 (m, 2H); 1.5 (m, 2H); 2.5 (t, 2 H); 3.2 (s, 3H); 3.3 (t, 2H); 7.2 (m, 2H); 7.4 (m, 2H); MS [(+)ESI] m/z=244 [M−H]$^+$.

Step b) 2-amino-5-[4-(difluoromethoxy)phenyl]-5-[3-(4-methoxybutyl)phenyl]-3-methyl-3,5-dihydro-4H-imidazol-4-one Using essentially the same procedure described in Example 18, Steps a and c, and employing 1-bromo-3-(4-methoxybutyl)benzene and 1-difluoromethoxy-4-ethynylbenzene as reactants, the title compound was obtained as a white solid, mp 36-39° C.; $^1$H NMR (DMSO-$d_6$) δ 1.4 (m, 4H); 2.5 (m, 2 H); 2.95 (s, 3H); 3.2 (s, 3H); 3.3 (t, 2H); 6.6 (b, 2H); 7.0 (m, 3H); 7.2 (m, 4H); 7.4 (d, 2H); MS [(+)ESI] m/z 418 [M−H]$^+$.

EXAMPLE 29

Preparation of 3-{2-Amino-4-[4-(difluoromethoxy) phenyl]-1-methyl-5-oxo-4,5-dihydro-1H-imidazol-4-yl}-N-propylbenzamide

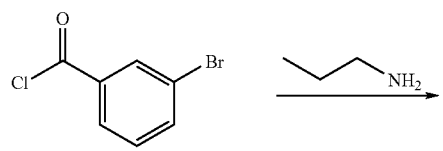

-continued
1) t-Bu$_3$P, (PhCN)$_2$PdCl$_2$, CuI, diisopropylamine

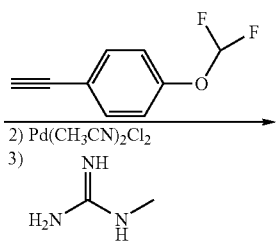

2) Pd(CH$_3$CN)$_2$Cl$_2$
3)

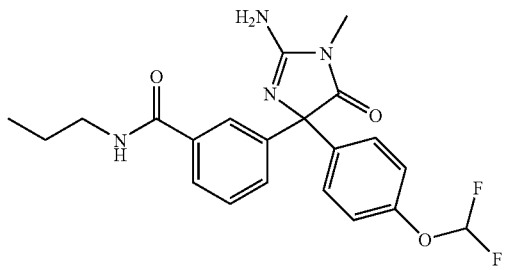

Step a) 3-Bromo-N-propyl-benzamide

A mixture of N-propyl amine (0.33 mL, 4.1 mmol) and triethylamine (0.83 mL, 5.8 mmol) in methylene chloride was cooled to −5° C., treated with 3-bromobenzoyl chloride (1 g, 4.5 mmol), warmed to room temperature, stirred at room temperature for 1 h, poured into aqueous sodium bicarbonate and extracted with methylene chloride. The extracts were combined, washed sequentially with water and brine, dried over magnesium sulfate and concentrated under reduced pressure. The resultant residue was purified by flash chromatography on silica gel, 2:1 hexane/ethyl acetate as eluent, to give 3-bromo-N-propyl-benzamide as a white solid, 0.74 g (67% yield); $^1$H NMR (DMSO-$d_6$) δ 0.8 (t, 3H); 1.5 (m, 2H); 3.2 (t, 2H); 7.4 (t, 1H); 7.6 (d, 1H), 7.8 (d, 1H); 7.9 (s, 1H); 8.5 (b, 1H); MS [(+)ESI] m/z 242[M−H]$^+$.

Step b) 3-{2-amino-4-[4-(difluoromethoxy)phenyl]-1-methyl-5-oxo-4,5-dihydro-1H-imidazol-4-yl}-N-propylbenzamide Using essentially the same procedure described in Example 18, Steps a and c, and employing 3-bromo-N-propyl-benzamide and 1-difluoromethoxy-4-ethynylbenzene as reactants, the title compound was obtained as a white solid, mp 93-96° C. $^1$H NMR (DMSO-$d_6$) δ 0.8 (t, 3H); 1.4 (m, 2H); 2.95 (s, 3H); 3.2 (t, 2H); 6.7 (b, 2H); 7.1 (d, 2H); 7.3 (m, 1H); 7.4 (d, 2H); 7.5 (d, 1H); 7.6 (d, 1H), 7.7 (s, 1H); 8.4 (b, 1H); MS [(+)ESI] m/z 417 [M−H]$^+$.

EXAMPLE 30

Preparation 2-Amino-5-[4-(difluoromethoxy)phenyl]-5-{3-[(2-fluoroethoxy)methyl]phenyl}-3-methyl-3,5-dihydro-4H-imidazol-4-one

EXAMPLES 31-39

Preparation 2-Amino-5-[4-(difluoromethoxy)phenyl]-5-[3-(alkoxymethyl)phenyl]-3-methyl-3,5-dihydro-4H-imidazol-4-one

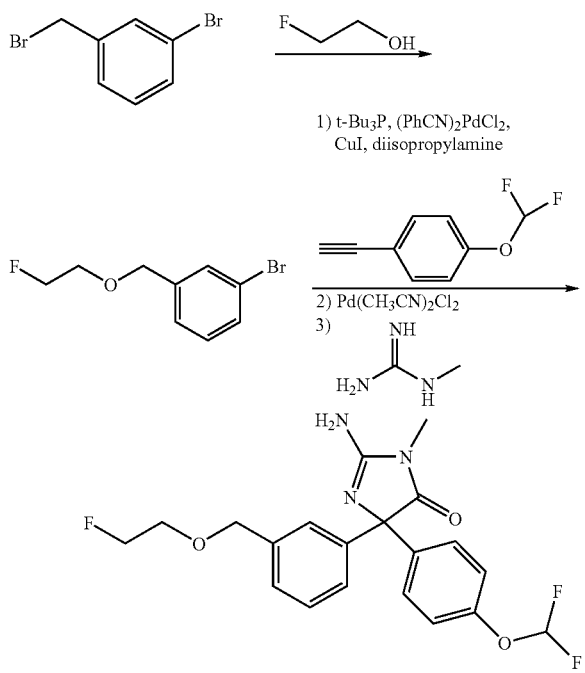

Step a) 1-Bromo-3-(2-fluoroethoxymethyl)benzene

A mixture of sodium hydride [60% in oil] (343, mg, 8.6 mmol) and THF at −5° C. was treated via a syringe with a solution of 2-fluoroethanol in THF over a 1 min. period, stirred for 2 min., warmed to room temperature, stirred for 15 min. at room temperature, treated with 3-bromobenzylbromide (2.5 g, 11.7 mmol), stirred for 1 h, poured into saturated ammonium chloride and extracted with ether. The extracts were combined, washed sequentially with water and brine, dried over magnesium sulfate and concentrated under reduced pressure. The residue was purified by flash chromatography on silica gel, 20:1 hexane/ ethyl acetate as eluent, to afford 1-bromo-3-(2-fluoroethoxymethyl)benzene as a yellow oil, 1 g (58% yield), $^1$H NMR (DMSO-d$_6$) δ 3.6 (dxt, 2H); 4.5 (dxt, 2H); 4.4 (s, 2 H); 7.3 (m, 2H); 7.5 (m, 2H); MS [(+)ESI] m/z 219 [M−H]$^+$.

Step b) 2-Amino-5-[4-(difluoromethoxy)phenyl]-5-{3-[(2-fluoroethoxy)methyl]-phenyl}-3-methyl-3,5-dihydro-4H-imidazol-4-one Using essentially the same procedure described in Example 18, Steps a and c, and employing 1-bromo-3-(2-fluoroethoxymethyl)benzene and 1-difluoromethoxy-4-ethynylbenzene as reactants, the title compound was obtained as a white solid, mp 40-43° C.; $^1$H NMR (DMSO-d$_6$) δ 2.95 (s, 3H); 3.6 (dxt, 2H); 4.4 (m, 3H); 4.6 (t, 1H); 6.7 (b, 2H); 7.1 (d, 2H); 7.2 (m, 1H); 7.3 (m, 1H); 7.4 (m, 1H); 7.5 (m, 3H); MS [(+)ESI] m/z 408 [M−H]$^+$.

Using essentially the same procedure described in Example 30 and employing the desired alcohol in Step a, the compounds shown on Table I were obtained and identified by NMR and mass spectral analyses.

TABLE I

| Ex. No. | R | mp ° C. | [M + H]$^+$ |
|---|---|---|---|
| 31 | CH$_2$CH$_2$CF$_3$ | 46-48 | 458 |
| 32 | CH$_3$ | 70-72 | 376 |
| 33 | CH$_2$CH$_2$CH$_2$CH$_3$ | 37-39 | 418 |
| 34 | CH$_2$-cyclopropyl | 47-50 | 416 |
| 35 | CH$_2$CH$_3$ | 45-48 | 390 |
| 36 | CH$_2$CH$_2$CH$_3$ | 40-43 | 404 |
| 37 | CH(CH$_2$F)CH$_2$F | 46-50 | 440 |
| 38 | CH$_2$CF$_3$ | 50-52 | 441 |
| 39 | CH$_2$CF$_2$CHF$_2$ | 48-50 | 476 |

EXAMPLE 40

Preparation of 2-Amino-5-[4-(difluoromethoxy)phenyl]-5-{3-[(1E)-6-methoxy-hex-1-en-1-yl]-phenyl}-3-methyl-3,5-dihydro-4H-imidazol-4-one

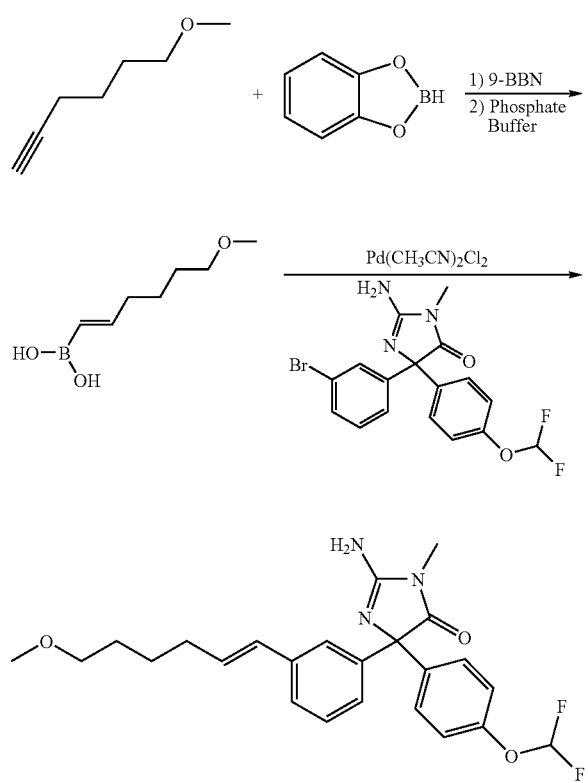

Step a) (E)-6-Methoxy-hex-1-enylboronic acid

A mixture of methylhexynyl ether (7.2 mmol), 9-BBN 0.5M in THF (1.8 ml, 0.9 mmol) and catecholborane (1.21 g, 10.1 mmol) is heated in a pressure tube at 100° C. for 16 h, quenched with pH 7 phosphate buffer, stirred for 2 h, and extracted with ether. The combined extracts are dried over $MgSO_4$ and concentrated in vacuo. The resultant residue is purified by flash chromatography to obtain (E)-6-methoxy-hex-1-enylboronic acid, identified by NMR and mass spectral analyses. ($^1$H-NMR 300 MHz, CDCl3+D2O): 6.52 (dt, 1H); 5.44 (dt, 1H); 3.40 (t, 2H); 3.35 (s, 3H); 2.21 (ddt, 2H); 1.68-1.45 (m, 4H).

Step b) 2-Amino-5-[4-(difluoromethoxy)phenyl]-5-{3-[(1E)-6-methoxy-hex-1-en-1-yl]-phenyl}-3-methyl-3,5-dihydro-4H-imidazol-4-one A degassed solution of 2-amino-5-(3-bromophenyl)-5-[4-(difluoromethoxy)phenyl]-3-methyl-3,5-dihydro-4H-imidazol-4-one (200 mg, 0.488 mmol) and (E)-6-methoxy-hex-1-enylboronic acid (0.537 mmol) in 1 ml of 2 M $K_2CO_3$ and 2.5 ml of DME is treated with $Pd(CH_3CN)_2Cl_2$ (20 mg, 5%), the mixture heated at 95° C. under a nitrogen atmosphere for 16 h, diluted with water and extracted with $CH_2Cl_2$. The extracts are combined, dried over $MgSO_4$ and concentrated in vacuo. The resultant residue is purified on a silica gel cartridge and then by preparative HPLC to afford the title compound, 121 mg (56% yield), identified by NMR and mass spectral analyses. ($^1$H-NMR 300 MHz, CDCl3): 7.49 (d, 2H); 7.42 (s br, 1H); 7.27 (m, 5H); 7.06 (d, 2H); 6.49 (dd, 1H); 6.36 (d, 1H); 6.20 (dt, 1H); 3.41 (t, 2H); 3.35 (s, 3H); 3.12 (s, 3H); 2.22 (dt, 2H); 1.69-1.47 (m, 4H). MS [M+H]$^+$ 444.4

EXAMPLE 41

Preparation of 2-Amino-5-[4-(difluoromethoxy)phenyl]-5-{3-[(1E)-5-hydroxy-pent-1-en-1-yl]-phenyl}-3-methyl-3,5-dihydro-4H-imidazol-4-one

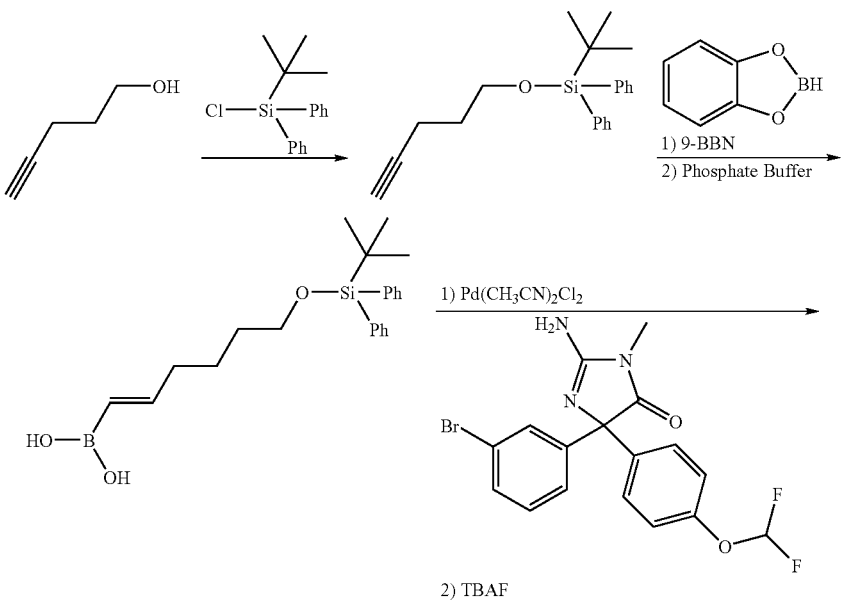

-continued

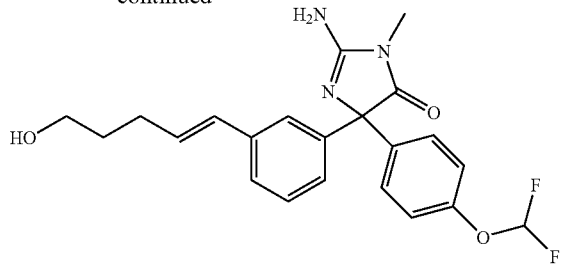

Step a) t-Butylpent-4-ynyloxy diphenyl silane

A mixture of pentynol (8.0 g, 95 mmol), t-butyldiphenyl-silylchloride (28 g, 114 mmol) and Et$_3$N (14 g, 138 mmol) in CH$_2$Cl$_2$ is stirred at room temperature for 16 h, treated with 1M K$_2$CO$_3$ and extracted with CH$_2$Cl$_2$. The combined extracts are dried over MgSO$_4$ and concentrated in vacuo. The residue is purified by filtration on a silica pad to obtain 30 g of t-butylpent-4-ynyloxy diphenyl silane (yield: 98%

Step b) 2-Amino-5-[4-(difluoromethoxy)phenyl]-5-{3-[(1E)-5-hydroxy-pent-1-en-1-yl]-phenyl}-3-methyl-3,5-dihydro-4H-imidazol-4-one Using essentially the same procedure described in Example 40 and employing t-butylpent-4-ynyloxy diphenyl silane, the silyl ether of the title compound is obtained. A solution of the silyl ether (635 mg, 0.97 mmol) in THF is treated with 1M TBAF in THF (1 ml, 1 mmol), stirred for 16 h, diluted with water and extracted with CH$_2$Cl$_2$. The combined extracts are dried over MgSO$_4$ and concentrated in vacuo. The resultant residue is purified by a silica cartridge, by preparative HPLC and by SCX cartridge (to eliminate all residual TBAF) to afford the title product as a white solid, 59 mg (15% yield), identified by NMR and mass spectral analyses. ($^1$H-NMR 300 MHz, DMSO): 7.47(d, 2H); 7.34-7.14(m, 4H); 7.16(t, 1H); 7.11(d, 2H); 6.68(s br, 2H); 6.35(d, 1H); 6.19(dt, 1H); 4.40(t, 1H); 3.42(dt, 2H); 2.98(s, 3H); 2.19(m, 2H); 1.57(m, 2H). MS [M+H]$^+$ 416.1.

EXAMPLES 42-49

Preparation of 2-Amino-5-[4-(difluoromethoxy)phenyl]-5-(3-alkenylphenyl)-3-methyl-3,5-dihydro-4H-imidazol-4-one Compounds

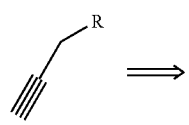 ⟹

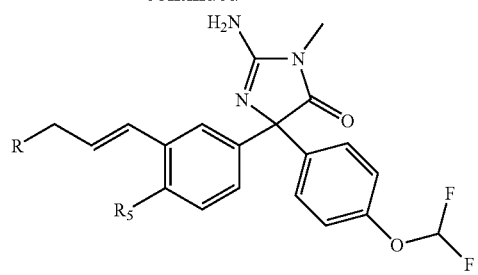

Using essentially the same procedures described in Examples 40 and 41 and employing the desired alkyne in Step a, the compounds shown on Table II were obtained and identified by NMR and mass spectral analyses.

TABLE II

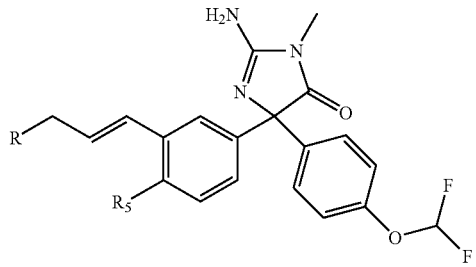

| Ex. No. | R | R5 | [M + H]$^+$ |
|---|---|---|---|
| 42 | CH$_2$CH$_2$OCH$_3$ | H | 430.2 |
| 43 | OCH$_3$ | H | 402.1 |
| 44 | CH$_2$OCH$_3$ | H | 416.1 |
| 45 | CH$_2$OH | H | 402.1 |
| 46 | CH$_2$F | H | 404.1 |
| 47 | CH$_2$CH$_2$F | H | 408.1 |
| 48 | CH$_2$F | F | 422.01 |
| 49 | CHF$_2$ | H | 422.1 |

EXAMPLE 50

Preparation of 2-Amino-5-[4-(difluoromethoxy)phenyl]-5-{3-[2-(methoxymethyl)cyclopropyl]phenyl}-3-methyl-3,5-dihydro-4H-imidazol-4-one

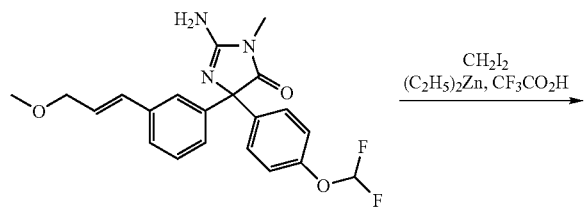

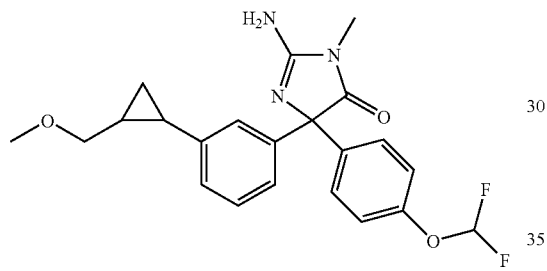

A 1M solution of diethyl zinc (4.92 ml, 4.92 mmol) in dry $CH_2Cl_2$ at 0° C. is treated very slowly with a solution of $CF_3CO_2H$ (0.56 g, 4.92 mmol) in dry $CH_2Cl_2$, stirred for 20 min, treated dropwise with a solution of $CH_2I_2$ (0.66 g, 2.46 mmol) in dry $CH_2Cl_2$, stirred for 20 min, treated with a solution of 2-amino-5-[4-(difluoromethoxy)phenyl]-5-{3-[(1E)-3-methoxyprop-1-en-1-yl]phenyl}-3-methyl-3,5-dihydro-4H-imidazol-4-one (197 mg, 0.492 mmol) in dry $CH_2Cl_2$, allowed to come to room temperature, stirred for 2 h at room temperature, quenched with aqueous $NH_4Cl$ and extracted with $CH_2Cl_2$. The combined extracts are dried over $MgSO_4$ and concentrated in vacuo. The resultant residue is purified by SCX cartridge and preparative HPLC to give the title compound as a white solid, 32 mg (16% yield), identified by NMR and mass spectral analyses. ($^1$H-NMR 300 MHz, DMSO): 7.46(d, 2H); 7.24-7.13(m, 3H); 7.16(t, 1H); 7.10(d, 2H); 6.88(m, 1H); 6.64(s br, 2H); 3.44-3.34(m, 2H); 3.24(m, 1H); 3.23(s, 3H); 2.97(s, 3H); 1.76(m, 1H); 0.90-0.76(m, 2H). MS [M+H]$^+$ 416.1

EXAMPLE 51

Preparation of 2-Amino-5-[4-(difluoromethoxy)phenyl]-5-{3-[2-(2-methoxyethyl)cyclopropyl]phenyl}-3-methyl-3,5-dihydro-4H-imidazol-4-one

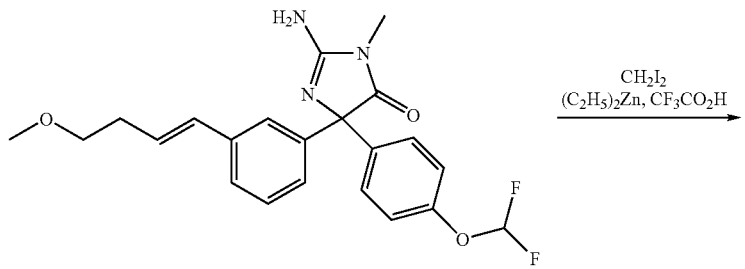

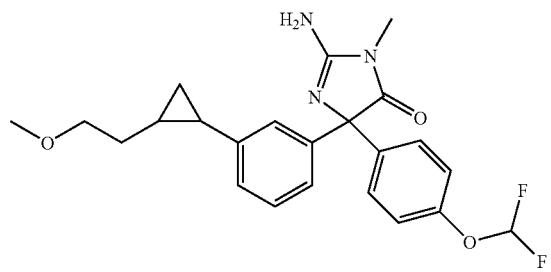

Using essentially the same procedure described in Example 50 and employing 2-amino-5-[4-(difluoromethoxy)-phenyl]-5-{3-[(1E)-4-methoxybut-1-en-1-yl]phenyl}-3-methyl-3,5-dihydro-4H-imidazol-4-one as starting material, the title product is obtained as a white solid and identified by NMR and mass spectral analyses. ¹HNMR: (DMSO d₆) δ 7.46(d, 2H); 7.22-7.13(m, 3H); 7.16(dd, 1H); 7.10(d, 2H); 6.87(d br, 1H); 6.64(s br, 2H); 3.38(t, 2H); 3.22 (s, 3H); 2.98(s, 3H); 1.68-1.45(m, 3H); 0.97(m, 1H); 0.76(m, 2H). MS [M+H]⁺ 430.1

EXAMPLE 52

Preparation of 5-(3-Acetylphenyl)-2-amino-5-[4-(difluoromethoxy)phenyl]-3-methyl-3,5-dihydro-4H-imidazol-4-one

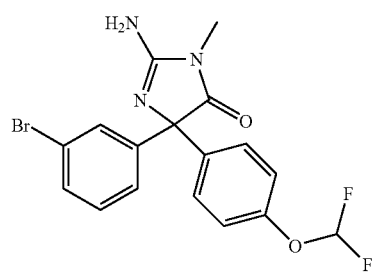

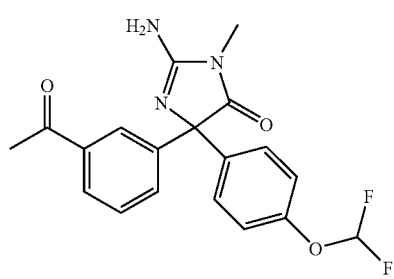

A mixture of 2-amino-5-(3-bromophenyl)-5-[4-(difluoromethoxy)phenyl]-3-methyl-3,5-dihydro-4H-imidazol-4-one (1.50 g, 3.66mmol), 1,3-bis(diphenylphosphino)propane (DPPP) (0.377 g, 0.915 mmol), K₂CO₃ (0.606 g, 4.39 mmol), Pd(OAc)₂ (82 mg, 0.37 mmol) and n-butylvinylether (1.47 g, 14.6 mmol) in DMF/water (8 ml/0.8 ml) is heated in a microwave oven for 1 h at 120° C., cooled to room temperature, treated cautiously with 15 ml of 5% HCl, stirred at room temperature for 1 h, diluted with water, basified with aqueous K₂CO₃ and extracted with ethyl acetate. The extracts are combined, dried over MgSO4 and concentrated in vacuo to give a residue. The residue is purified by SCX cartridge to give the title compound, 1.20 g (88% yield), identified by NMR and mass spectral analyses. ¹H NMR (300 MHz, CDCl₃) ppm 8.11 (t, 1 H), 7.87 (dt, 1 H), 7.72-7.80 (m, 1 H), 7.52 (d, 2 H), 7.44 (t, 1 H), 7.08 (d, 2 H), 6.49 (t, 1 H), 3.15 (s, 3 H), 2.59 (s, 3 H). MS [M+H]⁺ 374.1.

EXAMPLE 53

Preparation of 2-Amino-5-[4-(difluoromethoxy)phenyl]-5-[3-(3-hydroxyhex-4-yn-1-yl)phenyl]-3-methyl-3,5-dihydro-4H-imidazol-4-one

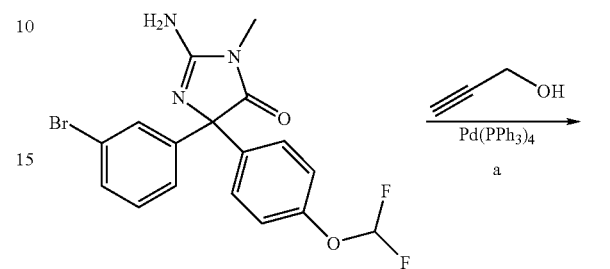

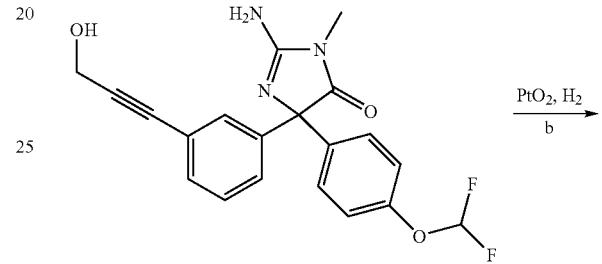

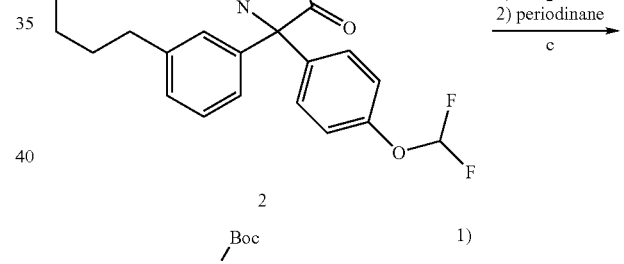

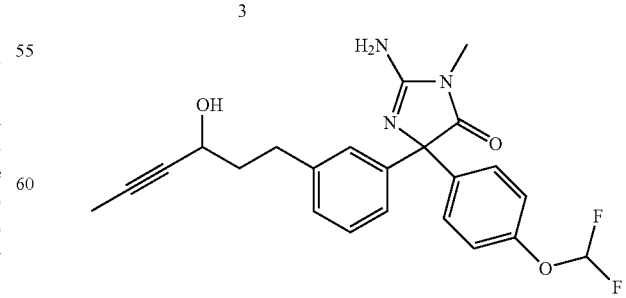

Step a) 2-Amino-5-[4-(difluoromethoxy)phenyl]-5-[3-(3-hydroxyprop-1-yn-1-yl)phenyl]-3-methyl-3,5-dihydro-4H-imidazol-4-one (1)

A mixture of 2-amino-5-(3-bromophenyl)-5-[4-(difluoromethoxy)phenyl]-3-methyl-3,5-dihydro-4H-imidazol-4-one (2.4 g, 5.85 mmol), 3-hydroxy-1-propyne (3.27 g, 58.5 mmol) and Pd(PPh$_3$)$_4$ (670 mg, 0.585 mmol) in pyrrolidine is heated at 70° C. under a nitrogen atmosphere for 16 h, diluted with water and extracted with CH$_2$Cl$_2$. The extracts are combined, dried over MgSO$_4$ and concentrated in vacuo to give a residue. The residue is purified by chromatography on a silica cartridge, to give 2-amino-5-[4-(difluoromethoxy)phenyl]-5-[3-(3-hydroxyprop-1-yn-1-yl)phenyl]-3-methyl-3,5-dihydro-4H-imidazol-4-one, 1 g (45% yield), identified by NMR and mass spectral analyses.

Step b) 2-Amino-5-[4-(difluoromethoxy)phenyl]-5-[3-(3-hydroxypropyl)phenyl]-3-methyl-3,5-dihydro-4H-imidazol-4-one (2)

A mixture of an ethanolic solution of 1 (1 g, 2.6 mmol) and PtO$_2$ (50 mg, 10%) is hydrogenated at 15 psi on a Parr hydrogenator for 4 h and filtered through celite. The filtrate is concentrated to dryness under reduced pressure to afford 2-amino-5-[4-(difluoromethoxy)phenyl]-5-[3-(3-hydroxypropyl)phenyl]-3-methyl-3,5-dihydro-4H-imidazol-4-one, 830 mg, identified by NMR and mass spectral analyses.

Step c) Compound 3

A solution of 2 (480 mg) in THF under nitrogen is treated with DMAP (150 mg, 1.23 mmol) and Boc$_2$O (938 mg, 4.3 mmol), stirred for 2 h, diluted with water and extracted CH$_2$Cl$_2$. The extracts are combined, dried over MgSO$_4$ and concentrated in vacuo to give a residue. The residue is dissolved in 10 ml of MeOH and 30% aqueous NaOH (400 µl, 3 eq), stirred for 16 h at room temperature, diluted with brine and extracted with CH$_2$Cl$_2$. The extracts are combined, dried over MgSO$_4$ and concentrated in vacuo to give a residue. Purification of this residue by flash chromatography affords the protected 2-amino-5-[4-(difluoromethoxy)phenyl]-5-[3-(3-hydroxypropyl)phenyl]-3-methyl-3,5-dihydro-4H-imidazol-4-one compound, 265 mg (yield: 44%). This compound (265 mg, 0.542 mmol) is dissolved in dry CH$_2$Cl$_2$, treated with Dess-Martin's periodinane (276 mg, 0.650 mmol), stirred for 2 h, washed with water and brine, dried over MgSO$_4$ and evaporated to dryness. The resultant residue is purified on a silica cartridge to afford compound 3, 170 mg (yield: 64%), identified by NMR and mass spectral analyses.

Step d) 2-Amino-5-[4-(difluoromethoxy)phenyl]-5-[3-(3-hydroxyhex-4-yn-1-yl)phenyl]-3-methyl-3,5-dihydro-4H-imidazol-4-one A solution of 3 (80 mg, 0.164 mmol) in dry THF under nitrogen at –70° C. is treated with the Grignard reagent 4 (656 µl, 0.328 mmol), allowed to come to room temperature, stirred for 2 h at room temperature, diluted with water and extracted with CH$_2$Cl$_2$. The extracts are combined, dried over MgSO$_4$ and concentrated in vacuo to give a residue. This residue (50 mg) is dispersed in CH$_2$Cl$_2$, treated with trifluoroacetic acid (215 mg, 1.9 mmol), stirred for 16 h, washed with aqueous K$_2$CO$_3$, dried over MgSO$_4$ and evaporated under reduced pressure. The resultant residue is purified by preparative HPLC to give the title product, 15 mg, identified by NMR and mass spectral analyses. $^1$H NMR (1H DMSO): 7.44(d, 2H); 7.29-7.07(m, 6H); 7.19(dd, 1H); 5.20(d, 1H); 4.13(m, 1H); 3.03(s, 3H); 2.62(m, 2H); 1.79(d, 3H); 1.74(m, 2H). MS [M+H]$^+$ 428.1.

EXAMPLE 54

Preparation of 2-Amino-5-[4-(difluoromethoxy)phenyl]-5-[3-(3-fluoroprop-1-yn-1-yl)phenyl]-3-methyl-3,5-dihydro-4H-imidazol-4-one

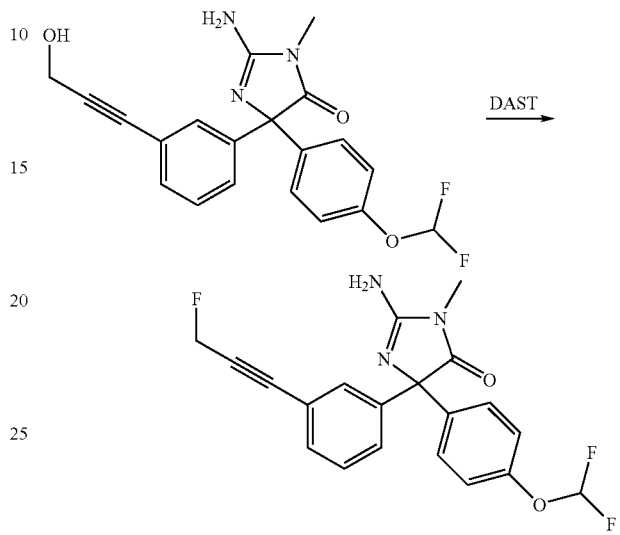

A solution of 2-mino-5-[4-(difluoromethoxy)phenyl]-5-[3-(3-hydroxyprop-1-yn-1-yl)phenyl]-3-methyl-3,5-dihydro-4H-imidazol-4-one (300 mg, 0.779 mmol) in dry CH$_2$Cl$_2$ under nitrogen at –40° C. was treated dropwise with DAST (252 mg, 1.56 mmol), stirred at –40° C. for 1 h, allowed to warm to room temperature, stirred at room temperature for 16 h; diluted with water, stirred for 30 min. and extracted with CH$_2$Cl$_2$. The extracts are combined, dried over MgSO4 and concentrated in vacuo to give a residue. The residue is repeatedly purified by preparative HPLC to afford the title product, 23 mg (8% yield), LC-MS purity: 98%), identified by NMR and mass spectral analyses. 1H NMR (300 MHz, CDCl$_3$) ppm 7.60 (s, 1 H), 7.47 (s, 3 H), 7.32-7.38 (m, 1 H), 7.22-7.28 (m, 1 H), 7.04 (d, 2 H), 6.47 (t, 1H), 5.14 (d, 2 H), 3.10 (s, 3 H). MS [M+H]$^+$ 388.1.

EXAMPLES 55-57

Preparation of 2-Amino-5-[4-(difluoromethoxy)phenyl]-5-[3-(3-substituted)phenyl]-3-methyl-3,5-dihydro-4H-imidazol-4-one Compounds

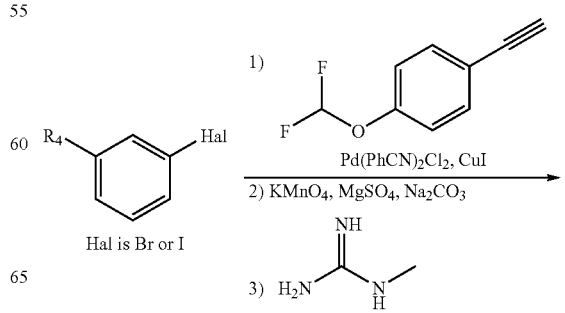

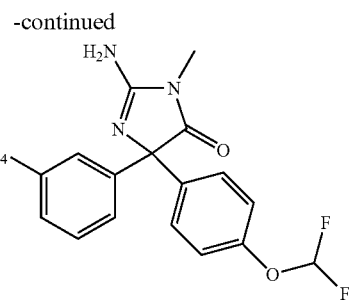

Using essentially the same procedures described in Example 14, Steps f, g and h, and employing the desired halobenzene, the compounds shown in Table III were obtained and identified by NMR and mass spectral analyses.

TABLE III

| Ex. No. | R4 | mp ° C. | [M + H]+ |
|---|---|---|---|
| 55 | $CH_2CH_2F$ | 60-63 | 378 |
| 56 | $COCH_2CH_2CH_2CH_2F$ | — | 434 |
| 57 | $COCH_2CH_2CH_2F$ | 78-82 | 420 |

EXAMPLE 58

Preparation of 2-Amino-5-[4-(difluoromethoxy)phenyl]-5-(3hydroxyphenyl)-3-methyl-3,5-dihydro-4H-imidazol-4-one

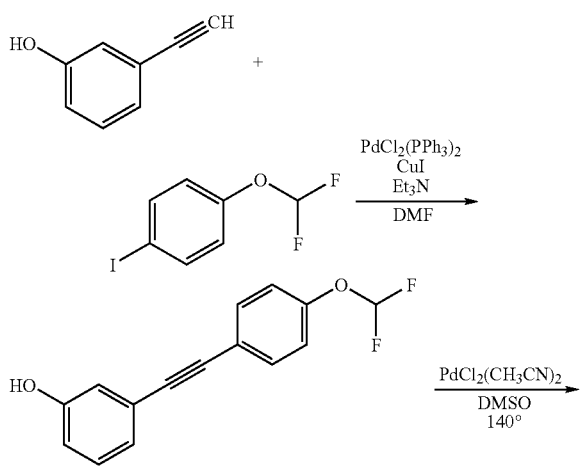

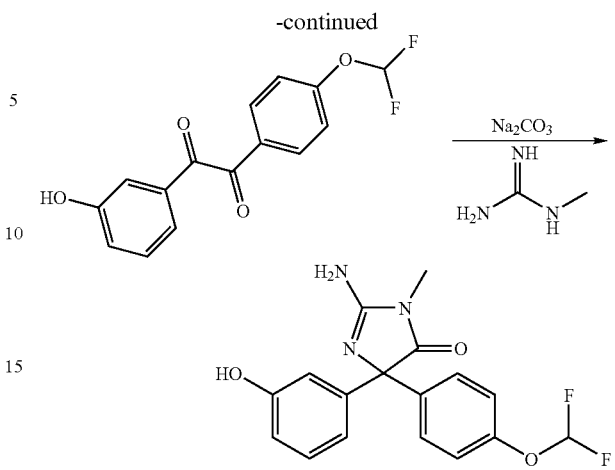

Step a) 3-((4-(Difluoromethoxy)phenyl)ethynyl)phenol

A solution of 4-(difluoromethoxy)phenyl iodide (4.70 g) in deoxygenated dimethylformamide was treated with trans-dichlorobis(triphenylphosphine) palladium(II) (244 mg) and copper(II) iodide 66 mg) followed by triethylamine (7.52 mL), stirred under a nitrogen atmosphere for 5min., treated with 3-hydroxyphenyl acetylene (2.467 g), stirred under nitrogen atmosphere for 16 h, poured into ethyl acetate and was washed with 0.05 N HCl and water. The organic phase was dried over $MgSO_4$ and concentrated in vacuo. The residue was chromatographed, silica gel, 40% ethyl acetate/hexane as eluent, to afford 3-((4-(difluoromethoxy)phenyl)ethynyl)phenol as a tan solid, 5.40 g; $^1$H NMR (DMSO-d6): δ 9.64 (s, 1H), 7.56 (d, J=8.8 Hz, 2H), 7.27 (t, J=73.7 Hz, 1H), 7.17 (d, J=8.8 Hz, 2H), 7.16 (m, 1H), 6.94 (m, 1H), 6.86 (m, 1H), and 6.77 (m, 1H); MS (ES neg) m/z 260.

Step b) 1-(4-(Difluoromethoxy)phenyl)-2-(3-hydroxyphenyl)ethane-1,2-dione

A mixture of 3-((4-(difluoromethoxy)phenyl)ethynyl)phenol (5.0 g) and dichlorobis(acetonitrile)palladium (II) (0.50 g) and dimethylsulfoxide was heated at 140° for 4 h, cooled to room temperature, poured into water, stirred well for 10 min. and extracted with chloroform. The combined extracts were dried over $MgSO_4$ and evaporated to a dark oil. The oil was purified by flash chromatography (silica gel) using step gradient elution (10% ethyl acetate/hexane to 20% ethyl acetate/hexane to give 1-(4-(difluoromethoxy)phenyl)-2-(3-hydroxyphenyl)ethane-1,2-dione as a light yellow waxy solid, 2.75 g; $^1$H NMR (DMSO-d6): δ 10.02 (s, 1H), 7.95 (d, J=8.9 Hz, 2H), 7.41 (t, J=73.0 Hz, 1H), 7.38 (m, 1H), 7.34 (d, J=8.9 Hz, 2H), 7.25 (m, 2H), and 7.12 (m, 1H); MS (ES neg) m/z 292.

Step c) 2-Amino-5-[4-(difluoromethoxy)phenyl]-5-(3-hydroxyphenyl)-3-methyl-3,5-dihydro-4H-imidazol-4-one A mixture of 1-(4-(difluoromethoxy)phenyl)-2-(3-hydroxyphenyl)ethane-1,2-dione (2.75 g), N-methylguanidine hydrochloride (1.237 g) and sodium carbonate (2.20 g) in ethanol was heated at 85° C. for 8 h, cooled to room temperature and evaporated in vacuo. The resultant residue was partitioned between water and chloroform. The organic phase was separated, dried over $Na_2SO_4$ and evaporated to a light brown oil. The oil was purified by flash chromatography (silica gel) using step gradient elution (100% chloroform to 15% methanol/chloroform) to afford the title compound as a white foamy glass, 2.20 g; $^1$H NMR (DMSO-d6): δ 9.24 (bs, 1H), 7.42 (d, J=8.8 Hz, 2H), 7.12 (t, J=74.3 Hz, 1H), 7.06 (d, J=8.8 Hz, 2H), 7.02 (m, 1H), 6.80 (m, 2H), 6.57 (bs, 2H), and 6.56 (m, 1H); MS (APPI) m/z 348.

EXAMPLE 59

Preparation of 2-Amino-5-[4-(difluoromethoxy)phenyl]-5-[3-(3-fluoropropox-1-yl)phenyl]-3-methyl-3,5-dihydro-4H-imidazol-4-one

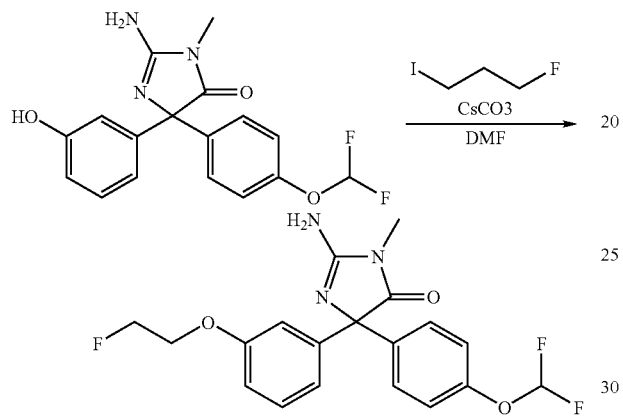

A mixture of 2-amino-5-[4-(difluoromethoxy)phenyl]-5-(3-hydroxyphenyl)-3-methyl-3,5-dihydro-4H-imidazol-4-one (197 mg), 1-iodo-3-fluoropropane (127 mg), and cesium carbonate (240 mg) in dry DMF was stirred at room temperature under nitrogen atmosphere for 16 h, diluted with chloroform, stirred for 5 min. and filtered through a glass fibre 3.1 μm syringe filter. The filtrate was evaporated, The resultant residue was purified by HPLC; CN bonded phase prep column, gradient elution (80% A/20% B to 20% A/80% B, A=hexane; B=(20% methanol/80% dichloromethane) to afford a clear oil. The oil was crystallized from warm ethyl acetate/hexane to give the title compound as white crystals, mp 161-162° C.; identified by NMR and mass spectral analyses. MS (APPI) m/z 408;

EXAMPLE 60

Preparation of 2-Amino-5-[4-(difluoromethoxy)phenyl]-5-(4-fluoro-3-hydroxyphenyl)-3-methyl-3,5-dihydro-4H-imidazol-4-one

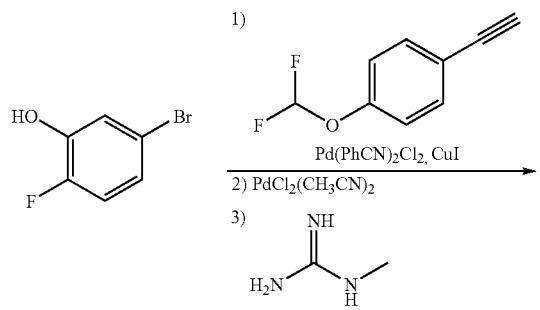

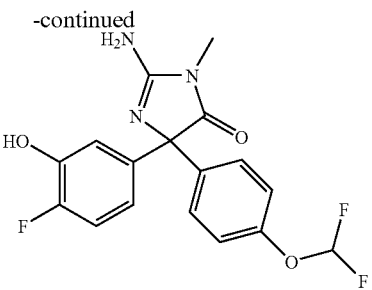

Using essentially the same procedure described in Example 17, step d, and employing 5-bromo-2-fluorophenol as starting material, the title compound was obtained and identified by NMR and mass spectral analyses. $^1$H NMR (DMSO-d6): δ 9.7 (bs, 1H), 7.39 (d, J=8.8 Hz, 2H), 7.12 (t, J=74.1 Hz, 1H), 7.06 (d, J=8.8 Hz, 2H), 7.01 (m, 2H), 6.78 (m, 1H), 6.62 (bs, 2H), and 2.93 (s, 3H); MS (ES pos) m/z 365.

EXAMPLES 61-78

Preparation of 2-Amino-5-[4-(difluoromethoxy)phenyl]-5-(alkoxyphenyl)-3-methyl-3,5-dihydro-4H-imidazol-4-one Compounds

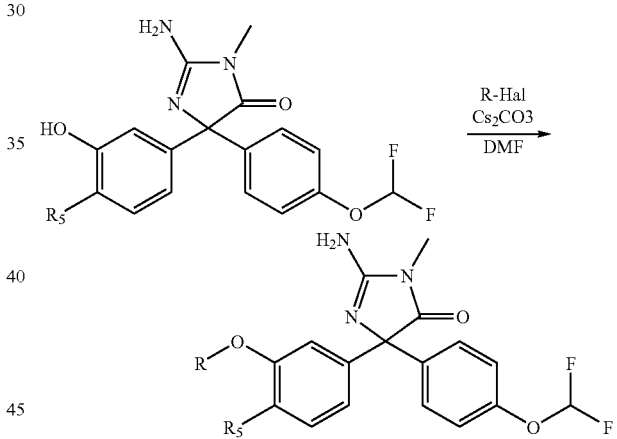

Using essentially the same procedure described in Example 59 and employing the desired alkyl halide and appropriate 2-amino-5-[4-(difluoromethoxy)phenyl]-5-(hydroxyphenyl)-3-methyl-3,5-dihydro-4H-imidazol-4-one substrate, the compounds shown in Table IV are obtained and identified by NMR and mass spectral analyses.

TABLE IV

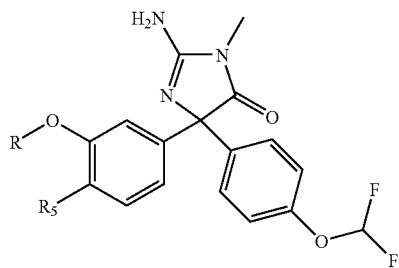

| Ex. No. | R | R5 | mp °C. | m/z |
|---|---|---|---|---|
| 61 | CH₂–△ (cyclopropyl) | H | 151-152 | 402 |
| 62 | CH₂CH₂CH₂CF₃ | H | 82-85 | 458 |
| 63 | CH₂CHF₂ | H | 158-159 | 412 |
| 64 | CH₂CH₂CH₂CH₂F | H | 139-140 | 422 |
| 65 | CH₂CH₂CH₂OC₆H₅ | H | foam | 482 |
| 66 | CH₂CH₂CN | H | foam | 415 |
| 67 | CH₂CH₂CHF₂ | F | foam | 424.2 |
| 68 | H₂C—≡—CH₃ | F | foam | 416.2 |
| 69 | CH₂CH₂CH₂CH₂F | F | foam | 438.2 |
| 70 | CH₂CHF₂ | F | foam | 428.1 |
| 71 | CH₂CH₂CH=CH₂ | H | foam | |
| 72 | CH₂CH₂CH=CH₂ | F | | |
| 73 | CH₂CH₂CH₂CH=CH₂ | H | | |
| 74 | (R)-CH₂CH(CH₃)CH₂CH=CH₂ | H | | |
| 75 | (S)-CH₂CH(CH₃)CH₂CH=CH₂ | H | | |
| 76 | CH₂=CHCH₂CH(CH₃)CH₂ | H | | |
| 77 | CH₃C(=CH₂)CH₂CH₂ | H | | |
| 78 | CH₂=CHCH₂ | H | | |

EXAMPLE 79

Preparation of (5R)-2-Amino-5-[4-(difluoromethoxy)phenyl]-5-[4-fluoro-3-(3-fluoropropox-1-yl)phenyl]-3-methyl-3,5-dihydro-4H-imidazol-4-one (A) and (5S)-2-Amino-5-[4-(difluoromethoxy)phenyl]-5-[4-fluoro-3-(3-fluoropropox-1-yl)phenyl]-3-methyl-3,5-dihydro-4H-imidazol-4-one (B)

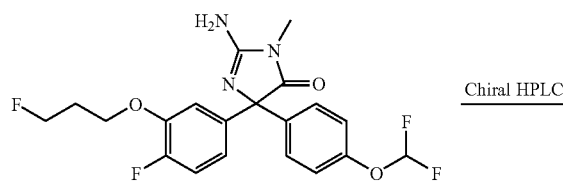

Chiral HPLC →

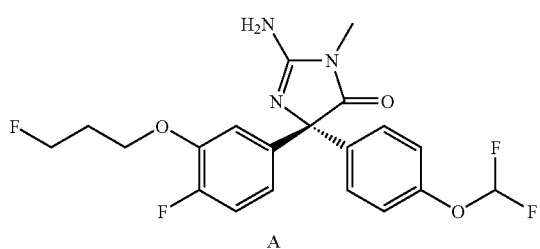

A

+

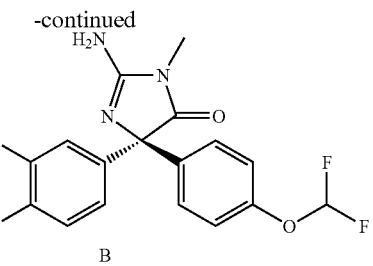

B

A racemic mixture of 2-amino-5-[4-(difluoromethoxy)phenyl]-5-[4-fluoro-3-(3-fluoropropox-1-yl)phenyl]-3-methyl-3,5-dihydro-4H-imidazol-4-one was separated by chiral HPLC using column type Chiralcel AD, 5×50 cm; the mobile phase was 14% ethanol in hexane with 0.1% diethylamine at 95 mL/min to obtain the title R-isomer (A) as a foam, identified by NMR and mass spectral analyses; $[\alpha]_D^{25}=-14.00°$ (1% EtOH); MS (ES) m/z 424.1; and the title S-isomer (B) as a foam, identified by NMR and mass spectral analyses; $[\alpha]_D^{25}=+15.00°$ (1% EtOH); MS (ES) m/z 424.1.

EXAMPLE 80

Preparation of (5R)-2-Amino-5-[3-(2,2-difluoroethoxy)-4-fluorophenyl]-5-[4-(difluoromethoxy)phenyl]-3-methyl-3,5-dihydro-4H-imidazol-4-one (A) and (5S)-2-Amino-5-[3-(2,2-difluoroethoxy)-4-fluorophenyl]-5-[4-(difluoromethoxy)phenyl]-3-methyl-3,5-dihydro-4H-imidazol-4-one (B)

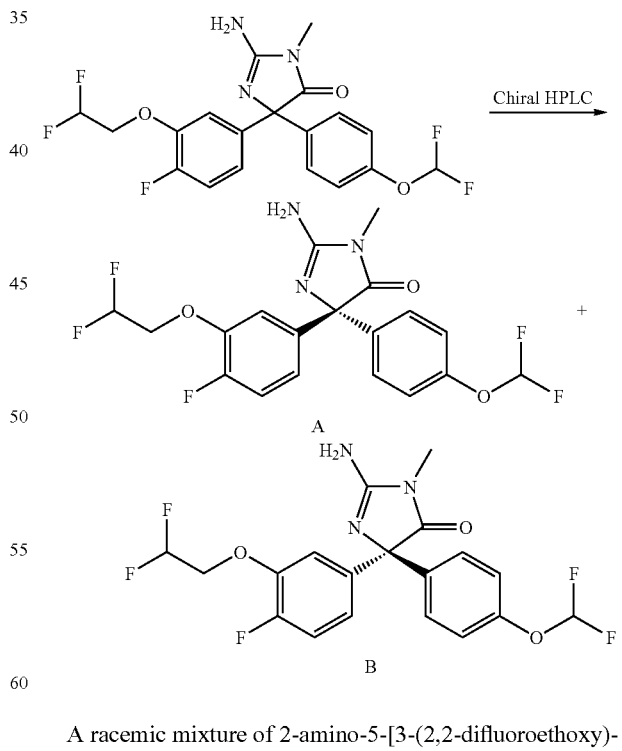

Chiral HPLC →

A

+

B

A racemic mixture of 2-amino-5-[3-(2,2-difluoroethoxy)-4-fluorophenyl]-5-[4-(difluoromethoxy)phenyl]-3-methyl-3,5-dihydro-4H-imidazol-4-one was separated by chiral HPLC using column type Chiralpak AD-H, 2×25 cm; the mobile phase was 15% ethanol in hexane with 0.1% diethylamine, to obtain the title R-isomer (A) as a glass, identified by NMR and mass spectral analyses; MS (ES) m/z 428.1; and the title S-isomer (B) as a foam, identified by NMR and mass spectral analyses; $[\alpha]D^{25}=+15.2°$ (1% EtOH); MS (ES) m/z 428.1.

EXAMPLE 81

Preparation of 2-Amino-5-{3-[(4,4-difluorobut-3-en-1-yl)oxy]phenyl}-5-[4-(difluoromethoxy)phenyl]-3-methyl-3,5-dihydro-4H-imidazol-4-one temperature, diluted with dichloromethane and filtered. The filtrate was concentrated in vacuo. The resultant residue was purified by flash chromatography (silica gel, eluant: 2.5% ethyl acetate/hexane to afford 1-(4,4-difluorobut-3-enyloxy)-3-((4-(difluoromethoxy)phenyl)ethynyl)benzene, 560 mg (46.2% yield); $^1$H NMR (chloroform-d1): δ 7.51 (d, J=8.8 Hz, 2H), 7.24 (m, 1H), 7.10 (m, 1H), 7.08 (d, J=8.8 Hz, 2H), 7.03 (m, 1H), 6.87 (m, 1H), 6.52 (t, J=73.5 Hz, 1H), 4.32 (m, 1H), 3.97 (t, J=6.4 Hz, 2H) and 2.47 (m, J=6.4 Hz, 2H); MS (ES pos) m/z 350.

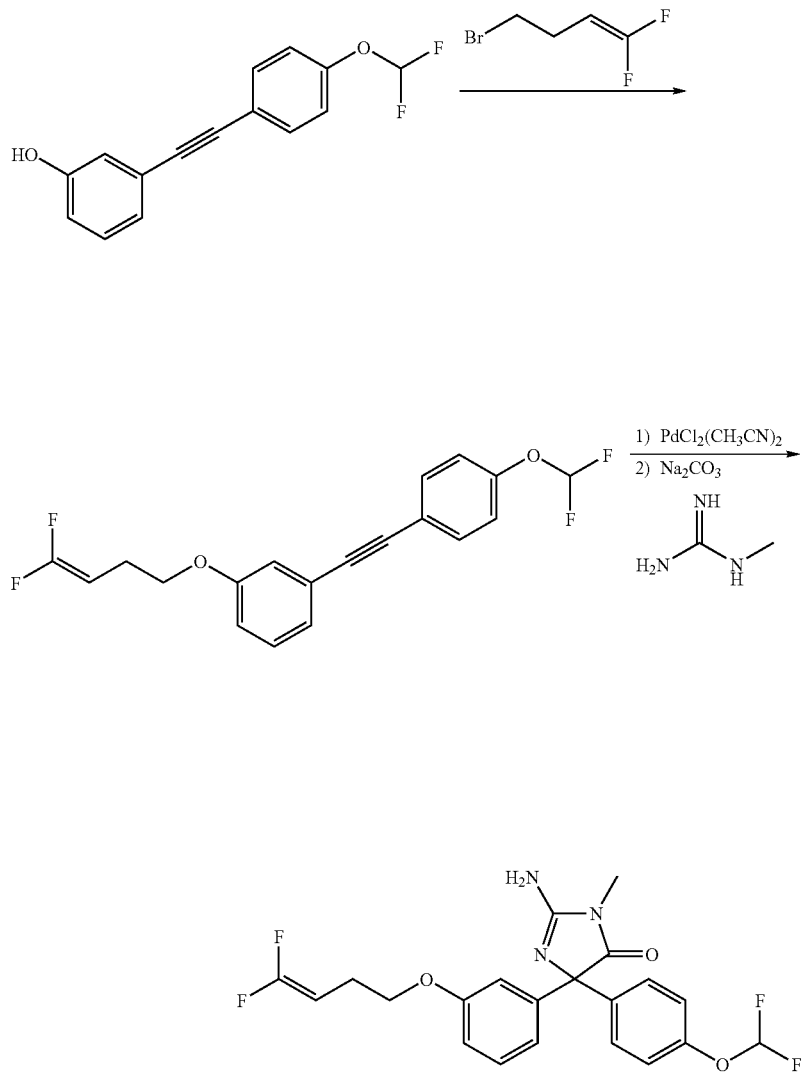

Step a) 1-(4,4-Difluorobut-3-enyloxy)-3-((4-(difluoromethoxy)phenyl)ethynyl)benzene A mixture of 3-((4-(difluoromethoxy)phenyl)ethynyl)phenol (900 mg), potassium carbonate (636 mg), Aliquat 336 (4 drops), sodium iodide (catalytic) and 4-bromo-1,1-difluoro-1-butene (591 μL) in methyl ethyl ketone was placed in a pressure vessel, heated at 80° C. for 15 h, cooled to room Step b) 2-Amino-5-{3-[(4,4-difluorobut-3-en-1-yl)oxy]phenyl}-5-[4-(difluoromethoxy)phenyl]-3-methyl-3,5-dihydro-4H-imidazol-4-one Using essentially the same procedure described in Example 1, steps b and c, and employing 1-(4,4-difluorobut-3-enyloxy)-3-((4-(difluoromethoxy)phenyl)ethynyl)benzene as starting material, the title compound was obtained as a white solid, mp 127-128° C., identified by NMR and mass spectral analyses. MS (ES) m/z 436.1.

EXAMPLE 82

Preparation of 2-Amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one

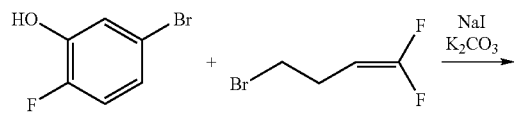

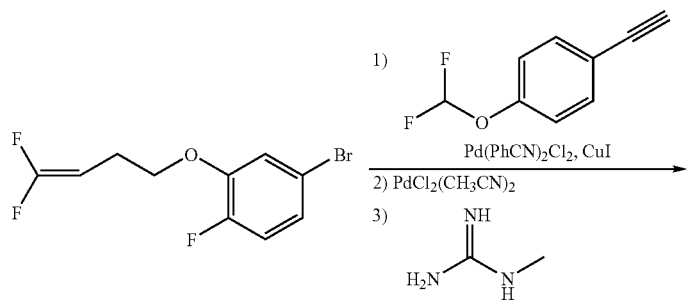

Step a) 4-bromo-2-(4,4-difluorobut-3-enyloxy)-1-fluorobenzene

A mixture of 2-fluoro-5-bromophenol (2.40 g), potassium carbonate (2.31 m), Aliquat 336 (5 drops), sodium iodide (catalytic) and 4-bromo-1,1-difluoro-1-butene (1.79 mL) in methyl ethyl ketone was placed in a pressure vessel and heated in a 82° oil bath for 15 hours. The reaction mixture was cooled, diluted with dichloromethane, filtered and evaporated in vacuo. The resultant residue was purified by flash chromatography (silica gel, eluant: 2.5% ethyl acetate/hexane to afford 4-bromo-2-(4,4-difluorobut-3-enyloxy)-1-fluorobenzene, 2.23 g (63% yield), identified by NMR analysis.

Step b) 2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one Using essentially the same procedure described in Example 60 and employing 4-bromo-2-(4,4-difluorobut-3-enyloxy)-1-fluorobenzene as starting material, the title compound was obtained as an off-white solid, 700 mg (68% yield), mp 139-140° C., identified by NMR and mass spectral analyses. MS (ES) m/z 456.1;

EXAMPLE 83

Preparation of 2-Amino-5-[4-(difluoromethoxy)phenyl]-5-(4-flroro-3-pent-4-en-1-yl)-3-methyl-3,5-dihydro-4H-imidazol-4-one

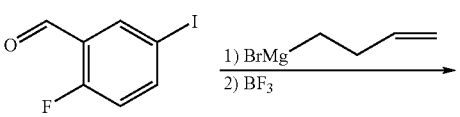

85

-continued

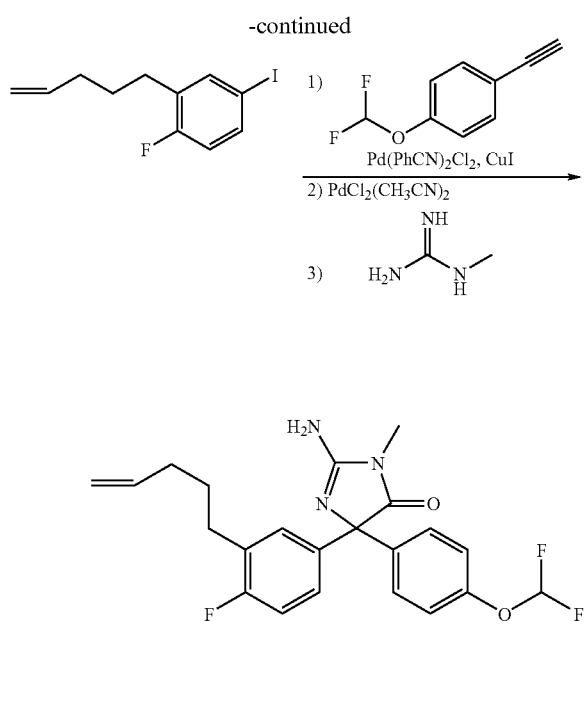

Step a) Preparation of 1-fluoro-4-iodo-2-pent-4-en-1-ylbenzene

A stirred solution of 2-fluoro-5-iodo-benzaldehyde (0.714 g, 2.86 mmol) in dry THF at −78° C. under nitrogen was treated over 10 min with 0.5 M 3-butenyl magnesium bromide in THF (6.85 mL, 3.43 mmol), stirred for 0.5 h, allowed to warm to −30° C. over 1 h, quenched with saturated ammonium chloride, diluted with water and extracted with ethyl acetate. The extracts were combined, dried over MgSO₄ and concentrated in vacuo. Purification of the resultant residue by flash chromatography (5% to 10% ethyl acetate/petroleum ether) gave 1-(2-fluoro-5-iodo-phenyl)pent-4-en-1-ol as a clear oil, 565 mg (65% yield). A portion of this oil (0.25 g, 0.82 mmol) was dissolved in dry methylene chloride, cooled to 0° C., treated with boron triflouride etherate (0.1 mL, 0.81 mmol), stirred for 15 minutes under a nitrogen atmosphere, warmed to room temperature for 1 h, and quenched with saturated sodium bicarbonate. The reaction mixture was partitioned between methylene chloride and H₂O; and the aqueous phase was extracted with methylene chloride. The organic phase and the extracts were combined, washed with brine, dried over MgSO₄ and concentrated in vacuo to give 1-fluoro-4-iodo-2-pent-4-en-1-ylbenzene as a clear oil, 0.18 g (76% yield).

Step b) 2-amino-5-[4-(difluoromethoxy)phenyl]-5-(4-flroro-3-pent-4-en-1-yl)-3-methyl-3,5-dihydro-4H-imidazol-4-one Using essentially the same procedure described in Example 60 and employing 1-fluoro-4-iodo-2-pent-4-en-1-ylbenzene as starting material, the title compound was obtained as a slight yellow foam, mp 45-46° C., identified by NMR and mass spectral analyses. MS (ES−): 416 (M−H)

86

EXAMPLE 84

Preparation of 2-Amino-5-(3-but-3-en-1-yl-4fluorophenyl)-5-[4-(difluoromethoxy)phenyl]-3-methyl-3,5-dihydro-4H-imidazol-4-one

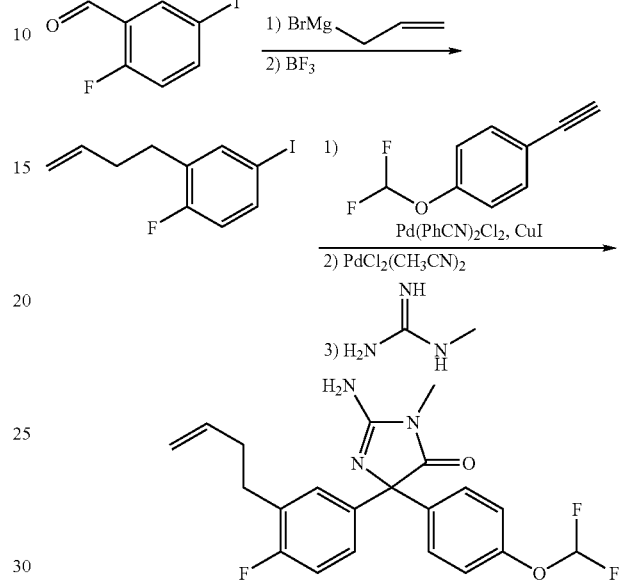

Using essentially the same procedure described in Example 83 and employing allyl magnesioum bromide in Step a, the title product was obtained as a slight yellow foam, mp 55-58° C., identified by NMR and mass spectral analyses. MS (ES+): 404 (M+H).

EXAMPLE 85

Preparation of 2-Amino-5-[4-(difluoromethoxy)phenyl]-5-[3-(1-hydroxybut-2-yn-1-yl)phenyl]-3-methyl-3,5-dihydro-4H-imidazol-4-one

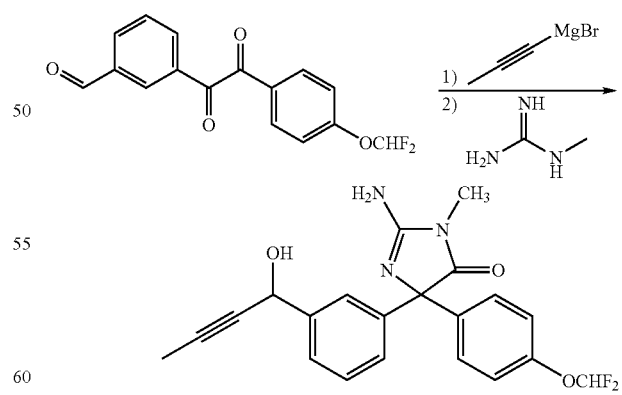

A stirred solution of 3-[2-(4-difluoromethoxyphenyl)-2-oxo-acetyl]-benzaldehyde (0.1 g, 0.33 mmol) in dry DME at 0° C. under nitrogen was treated over 10 min with 0.5 M 1-propynyl magnesium bromide in THF. The reaction was stirred for 0.5 h, quenched with saturated ammonium chloride, diluted with water and extracted with ethyl acetate. The combined extracts were dried over MgSO$_4$ and concentrated in vacuo. Purification of the resultant residue by flash chromatography (20% to 40% ethyl acetate/petroleum ether) gave 1-(4-difluoromethoxyphenyl)-2-[3-(1-hydroxybut-2-ynyl) phenyl]ethane-1,2-dione as a clear oil, 55 mg (49% yield). Using essentially the same procedure described as described in Example 1, step c, and employing 1-(4-difluoromethox-yphenyl)-2-[3-(1-hydroxy-but-2-ynyl)phenyl]-ethane-1,2-dione (0.055 g, 0.16 mmol), the title product was obtained as a slight yellow foam, 0.044 g (69% yield), identified by NMR and mass spectral analyses. MS (ES+): 400 (M+H).

EXAMPLE 86

Preparation of 2-Amino-5-[4-(difluoromethoxy)phe-nyl]-5-[3-(1,4-dihydroxybut-2-yn-1-yl)phenyl]-3-methyl-3,5-dihydro-4H-imidazol-4-one

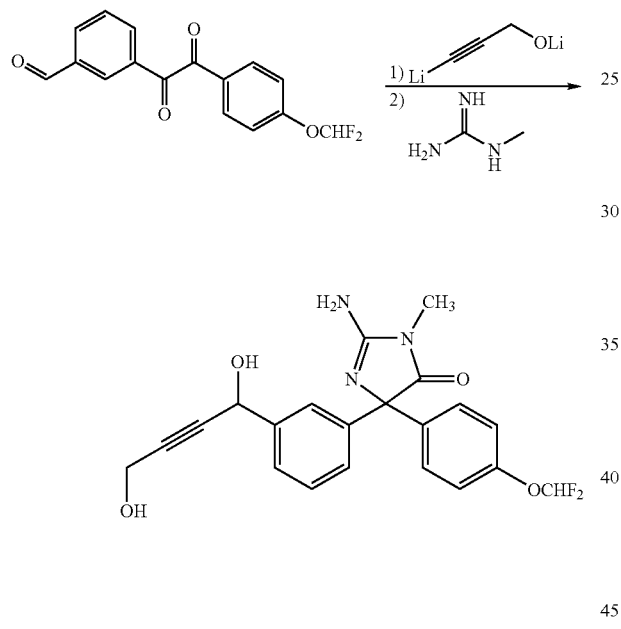

A stirred solution of propargyl alcohol (0.1 g, 1.78 mmol) in dry THF at –78° C. under nitrogen was treated dropwise with 1.9 M n-BuLi (1.88 mL, 3.57 mmol) over 10 min, stirred for 0.5 h and warmed to 0° C. A 3 mL portion of this solution was added to a stirred solution of 3-[2-(4-difluoromethox-yphenyl)-2-oxo-acetyl]benzaldehyde (0.15 g, 0.49 mmol) in dry DME at 0° C. under nitrogen. After 10 min, the reaction mixture was quenched with saturated ammonium chloride, diluted with water and extracted with ethyl acetate. The combined extracts were dried over MgSO$_4$ and concentrated in vacuo. Purification of the resultant residue by flash chromatography (30% to 70% ethyl acetate/petroleum ether) gave 1-[4-(difluoromethoxy)phenyl]-2-[3-(1,4-dihydroxybut-2-ynyl)phenyl]ethane-1,2-dione as a clear oil, 52 mg (29% yield). Using essentially the same procedure described in Example 1, step c, and employing 1-[4-(difluoromethoxy) phenyl]-2-[3-(1,4-dihydroxybut-2-ynyl)phenyl]ethane-1,2-dione (0.052 g, 0.14 mmol), the title compound was obtained as a slight brown foam, 0.031 g (52% yield), identified by NMR and mass spectral analyses. MS (ES+): 416 (M+H).

EXAMPLE 87

Preparation of 2-Amino-5-[4-(difluoromethoxy)phe-nyl]-5-[3-(2,2-dimethyl-3-oxocyclobutyl)phenyl]-3-methyl-3,5-dihydro-4H-imidazol-4-one

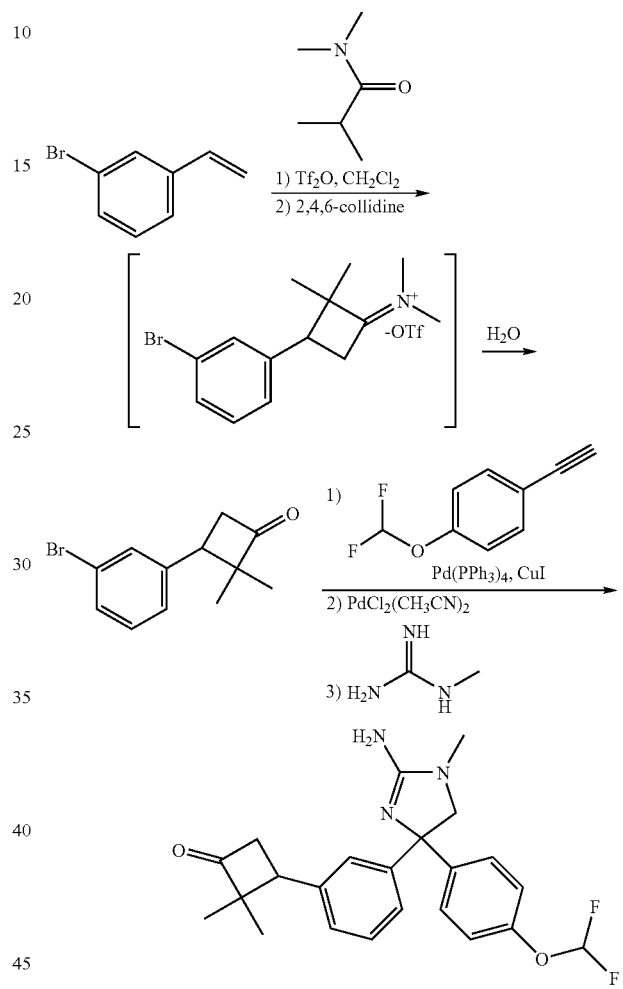

Step a)
3-(3-Bromo-phenyl)-2,2-dimethyl-cyclobutanone

A solution of N,N,2-trimethylpropionamide (3.65 g, 31.7 mmol) and dichloromethane under nitrogen at –13° C., was treated via syringe with triflic anhydride (Tf$_2$O), stirred for 10 minutes, treated dropwise over 40 minutes with a solution of 3-bromostyrene (5.04 g, 27.6 mmol) and 2,4,6-collidine (4.32 g, 35.7 mmol) in CH$_2$Cl$_2$, heated at reflux temperature for 20 h, cooled to room temperature and concentrated in vacuo. The concentrate was diluted with water and CH$_2$Cl$_2$ and heated at 89° C. for 7 h. After cooling to room temperature, the phases were separated; and the aqueous phase was extracted with CH$_2$Cl$_2$ The organic phase and the extracts were combined, dried over Na$_2$SO$_4$ and concentrated in vacuo. Purification of the resultant concentrate by silica gel column chromatography (gradient; 5%-10% EtOAc in hexanes) afforded 3-(3-bromophenyl)-2,2-dimethyl-cyclobutanone as a pale yellow oil, 4.26 g (61% yield); 1H NMR (400 MHz, DMSO-$d_6$) δ ppm 0.69 (s, 3 H) 1.25 (s, 3 H) 3.24 (dd, J=17.4, 9.0 Hz, 1 H) 3.44 (t, J=8.9 Hz, 1 H) 3.64 (dd, J=17.3, 8.7 Hz, 1 H) 7.23-7.35 (m, 2 H) 7.43-7.47 (m, 1 H) 7.49 (s, 1 H);

Step b) 2-amino-5-[4-(difluoromethoxy)phenyl]-5-[3-(2,2-dimethyl-3-oxocyclobutyl)phenyl]-3-methyl-3,5-dihydro-4H-imidazol-4-one Using essentially the same procedure described in Example 17, step d, and employing 3-(3-bromophenyl)-2,2-dimethyl-cyclobutanone as starting material, the title compound was obtained as a white solid, mp 172-174° C.; $^1$H NMR (400 MHz, DMSO-$d_6$) δ ppm 0.61 (s, 3 H) 1.21 (s, 3 H) 2.98 (s, 3 H) 3.19-3.28 (m, 1 H) 3.34-3.40 (m, 1 H) 3.41-3.47 (m, J=4.9 Hz, 1 H) 6.71 (s, 2 H) 6.96-7.19 (m, 4 H) 7.24-7.37 (m, 3 H) 7.44 (d, J=7.9 Hz, 2 H); MS (ES) m/z 426.2 [M−H]−; HRMS: calcd for $C_{23}H_{23}F_2N_3O_3$+H+, 428.17802. found (ESI, [M+H]+), 428.1780.

EXAMPLE 88

Preparation of 2-Amino-5-[4-(difluoromethoxy)phenyl]-3-methyl-5-[3-(3-oxocyclobutyl)phenyl]-3,5-dihydro-4H-imidazol-4-one

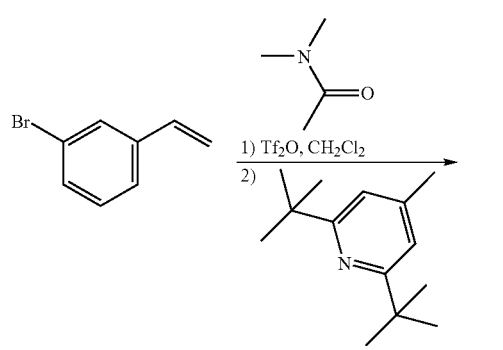

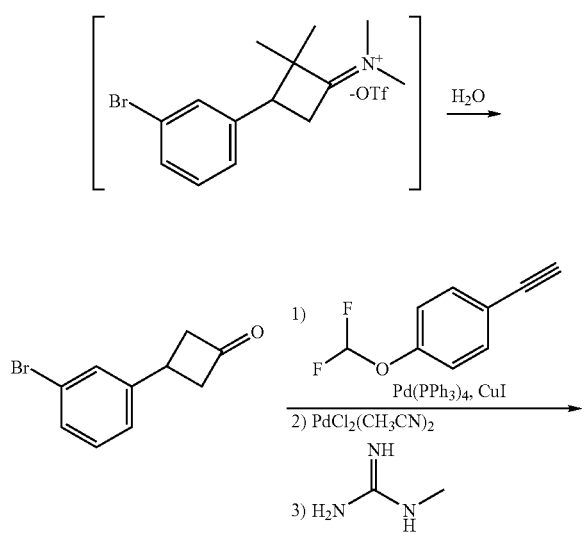

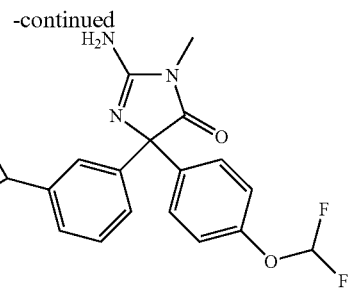

Using essentially the same procedure described in Example 87 and employing N,N-dimethylacetamide in Step a, the title product was obtained a white solid, mp 68-70° C. (foams); $^1$H NMR (400 MHz, DMSO-$d_6$) δ ppm 2.97 (s, 3 H) 3.06-3.17 (m, 2 H) 3.36-3.46 (m, 2 H) 3.59 (q, J=7.3 Hz, 1 H) 6.68 (s, 2 H) 7.10 (d, J=8.8 Hz, 2 H) 7.16 (t, J=74.2 Hz, 1 H) 7.23-7.34 (m, 3 H) 7.39-7.50 (m, 3 H); MS (ES) m/z 398.1 [M−H]−; HRMS: calcd for $C_{21}H_{19}F_2N_3O_3$+H+, 400.14672. found (ESI, [M+H]+), 400.1475.

EXAMPLE 89

Preparation of 2-Amino-5-[4-(difluoromethoxy)phenyl]-5-[3-(3-hydroxycyclobutyl)phenyl]-3-methyl-3,5-dihydro-4H-imidazol-4-one

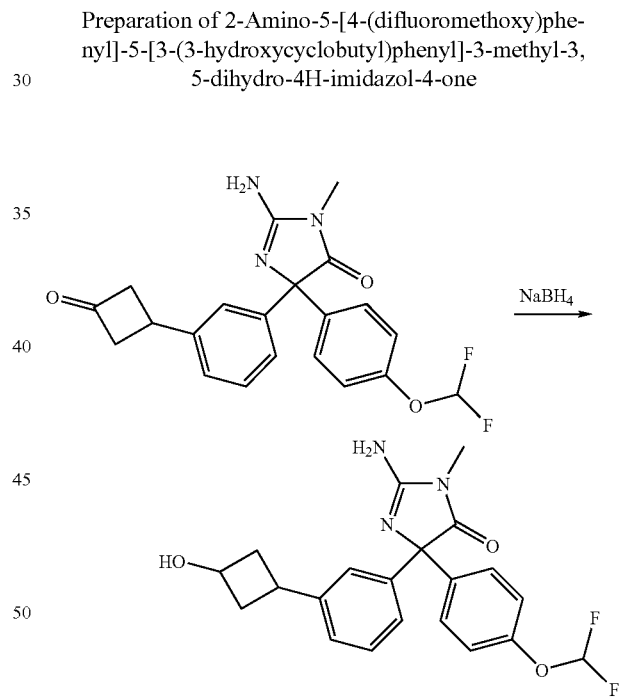

A methanolic solution of 2-amino-5-[4-(difluoromethoxy)phenyl]-3-methyl-5-[3-(3-oxocyclobutyl)phenyl]-3,5-dihydro-4H-imidazol-4-one (0.324 gm, 0.811 mmol) at ice bath temperatures was treated all at once with NaBH$_4$ (0.042 gm, 1.11 mmol), stirred at 0° C. for 45 minutes and concentrated in vacuo. The solid residue was partitioned between water and chloroform. The organic phase was separated, dried over sodium sulfate and evaporated to a foam. This foam was dissolved in chloroform and precipitated with hexane to give the title compound as a white solid, 0.307 g (94% yield), mp 186-190° C.; $^1$H NMR (400 MHz, DMSO-$d_6$) δ ppm 1.70-

1.86 (m, 2 H) 2.53-2.60 (m, 2 H) 2.70-2.85 (m, 1 H) 2.97 (s, 3 H) 3.89-4.08 (m, 1 H) 5.08 (t, J=5.2 Hz, 1 H) 6.69 (s, 2 H) 7.10 (d, J=8.6 Hz, 3 H) 7.17 (t, J=74.2 Hz, 1 H) 7.19-7.33 (m, 3 H) 7.45 (d, J=8.8 Hz, 2 H); MS (ES) m/z 400.2 [M−H]−; HRMS: calcd for $C_{21}H_{21}F_2N_3O_3$+H+, 402.16237. found (ESI, [M+H]+), 402.1630.

EXAMPLE 90

Preparation of Ethyl [3-(3-{2-Amino-4-[4-(difluoromethoxy)phenyl]-1-methyl-5-oxo-4,5-dihydro-1H-imidazol-4-yl}phenyl)cyclobutylidene]acetate

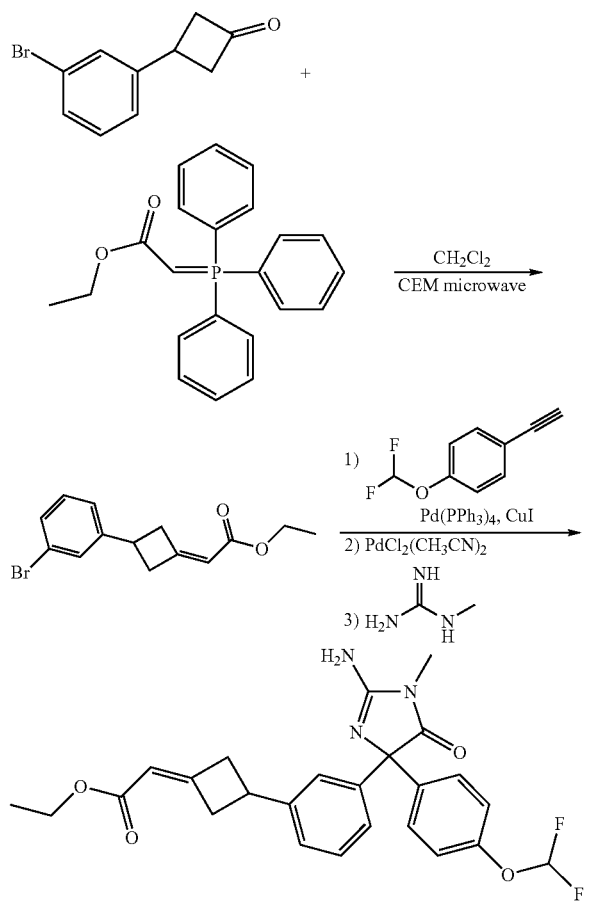

Step a) [3-(3-bromophenyl)cyclobutylidene]acetic acid ethyl ester

A solution of 3-(3-bromophenyl)cyclobutanone (2.03 g 9.02 mmol) and triphenylphosphoranylidene acetic acid ethyl ester (15.72 gms 45.12 mmol) dichloromethane was irradiated in a CEM Discover™ microwave instrument for 30 minutes at 120° C. Pressure reached a maximum of 180 PSI. Standard work-up procedures followed by purification by column chromatography (isocratic; 10% diethyl ether in hexanes) afforded [3-(3-bromophenyl)cyclobutylidene]acetic acid ethyl ester as an oil, 2.37 g (89% yield), 1H NMR (400 MHz, DMSO-$d_6$) δ ppm 1.20 (t, J=7.1 Hz, 3 H) 2.89-3.00 (m, 1 H) 3.03-3.11 (m, 1 H) 3.16-3.27 (m, 1 H) 3.46-3.57 (m, 1 H) 3.63 (q, J=8.0 Hz, 1 H) 4.08 (q, J=7.0 Hz, 2 H) 5.71 (q, J=2.9 Hz, 1 H) 7.25-7.35 (m, 2 H) 7.39-7.43 (m, 1 H) 7.48-7.52 (m, 1 H); MS (APPI) m/z 295 [M+H]+.

Step b) ethyl [3-(3-{2-Amino-4-[4-(difluoromethoxy)phenyl]-1-methyl-5-oxo-4,5-dihydro-1H-imidazol-4-yl}phenyl)-1-methoxycyclobutylidene] acetate Using essentially the same procedure described in Example 17, step d, and employing [3-(3-bromophenyl)cyclobutylidene]acetic acid ethyl ester, the title compound is obtained as a white foam solid, mp 78-80° C.; $^1$H NMR (400 MHz, DMSO-$d_6$) δ ppm 1.19 (t, J=7.1 Hz, 3 H) 2.78-2.89 (m, 1 H) 2.97 (s, 3 H) 3.02-3.07 (m, 1 H) 3.16-3.26 (m, 1 H) 3.45-3.53 (m, 1 H) 3.55-3.66 (m, 1 H) 4.07 (q, J=7.0 Hz, 2 H) 5.64-5.75 (m, 1 H) 6.67 (s, 2 H) 7.05-7.11 (m, 2 H) 7.16 (t, J=74.2 Hz, 1 H) 7.17-7.21 (m, 1 H) 7.23-7.33 (m, 2 H) 7.37 (s, 1 H) 7.43-7.51 (m, 2 H); MS (ES) m/z 468.1 [M−H]−.

EXAMPLE 91

Preparation of Methyl [3-(3-{2-Amino-4-[4-(difluoromethoxy)phenyl]-1-methyl-5-oxo-4,5-dihydro-1H-imidazol-4-yl}phenyl)cyclobutylidene]acetate

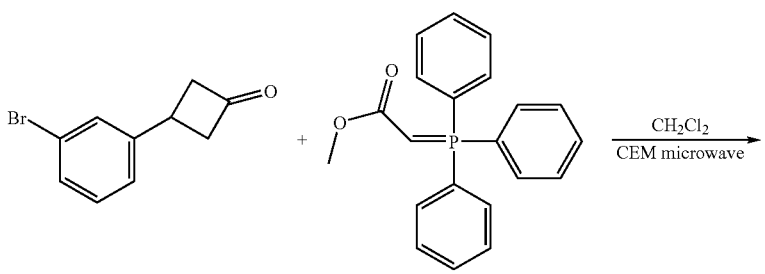

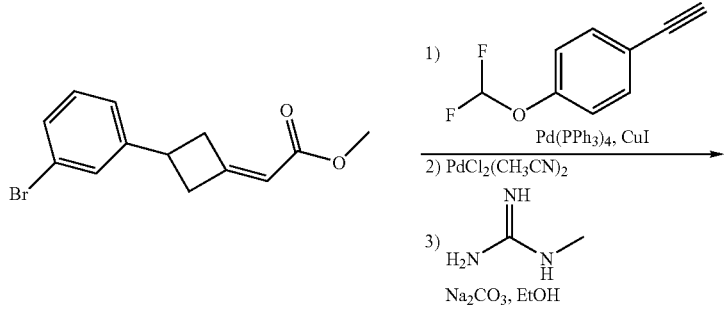

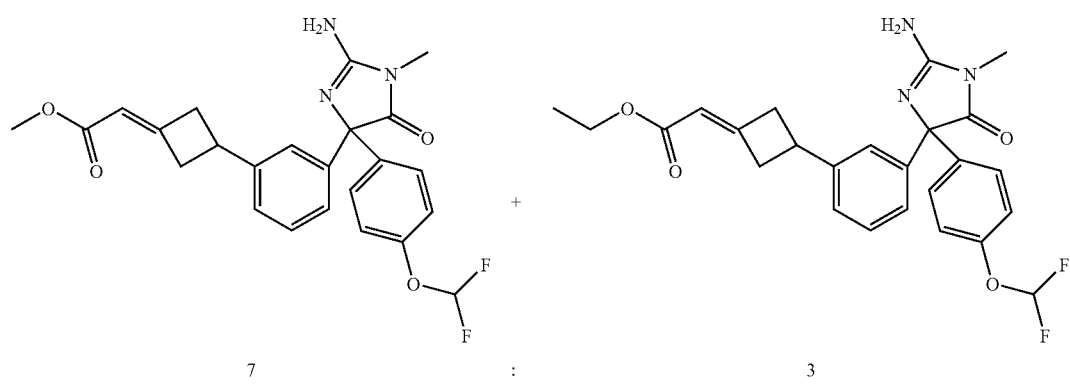

| 7 | : | 3 |

Using essentially the same procedure described in Example 90 and employing triphenylphosphoranylidene acetic acid ethyl ester in step a, the title product was obtained as a foam. NMR analysis indicates the foam is a 7:3 mixture of methyl and ethyl esters. $^1$H NMR (400 MHz, DMSO-d$_6$), a mixture of methyl and ethyl esters (7:3) δ ppm 1.15-1.23 (m, 3 H of ethyl ester) 2.76-2.91 (m, 1 H) 2.97 (s, 3 H) 2.99-3.07 (m, 1 H) 3.11-3.27 (m, 1 H) 3.42-3.55 (m, 1 H) 3.55-3.60 (m, 1 H) 3.61 (s, 3 H of methyl ester) 4.01-4.12 (m, 2 H of ethyl ester) 5.64-5.77 (m, 1 H) 6.68 (s, 2 H) 7.10 (d, J=8.8 Hz, 2 H) 7.16 (t, J=74.2 Hz, 1 H) 7.18-7.22 (m, 1 H) 7.23-7.33 (m, 2 H) 7.35-7.38 (m, 1 H) 7.46 (dt, J=9.2, 2.6 Hz, 2 H). MS (ES) m/z 454.1 (Me ester) [M−H]−; MS (ES) m/z 468.1 (Et ester) [M−H]−

EXAMPLE 92

Preparation of Methyl [3-(3-{2-Amino-4-[4-(difluoromethoxy)phenyl]-1-methyl-5-oxo-4,5-dihydro-1H-imidazol-4-yl}phenyl)cyclobutyl]acetate

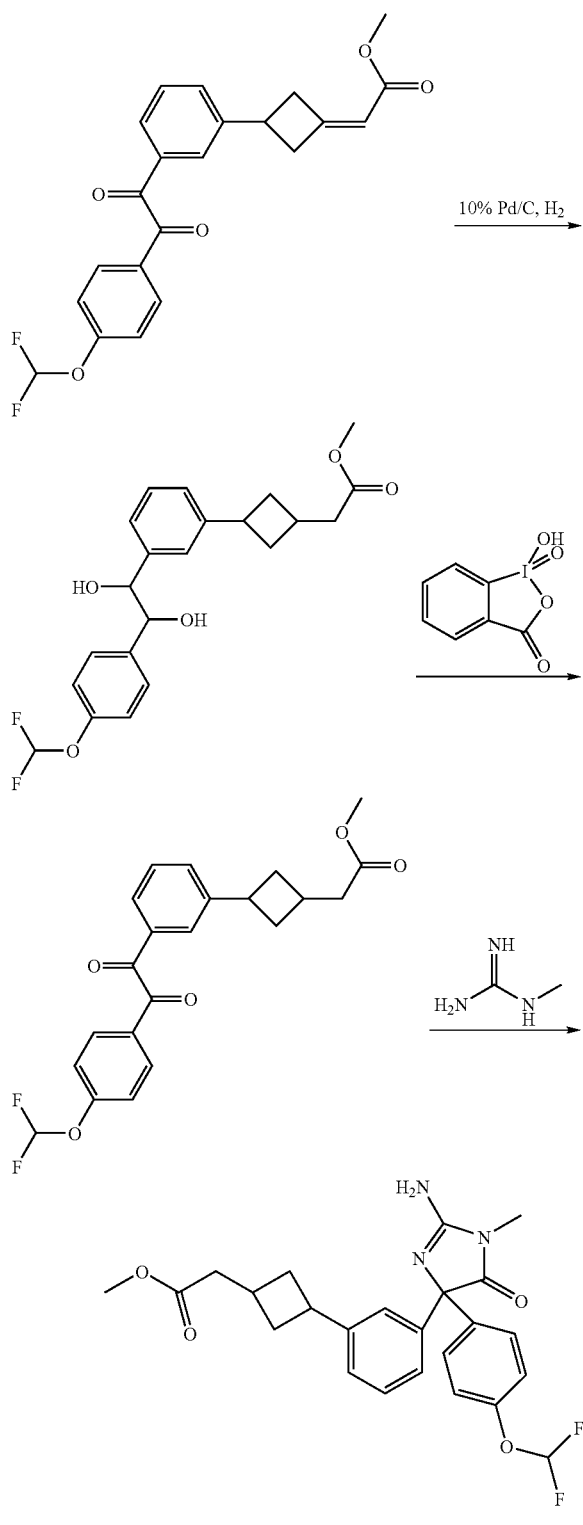

Step a) (3-{3-[2-(4-Difluoromethoxyphenyl)-1,2-dihydroxyethyl]phenyl}-cyclobutyl)acetic acid methyl ester A mixture of 10% Pd/C (0.092 g) and (3-{3-[2-(4-difluoromethoxyphenyl)-2-oxoacetyl]-henyl}-cyclobutylidene)acetic acid methyl ester (0.78 g, 1.95 mmol) in ethanol was placed on a Parr Hydrogenator under 15 PSI hydrogen for 3 hours. More 10% Pd/C (0.056 g) was added and the shaker was placed under 30 PSI hydrogen atmosphere for 2 hours. The reaction mixture was filtered thru Celite. The filtrate was concentrated in vacuo to give (3-{3-[2-(4-Difluoromethoxyphenyl)-1,2-dihydroxyethyl]phenyl}-cyclobutyl)acetic acid methyl ester as an oil, 402 mg (51% yield); 1H NMR (400 MHz, DMSO-$d_6$) δ ppm 1.67 (q, J=9.1 Hz, 1 H) 1.92-2.07 (m, 1 H) 2.13-2.23 (m, 1 H) 2.32-2.44 (m, 3 H) 2.56-2.64 (m, 1 H) 3.35-3.44 (m, 1 H) 3.55-3.65 (m, 3 H) 4.45-4.63 (m, 2 H) 5.08-5.38 (m, 2 H) 6.56-7.43 (m, 9 H); MS (ES) m/z 405.1 [M−H]−

Step b) 1-(4-difluoromethoxyphenyl)-2-[3-(3-oxocyclobutyl)-phenyl]ethane-1,2-dione A mixture of a 1M solution of o-iodoxybenzoic acid (IBX) in DMSO (0.90 mL) and (3-{3-[2-(4-difluoromethoxyphenyl)-1,2-dihydroxyethyl]phenyl-cyclobutyl)acetic acid methyl ester (0.144 g, 0.354 mmol) was stirred for 30 min, treated with an additional 1.2 mL of 1M IBX in DMSO, stirred for 15 min and partitioned between water and diethyl ether. The organic phase is separated, dried over $Na_2SO_4$ and concentrated in vacuo. Purification of the resultant residue by column chromatography (10% hexane in ethyl acetate) afforded 1-(4-difluoromethoxyphenyl)-2-[3-(3-oxocyclobutyl)phenyl]ethane-1,2-dione as an oil, 0.133 g (93% yield); $^1$H NMR (400 MHz, DMSO-$d_6$) δ ppm 1.71-1.87 (m, 2 H) 2.06-2.17 (m, 1 H) 2.26 (s, 1 H) 2.55-2.69 (m, 2 H) 3.46 (s, 1 H) 3.54-3.62 (m, 3 H) 3.73 (s, 1 H) 7.23-7.82 (m, 7 H) 7.95-8.06 (m, 2 H); MS (ES) m/z 403.0 [M+H]+

Step c) methyl [3-(3-{2-amino-4-[4-(difluoromethoxy)phenyl]-1-methyl-5-oxo-4,5-dihydro-1H-imidazol-4-yl}phenyl)cyclobutyl]acetate Using essentially the same procedure described in Example 1, step c, and employing 1-(4-difluoromethoxyphenyl)-2-[3-(3-oxocyclobutyl)phenyl]ethane-1,2-dione as starting material, the title compound was obtained as a white solid, mp 68-70° C. (foams); $^1$H NMR (400 MHz, DMSO-$d_6$) δ ppm 1.63-1.76 (m, 2 H) 1.98-2.04 (m, 1 H) 2.11-2.18 (m, 1 H) 2.36-2.46 (m, 4 H) 2.58-2.65 (m, 2 H) 3.02 (s, 3 H) 3.54-3.62 (m, 3 H) 7.10-7.17 (m, J=7.6, 7.6 Hz, 3 H) 7.19 (t, J=74.1 Hz, 1 H) 7.21-7.31 (m, 3 H) 7.41-7.47 (m, 2 H); MS (ES) m/z 456.1 [M−H]−

EXAMPLE 93

Preparation of 2-Amino-5-[3-(difluoromethoxy)phenyl]-5-[4-(difluoromethoxy)phenyl]-3-methyl-3,5-dihydro-4H-imidazol-4-one

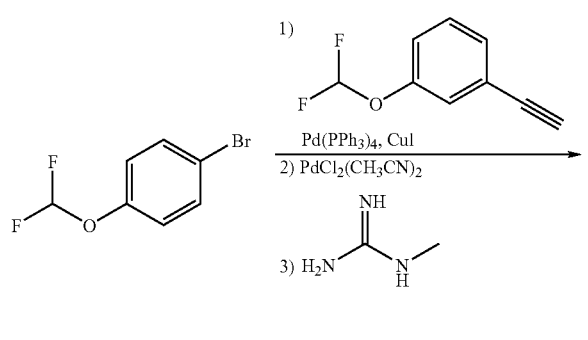

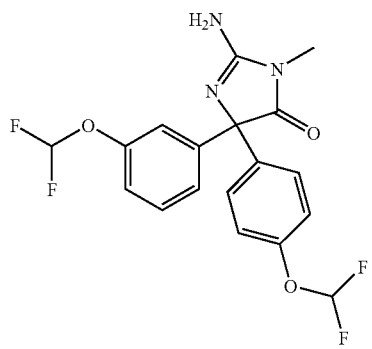

Using essentially the same procedure described in Example 18, step d, and employing 4-difluoromethoxybromobenzene and 1-difluoromethoxy-3-ethynylbenzene as starting material, the title compound was obtained as a white foam, mp 52-54° C.; 1H NMR (400 MHz, DMSO-d$_6$) δ ppm 2.98 (s, 3 H) 6.75 (s, 2 H) 6.96-7.13 (m, 3 H) 7.17 (d, J=2.9 Hz, 1 H) 7.24 (s, 1 H) 7.33-7.38 (m, 3 H) 7.48 (d, J=8.8 Hz, 2 H); MS (ES) m/z 398.1 [M+H]+.

EXAMPLE 94

Preparation of (5S)-2-Amino-5-[3-(difluoromethoxy)phenyl]-5-[4-(difluoromethoxy)phenyl]-3-methyl-3,5-dihydro-4H-imidazol-4-one (A) and (5R)-2-Amino-5-[3-(difluoromethoxy)phenyl]-5-[4-(difluoromethoxy)phenyl]-3-methyl-3,5-dihydro-4H-imidazol-4-one (B)

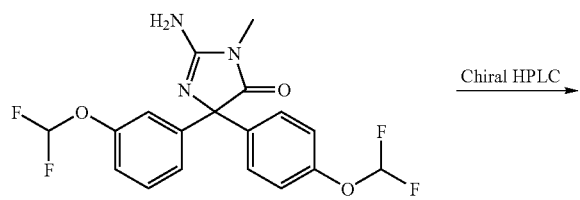

Chiral HPLC

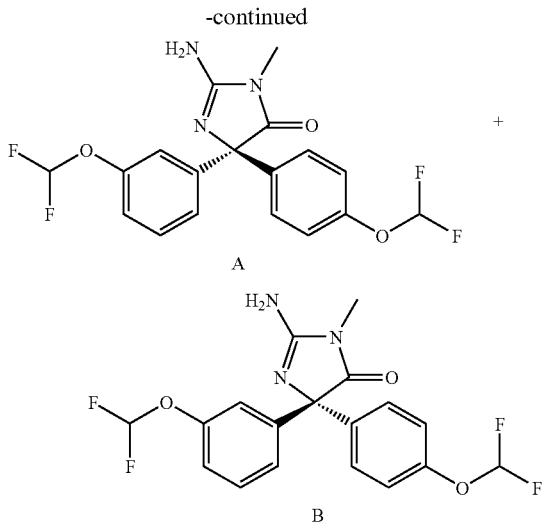

A racemic mixture of 2-amino-5-[3-(difluoromethoxy)phenyl]-5-[4-(difluoromethoxy)phenyl]-3-methyl-3,5-dihydro-4H-imidazol-4-one was placed on a Chiralcel OJ, 2×25 cm column (elution 10% EtOH in Hexane/DEA at a flow rate of 22 mL/min). Material was collected at 6.14 minutes (product A) and at 7.42 minutes (product B). Separately each enantiomer product was concentrated at the rotovap, diluted with ethanol and concentrated again to give an oily residue. Each oily residue was diluted with diethyl ether and an equal volume of hexane and concentrated to give the title enantiomeric products as a white solid: A (118 mg) and B (96 mg). Product A was identified as the (+)-enantiomer, [α]$_D^{25}$=8.6° (c=1% MeOH); 1H NMR (400 MHz, DMSO-d$_6$) α ppm 2.98 (s, 3 H) 6.75 (s, 2 H) 6.96-7.13 (m, 3 H) 7.17 (d, J=2.9 Hz, 1 H) 7.24 (s, 1 H) 7.33-7.38 (m, 3 H) 7.48 (d, J=8.8 Hz, 2 H); MS (ES) m/z 396.1 [M−H]−; and Product B was identified as the (R)-enantiomer, [α]$_D^{25}$=−8.2° (c=1% MeOH); 1H NMR (400 MHz, DMSO-d$_6$) δ ppm 2.98 (s, 3 H) 6.75 (s, 2 H) 6.96-7.13 (m, 3 H) 7.17 (d, J=2.9 Hz, 1 H) 7.24 (s, 1 H) 7.33-7.38 (m, 3 H) 7.48 (d, J=8.8 Hz, 2 H); MS (ES) m/z 398.1 [M+H]+.;

EXAMPLE 95

Preparation of 2-Amino-5-[4-(difluoromethoxy)phenyl]-5-{3-[(1R)-1-fluoropent-4-en-1-yl]pheny}-3-methyl-3,5-dihydro-4H-imidazol-4-one

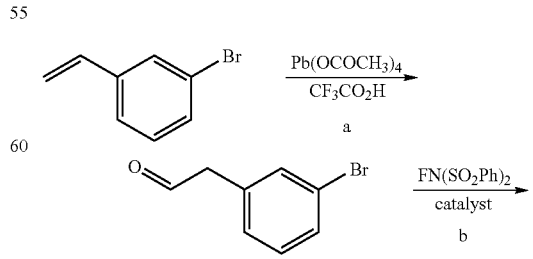

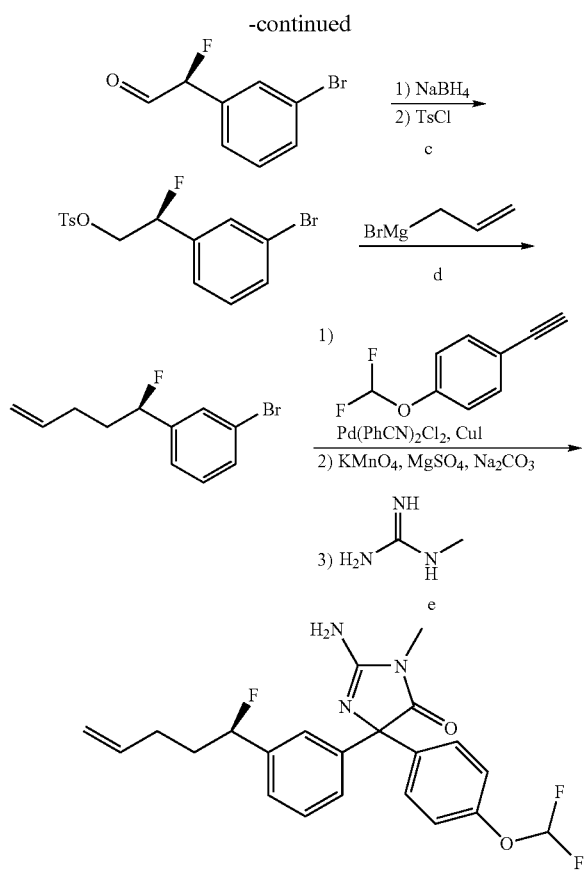

Step a) (3-Bromophenyl)acetaldehyde

A mixture of lead tetraacetate (3.6 g, 8.2 mmol) and trifluoroacetic acid (8.25 mL) at 0° C. is treated dropwise with a solution of 1-bromo-3-vinylbenzene (1.5 g, 8.2 ml) in dichloromethane, allowed to warm to room temperature, stirred for 2 h at room temperature, diluted with dichloromethane, poured into water, stirred vigorously and filtered through a pad of celite. The filtrate is separated. The filtercake is rinsed with additional portions of dichloromethane. The combined organic phases are washed sequentially with water, NaHCO$_3$ and brine, dried over MgSO$_4$ and concentrated in vacuo to afford (3-bromophenyl)acetaldehyde.

Step b) (R)-2-Fluro-2-(3-bromophenyl)acetaldehyde (Lit. Ref: MacMillan and Beeson, JACS 2005, 127, 8826)

A homogeneous mixture of (5R)-5-benzyl-2,2,3-trimethyl imidazolidin-4-one dichloroacetic acid salt (97 mg, 0.4 mmol) and N-fluorobenzenesulfonimide (3.15 g, 10 mmol) in a 9:1 mixture of acetone and isopropanol at room temperature is treated with (3-bromophenyl)acetaldehyde (280 mg, 1.4 mmol), stirred for 1 h at room temperature, cooled to −78° C., diluted with ether, and filtered through a pad of celite. The filtercake is washed with additional ether. The combined filtrates are treated with methylsulfide (5 mL), washed with saturated NaHCO$_3$ and brine, dried over MgSO$_4$ and concentrated under reduced pressure to give (R)-2-fluro-2-(3-bromophenyl)acetaldehyde.

Step c) Toluene-4-sulfonic acid (S)-2-(3-bromophenyl)-2-fluoro-ethyl ester

A solution of (R)-2-fluoro-2-(3-bromophenyl)acetaldehyde in CH$_2$Cl$_2$ and ethanol is treated with NaBH$_4$ (189 mg, 5 mmol), stirred for 30 min, cooled to 0° C., treated with saturated NH$_4$Cl, warmed to room temperature, stirred vigorously for 1 h at room temperature and diluted with CH$_2$Cl$_2$. The phases are separated. The aqueous phase is extracted with CH$_2$Cl$_2$. The organic phase and the extracts are combined, washed with NaHCO$_3$ and brine, dried over MgSO$_4$ and concentrated in vacuo. The resultant residue is purified by column chromatography (5% EtOAc and hexane as eluant)to give (R)-2-fluoro-2-(3-bromophenyl)-1-ethanol.

A solution of (R)-2-fluoro-2-(3-bromophenyl)-1-ethanol (5 mmol) and p-toluenesulfonyl chloride (5.1 mmol) in CH$_2$Cl$_2$ at ice bath temperatures is treated with stirring with pyridine. The reaction mixture is heated at reflux temperature under a nitrogen atmosphere for 16 h, cooled to room temperature, washed with 10% HCl, saturated NaHCO$_3$ and brine, dried over MgSO$_4$ and concentrated in vacuo to give toluene4-sulfonic acid (S)-2-(3-bromophenyl)-2-fluoro-ethyl ester.

Step d) 1-Bromo-(S)-3-(1-fluoropent-4-en-1-yl)benzene

A solution of toluene-4-sulfonic acid (S)-2-(3-bromophenyl)-2-fluoro-ethyl ester (5 mmol) in THF at room temperature is treated dropwise with a 1M solution of allylmagnesium bromide, stirred at room temperature for 5 h, quenched with saturated NH$_4$Cl and extracted with ethyl acetate. The extracts are combined, washed sequentially with water and brine, dried over MgSO$_4$ and concentrated in vacuo to afford 1-bromo-(S)-3-(1-fluoropent-4-en-1-yl)benzene.

Step e) 2-Amino-5-[4-(difluoromethoxy)phenyl]-5-{3-[(1R)-1-fluoropent-4-en-1-yl]phenyl}-3-methyl-3,5-dihydro-4H-imidazol-4-one Using essentially the same procedure described in Example 14, steps f, g and h, and employing 1-bromo-(S)-3-(1-fluoropent-4-en-1-yl)benzene as the starting material, the title product is obtained and identified by NMR and mass spectral analyses.

EXAMPLE 96

Preparation of 2-Amino-5-[4-(difluoromethoxy)phenyl]-5-{3-[(1R)-1-fluorobut-3-en-1-yl]phenyl}-3-methyl-3,5-dihydro-4H-imidazol-4-one

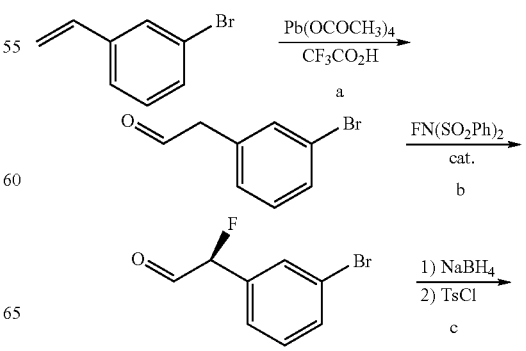

-continued

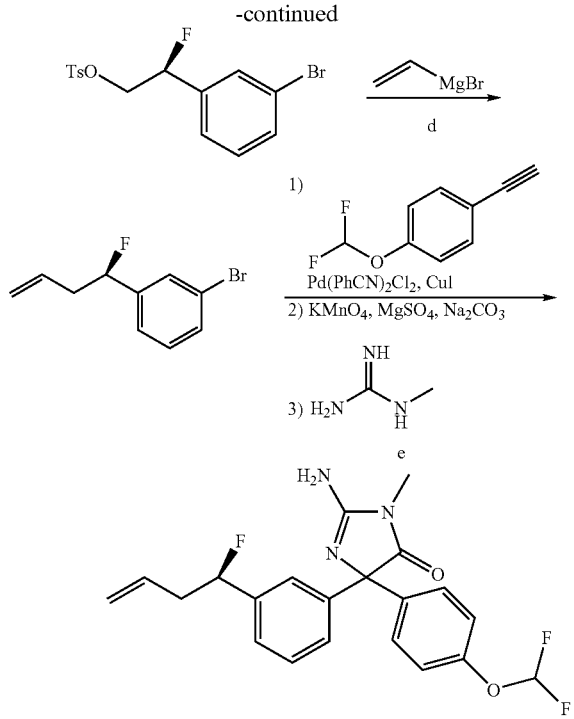

Using essentially the same procedure described in Example 95 and employing ethenylmagnesium bromide in step d, the title compound is obtained and identified by NMR and mass spectral analyses.

EXAMPLE 97

Preparation of N-(3-{2-Amino-4-[4-(difluoromethoxy)phenyl]-1-methyl-5-oxo-4,5-dihydro-1H-imidazol-4-yl}phenyl)ethanesulfonamide

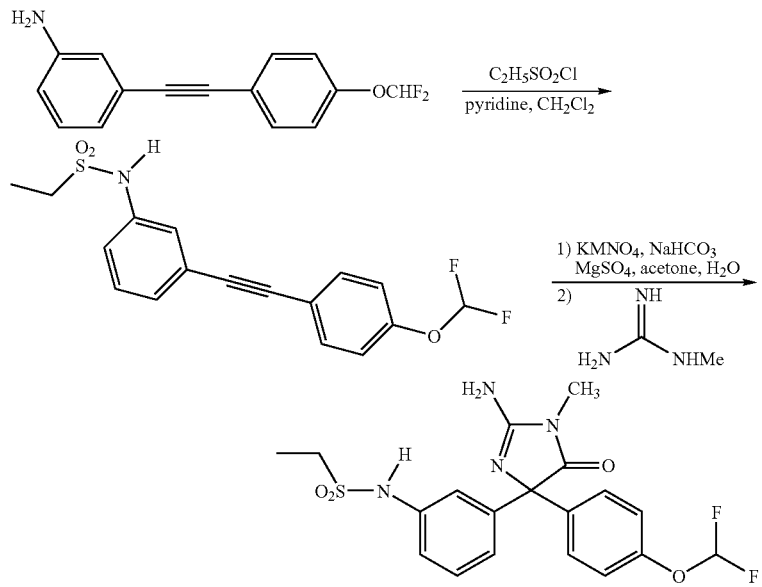

Step a) N-(3-{[4-(difluoromethoxy)phenyl]ethynyl}phenyl)ethanesulfonamide

A cold (0° C.) solution of 3-{[4-(difluoromethoxy)phenyl]ethynyl}aniline (0.5 g, 1.93 mmol) and pyridine (0.31 mL, 3.80 mmol) in $CH_2Cl_2$ was treated dropwise with ethylsulfonyl chloride (0.27 mL, 2.89 mmol). The mixture was stirred for 5 hours, poured into water and extracted with EtOAc/ethyl ether 1/1. The organic extracts were combined, dried over $MgSO_4$ and concentrated in vacuo. Purification of the resultant residue on silica gel (Biotage) using hexanes/EtOAc (3/1) as the eluting solvent gave N-(3-{[4-(difluoromethoxy)phenyl]ethynyl}phenyl)ethanesulfonamide as a yellow oil (0.62 g).

Step b) N-(3-{2-amino-4-[4-(difluoromethoxy)phenyl]-1-methyl-5-oxo-4,5-dihydro-1H-imidazol-4-yl}phenyl)ethanesulfonamide Using essentially the same procedure described in Example 12, steps c and d, and employing N-(3-{[4-(difluoromethoxy)phenyl]ethynyl}phenyl)ethanesulfonamide as starting material, the title compound was obtained as a white solid, identified by NMR and mass spectral analyses. $[M+H]^+$ 439.1

EXAMPLES 98-108

Preparation of N-(3-{2-Amino-4-[4-(difluoromethoxy)phenyl]-1-methyl-5-oxo-4,5-dihydro-1H-imidazol-4-yl}phenyl)sulfonamide Compounds

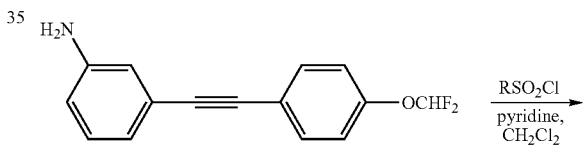

-continued

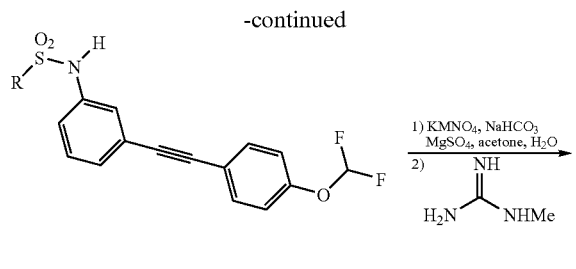

TABLE V

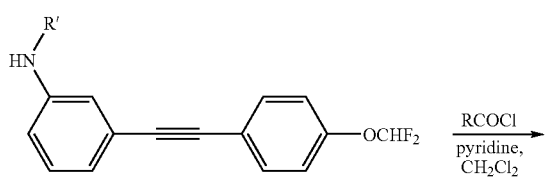

| Ex. No. | R | m/e [M + H]+ |
|---|---|---|
| 98 | 3,4-difluorophenyl | 523 |
| 99 | 3-methoxyphenyl | 517.1 |
| 100 | 3-chlorophenyl | 521 |
| 101 | n-propyl | 453.1 |
| 102 | 3-cyanophenyl | 512.1 |
| 103 | 3-(trifluoromethoxy)phenyl | 571.1 |
| 104 | 3-pyridyl | 488.1 |
| 105 | 4-cyanophenyl | 512.1 |
| 106 | 2-thienyl | 493 |
| 107 | benzyl | 501.1 |
| 108 | 3,5-difluorophenyl | 523.1 |

Using essentially the same procedure described in Example 97 and employing the desired sulfonyl chloride in step a, the compounds shown on Table V were obtained and identified by NMR and mass spectral analyses.

EXAMPLES 109-112

Preparation of N-(3-{2-Amino-4-[4-(difluoromethoxy)phenyl]-1-methyl-5-oxo-4,5-dihydro-1H-imidazol-4-yl}phenyl)acetamide Compounds

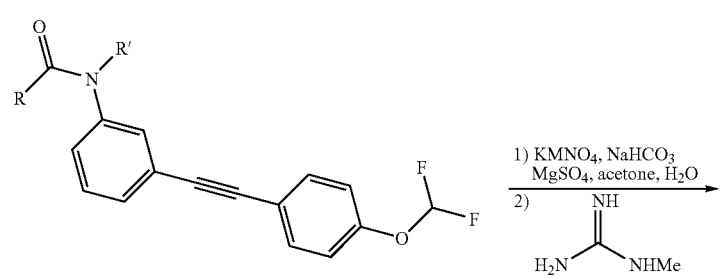

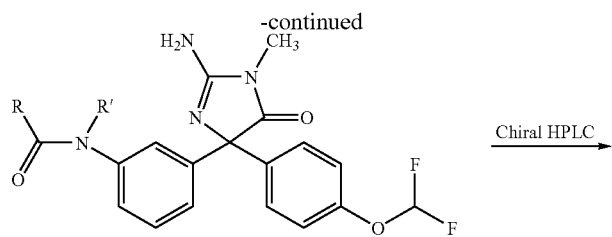

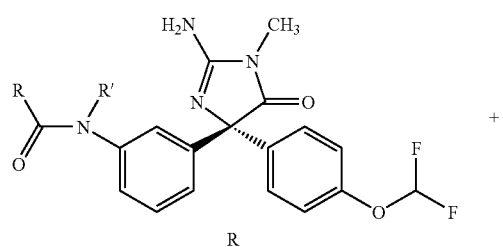

Using essentially the same procedure described in Example 97 and employing the appropriate acid chloride in step a, the compounds shown on Table VI were obtained and identified by NMR and mass spectral analyses. Chiral separation was achieved using essentially the same procedure described in Example 1, step d.

TABLE VI

| Ex. No. | Chiral | R | R' | [M + H] | $[\alpha]_D^{25*}$ |
|---|---|---|---|---|---|
| 109 | — | $CH_2OCH_3$ | H | 419.1 | |
| 110 | — | $CH_2OCH_3$ | $CH_3$ | 433.1 | |

TABLE VI-continued

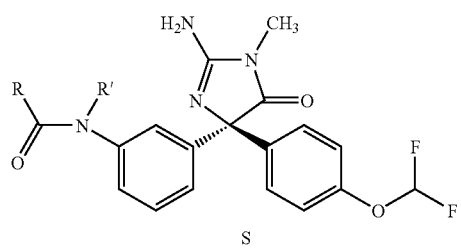

| Ex. No. | Chiral | R | R' | [M + H] | $[\alpha]_D^{25*}$ |
|---|---|---|---|---|---|
| 111 | 4-R | $CH_2OCH_3$ | H | 419.2 | +19.2 |
| 112 | 4-S | $CH_2OCH_3$ | H | 417.3** | −15.2 |

*1% Methanol Solution

**[M − H]⁻

EXAMPLE 113

Preparation of 2-Amino-5-[4-(difluoromethoxy)phenyl]-5-[3-(5-hydroxypent-1-yn-1-yl)phenyl]-3-methyl-3,5-dihydro-4H-imidazol-4-one

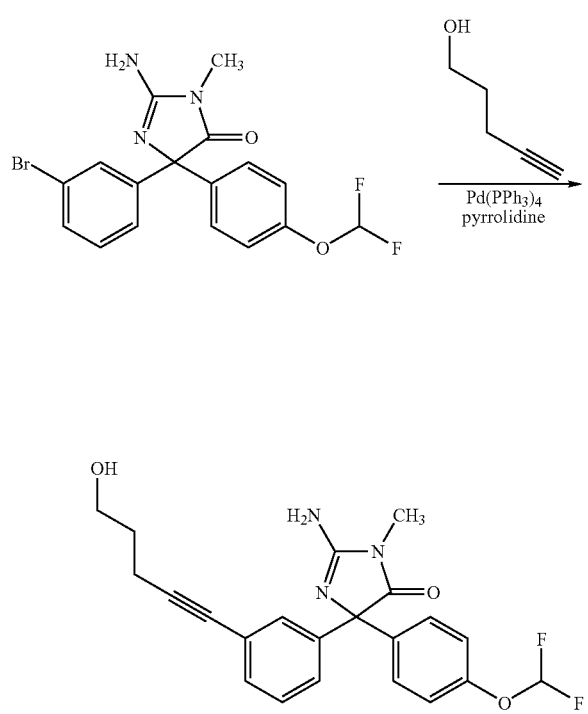

A mixture of 2-amino-5-(3-bromophenyl)-5-[4-(difluoromethoxy)phenyl]-3-methyl-3,5-dihydro-4H-imidazol-4-one (1.15 g, 2.8 mmol), dioxane, bis(benzonitrile)dichloropalladium(II) (32.2 mg, 0.084 mmol), tri-tert-butyl phosphine (10% w/w in hexane, 339 mg, 0.17 mmol) and diisopropyl amine (340 mg, 3.36 mmol) was degassed under argon for 5 minutes, treated with pent-4-yn-1-ol (236 mg, 2.8 mmol), stirred at 80° C. for 5 hours, poured into water and extracted with ethyl acetate. The organic extracts were combined, dried over MgSO$_4$ and concentrated in vacuo. Purification of the resultant residue by ICSO (EtOAc/MeOH 10/1) gave the title compound as a white solid (849 mg), identified by NMR and mass spectral analyses. MS m/e [M+H]$^+$ 414.2

EXAMPLES 114-173

Preparation of 2-Amino-5-[4-(difluoromethoxy)phenyl]-5-(3-alkynylphenyl)-3-methyl-3,5-dihydro-4H-imidazol-4-one Compounds

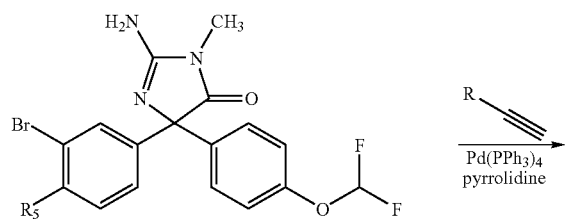

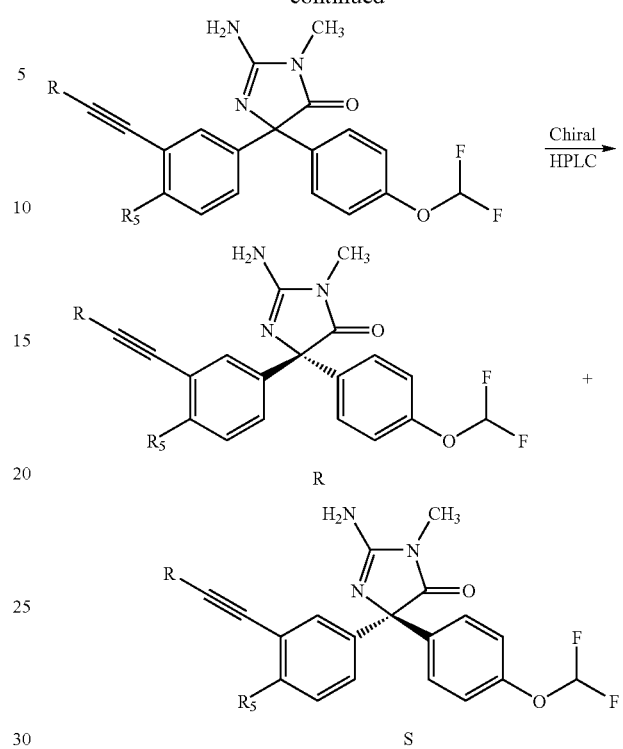

Using essentially the same procedure described in Example 113 and employing the desired alkyne reagent, the compounds shown on Table VII were obtained and identified by NMR and mass spectral analyses. Chiral separation was achieved using essentially the same procedure described in Example 1, step d.

TABLE VII

| Ex. No. | Chiral | R | R5 | m/e [M + H] | $[\alpha]_D^{25*}$ |
|---|---|---|---|---|---|
| 114 | — | CH$_2$CH$_2$CH$_2$F | H | 416.1 | |
| 115 | — | CH$_2$CH$_2$CH$_2$Cl | H | 432 | |
| 116 | — | CH$_2$CH$_2$CH$_3$ | H | 398.1 | |
| 117 | — | CH$_2$CH$_2$OH | H | 400.2 | |
| 118 | — | CH$_2$CH$_2$CH$_2$CH$_2$OH | H | 428.2 | |
| 119 | — | CH$_2$CH$_2$CH$_2$CH$_2$F | H | 430.2 | |
| 120 | — | CH$_2$CH$_2$Cl | H | 418 | |
| 121 | 5-R | CH$_2$CH$_3$ | H | 398 | +12.8 |
| 122 | 5-S | CH$_2$CH$_3$ | H | 398 | −9.8 |
| 123 | 5-S | CH$_2$CH$_2$CH$_2$OH | H | 414.1 | +12.4 |
| 124 | 5-R | CH$_2$CH$_2$CH$_2$OH | H | 428 | +10.2 |

TABLE VII-continued

[Structure shown: 2-amino-3-methyl-imidazolone with 3-(R-O-CH2)phenyl and 4-(OCHF2)phenyl substituents]

| Ex. No. | Chiral | R | R5 | m/e [M + H] | $[\alpha]_D^{25*}$ |
|---|---|---|---|---|---|
| 125 | 5-S | CH₂CH₂CH₂CH₂OH | H | 428 | −11.4 |
| 126 | 5-R | CH₂CH₂OH | H | 400 | |
| 127 | 5-S | CH₂CH₂OH | H | 400 | −13 |
| 128 | 5-S | CH₂CH₂CH₂F | H | 416.1 | −11.4 |
| 129 | 5-R | CH₂CH₂CH₂F | H | 416.1 | +19 |
| 130 | 5-S | CH₂CH₂CH₂OH | F | 432.1 | +11.6 |
| 131 | 5-R | CH₂CH₂CH₂OH | F | 432.1 | |
| 132 | 5-S | CH₂CH₂CH₂F | F | 432.1 | +8.6 |
| 133 | 5-R | CH₂CH₂CH₂F | F | 434.2 | −8.4 |
| 134 | — | CH₂CH₂OCH₃ | H | 414.1 | |
| 135 | — | CH₂OCH₃ | H | 400.1 | |
| 136 | 5-S | CH₂CH₂OCH₃ | H | 414.2 | −12 |
| 137 | 5-R | CH₂CH₂OCH₃ | H | 414.2 | +10.6 |
| 138 | — | CH₂CH₂F | H | 402.2 | |
| 139 | — | CH₂CH(CH₃)₂ | H | 412.2 | |
| 140 | — | CH(OH)CH₂CH₃ | H | 414.1 | |
| 141 | — | CH₂CH(OH)CH₃ | H | 414.2 | |
| 142 | — | CH(CH₃)₂ | H | 398.1 | |
| 143 | — | CH₂CH₃ | H | 384.2 | |
| 144 | — | CH₂CH₂CH₂CH₃ | H | 412.2 | |
| 145 | — | cyclopropyl | H | 396.2 | |
| 146 | — | cyclohexyl | H | 438.2 | |
| 147 | — | cyclopentylmethyl | H | 438.2 | |
| 148 | — | cyclohexylmethyl | H | 452.2 | |
| 149 | 5-S | CH₂OCH₃ | H | 400 | −6.8 |
| 150 | 5-R | CH₂OCH₃ | H | 400 | |
| 151 | — | CH₂OCH₃ | F | 418 | |
| 152 | — | CH₂CH₂OCH₃ | F | 432 | |
| 153 | — | CH₂OH | H | 386.1 | |
| 154 | — | (S)-CH(OH)CH₃ | H | 400.1 | |
| 155 | — | (R)-CH(OH)CH₃ | H | 400.1 | |
| 156 | — | CH(OH)CH(CH₃)₂ | H | 428.2 | |
| 157 | — | 1-hydroxycyclopentyl | H | 440.2 | |
| 158 | — | 1-hydroxycyclohexyl | H | 454.2 | |
| 159 | — | C(OH)(CH₃)₂ | H | 414.2 | |
| 160 | — | C(OH)(CH₃)CH₂CH₃ | H | 428.2 | |
| 161 | — | H | H | 356.1 | |
| 162 | — | (S)-CH(OH)C₆H₅ | H | 462.1 | |
| 163 | 5-S | CH₂CH₂OCH₃ | H | 432 | +7.8 |
| 164 | 5-R | CH₂CH₂OCH₃ | H | 432.1 | −6.6 |
| 165 | 5-S | CH₂OCH₃ | H | 418.1 | |
| 166 | 5-R | CH₂OCH₃ | H | 418.1 | |
| 167 | — | CH₃ | F | 388.1 | |
| 168 | — | CH₃ | H | 370.1 | |
| 169 | 5-R | (S)-CH(OH)CH₃ | H | 400.1 | −19.2 |
| 170 | 5-S | (S)-CH(OH)CH₃ | H | 400.1 | |
| 171 | 5-R | CH₃ | H | 370.1 | −15.6 |
| 172 | 5-S | CH₃ | H | 370.1 | +15 |
| 173 | 5-R | CH₂CH₂CH₂OH | H | 414.1 | |

*1% Methanol Solution
**[M − H]⁻

EXAMPLE 174

Preparation of 2-Amino-5-{3-[(E)-2-cyclopropylvinyl]phenyl}-5-[4-(difluoromethoxy)phenyl]-3-methyl-3,5-dihydro-4H-imidazol-4-one

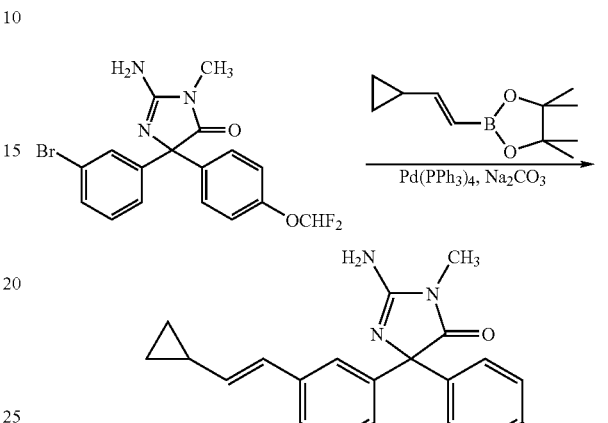

A mixture of 2-amino-5-(3-bromophenyl)-5-[4-(difluoromethoxy)phenyl]-3-methyl-3,5-dihydro-4H-imidazol-4-one (150 g, 0.36 mmol), dimethoxyethane, 2-[(E)-2-cyclopropylvinyl]-4,4,5,5-tetramethyl-1,3,2-dioxaborolane (105 mg) and Na₂CO₃ (2 M, 2.5 mL) was degassed under argon for 5 minutes and treated with tetrakis(triphenylphosphine)palladium(0) (21 mg, 0.018 mmol). The reaction mixture was stirred for 15 hour, poured into water and extracted with ethyl acetate. The extracts were combined, dried over MgSO₄ and concentrated in vacuo. Purification of the resultant residue by ICSO (EtOAc/MeOH 10/1) gave the title product as a white solid (98 mg), identified by NMR and mass spectral analyses.

EXAMPLES 175-187

Preparation of 2-Amino-5-[3-(2-substituted-vinyl)phenyl]-5-[4-(difluoromethoxy)phenyl]-3-methyl-3,5-dihydro-4H-imidazol-4-one Compounds

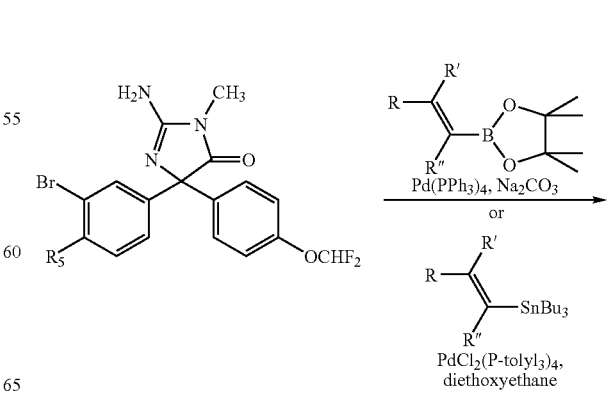

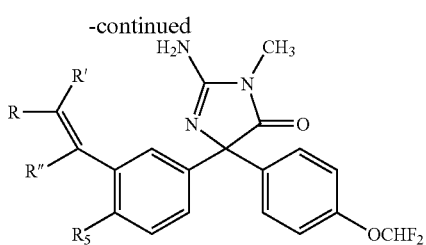

Using essentially the same procedure described in Example 174 and employing either the vinyldiborolane reagent or the vinyl tributyltin reagent, the compounds shown in Table VIII are obtained and identified by NMR and mass spectral analyses.

TABLE VIII

| Ex. No. | R | R' | R" | R5 | m/e [M + H] |
|---|---|---|---|---|---|
| 175 | $CH_3$ | H | H | H | 372.1 |
| 176 | $CH_3$ | H | H | F | 390.1 |
| 177 | H | H | H | H | 358.1 |
| 178 | $CH_3$ | $CH_3$ | H | F | 418 |
| 179 | H | H | $CH_3$ | H | 372.1 |
| 180 | $CH_2CH_2CH_3$ | H | H | H | 400.2 |
| 181 | $CH_2CH_2CH_2CH_2CH_3$ | H | H | H | 428.2 |
| 182 | $CH_2CH_2CH_{2Cl}$ | H | H | H | 434.1 |
| 183 | $C_6H_5$ | H | H | H | 434.2 |
| 184 | 2,4-difluorophenyl | H | H | H | 470.1 |
| 185 | $CH_2CH_2CH_2CH_2CH_2CH_3$ | H | H | H | 442.2 |
| 186 | H | H | $C_6H_5$ | H | 434.1 |
| 187 | $CH_2CH_2CH_2CH_3$ | H | H | H | 414.2 |

EXAMPLE 188

Evaluation of BACE1 Binding Affinity of Test Compounds

Fluorescent Kinetic Assays

Final Assay Conditions: 10 nM human BACE1 (or 10 nM Murine BACE1, 1.5 nM human BACE2), 25 μM substrate (WABC-6, MW 1549.6, from AnaSpec), Buffer: 50 mM Na-Acetate, pH 4.5, 0.05% CHAPS, 25% PBS, room temperature. Na-Acetate was from Aldrich, Cat.# 24, 124-5, CHAPS was from Research Organics, Cat. # 1304C 1×, PBS was from Mediatech (Celigro), Cat# 21-031-CV, peptide substrate AbzSEVNLDAEFRDpa was from AnaSpec, Peptide Name: WABC-6

Determination of stock substrate (AbzSEVNLDAEFRDpa) concentration: ~25 mM stock solution is made in DMSO using the peptide weight and MW, and diluted to ~25 μM (1:1000) in 1×PBS. Concentration is determined by absorbance at 354 nm using an extinction coefficient ε of 18172 $M^{-1}$ $cm^{-1}$, the concentration of stock substrate is corrected, and the substrate stock stored in small aliquots in −80° C.

[Substrate Stock]=$ABS^{354\ nm}*10^6/18172$ (in mM)

The extinction coefficient $\epsilon^{354\ nm}$ was adapted from TACE peptide substrate, which had the same quencher-fluorophore pair.

Determination of Stock Enzyme Concentration: the stock concentration of each enzyme is determined by absorbance at 280 nm using an ε of 64150 $M^{-1}$ $cm^{-1}$ for hBACE1 and MuBACE1, 62870 $M^{-1}$ $cm^{-1}$ for hBACE2 in 6 M Guanidinium Hydrochloride (from Research Organics, Cat. # 5134G-2), pH ~6. The extinction coefficient $\epsilon^{280\ nm}$ for each enzyme was calculated based on known amino acid composition and published extinction coefficients for Trp (5.69 $M^{-1}$ $cm^{-1}$) and Tyr (1.28 $M^{-1}$ $cm^{-1}$) residues (*Anal. Biochem.* 182, 319-326).

Dilution and mixing steps: total reaction volume: 100 μL
  2× inhibitor dilutions in buffer A (66.7 mM Na-Acetate, pH 4.5, 0.0667% CHAPS) were prepared,
  4× enzyme dilution in buffer A (66.7 mM Na-Acetate, pH 4.5, 0.0667% CHAPS) were prepared,
  100 μM substrate dilution in 1×PBS was prepared, and
  50 μL 2× Inhibitor, 25 μL 100 μM substrate are added to each well of 96-well plate (from DYNEX Technologies, VWR #: 11311-046), immediately followed by 25 μL 4× enzyme (added to the inhibitor and substrate mix), and the fluorescence readings are initiated.

Fluorescence Readings: Readings at $\lambda_{ex}$ 320 nm and $\lambda_{em}$ 420 nm are taken every 40 sec for 30 min at room temperature and the linear slope for substrate cleavage rate ($v_i$) determined.

Calculation of % Inhibition:

% Inhibition=$100*(1-v_i/v_0)$ $v_i$: substrate cleavage rate in the presence of inhibitor $v_0$: substrate cleavage rate in the absence of inhibitor $IC_{50}$ Determination:

% Inhibition=$((B*IC_{50}{}^n)+(100*I_0{}^n))/(IC_{50}{}^n+I_0{}^n)$ (Model # 39 from LSW Tool Bar in Excel where B is the % inhibition from the enzyme control, which should be close to 0.) % Inhibition is plotted vs. Inhibitor Concentration ($I_0$) and the data fit to the above equation to obtain $IC_{50}$ value and Hill number (n) for each compound. Testing at least 10 different inhibitor concentrations is preferred.

Results are shown in Table IX.

For Table IX

TABLE IX

| Example No. | BACE1 $IC_{50}$ μM |
|---|---|
| 1A | B |
| 1B | C |
| 2 | B |
| 3 | B |
| 4A | A |
| 4B | C |
| 5A | A |
| 5B | C |
| 6 | A |
| 7 | B |

TABLE IX-continued

| Example No. | BACE1 IC$_{50}$ μM |
|---|---|
| 8 | A |
| 9 | B |
| 10 | B |
| 11A | A |
| 11B | B |
| 12A | A |
| 12B | B |
| 13 | A |
| 14 | A |
| 15 | A |
| 16 | A |
| 17 | A |
| 18 | B |
| 19 | A |
| 20 | A |
| 21 | A |
| 22 | B |
| 23 | B |
| 24 | B |
| 25 | A |
| 26 | B |
| 27 | A |
| 28 | A |
| 29 | B |
| 30 | A |
| 31 | B |
| 32 | B |
| 33 | A |
| 34 | B |
| 35 | B |
| 36 | B |
| 37 | A |
| 38 | A |
| 39 | B |
| 40 | A |
| 41 | A |
| 42 | A |
| 43 | A |
| 44 | A |
| 45 | A |
| 46 | A |
| 47 | A |
| 48 | A |
| 49 | A |
| 50 | B |
| 51 | B |
| 52 | C |
| 53 | A |
| 54 | A |
| 55 | C |
| 56 | B |
| 57 | A |
| 58 | B |
| 59 | A |
| 60 | — |
| 61 | A |
| 62 | B |
| 63 | A |
| 64 | A |
| 65 | B |
| 66 | A |
| 67 | A |
| 68 | B |
| 69 | B |
| 70 | A |
| 79A | A |
| 81 | A |
| 97 | B |
| 98 | B |
| 99 | B |
| 100 | B |
| 101 | B |
| 102 | B |
| 103 | CB |
| 104 | B |
| 105 | B |
| 106 | B |
| 107 | B |
| 108 | C |
| 109 | A |
| 110 | B |
| 111 | A |
| 112 | B |
| 113 | A |
| 114 | A |
| 115 | A |
| 116 | A |
| 118 | — |
| 119 | — |
| 120 | A |
| 121 | A |
| 122 | C |
| 123 | B |
| 124 | A |
| 125 | — |
| 126 | A |
| 127 | C |
| 128 | C |
| 129 | A |
| 130 | C |
| 131 | A |
| 132 | B |
| 133 | A |
| 134 | A |
| 135 | A |
| 136 | C |
| 137 | A |
| 138 | A |
| 139 | A |
| 140 | A |
| 141 | A |
| 142 | A |
| 143 | A |
| 144 | A |
| 145 | A |
| 146 | B |
| 147 | B |
| 148 | C |
| 149 | B |
| 150 | A |
| 151 | A |
| 152 | A |
| 153 | A |
| 154 | A |
| 155 | A |
| 156 | B |
| 157 | B |
| 158 | B |
| 159 | A |
| 160 | B |
| 161 | B |
| 162 | B |
| 163 | C |
| 164 | A |
| 165 | C |
| 166 | A |
| 167 | B |
| 168 | A |
| 169 | — |
| 170 | A |
| 171 | — |
| 172 | A |
| 173 | |
| 174 | A |
| 175 | B |
| 176 | B |
| 177 | B |
| 178 | B |
| 179 | C |
| 180 | B |
| 181 | C |
| 182 | A |

TABLE IX-continued

| Example No. | BACE1 IC$_{50}$ μM |
|---|---|
| 183 | B |
| 184 | B |
| 185 | C |
| 186 | C |
| 187 | B |

What is claimed is:

1. A compound of formula I

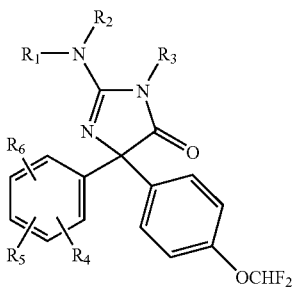

(I)

wherein $R_1$ and $R_2$ are each independently H or an alkyl, cycloalkyl, cycloheteroalkyl, aryl or heteroaryl group each optionally substituted or $R_1$ and $R_2$ may be taken together with the atom to which they are attached to form an optionally substituted 5- to 7-membered ring optionally interrupted by an additional heteroatom selected from O, N or S;

$R_3$ is H or an alkyl, cycloalkyl, cycloheteroalkyl, aryl or heteroaryl group each optionally substituted;

$R_4$, $R_5$ and $R_6$ are each independently H, Cl, I, F, NO$_2$, CN, COR$_7$, NR$_{10}$CO$_2$R$_{11}$, NR$_{15}$COR$_{16}$, OR$_{14}$, NR$_{12}$R$_{13}$, SO$_n$R$_{17}$ or an alkyl, haloalkyl, alkenyl, haloalkenyl, alkynyl, cycloalkyl or cycloheteroalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;

n is 0, 1 or 2;

$R_7$ and $R_{17}$ are each independently H, NR$_8$R$_9$ or an alkyl, haloalkyl, alkoxyalkyl, alkenyl, alkynyl, cycloalkyl or aryl group each optionally substituted;

$R_8$ and $R_9$ are each independently H or an alkyl, alkenyl, alkynyl or cycloalkyl group each optionally substituted or $R_8$ and $R_9$ may be taken together with the atom to which they are attached to form an optionally substituted 5- to 7-membered ring optionally containing an additional heteroatom selected from O, N or S;

$R_{11}$, $R_{14}$ and $R_{16}$ are each independently H or an alkyl, haloalkyl, alkoxyalkyl, alkenyl, alkynyl, cycloalkyl or aryl group each optionally substituted;

$R_{10}$ and $R_{15}$ are each independently H or an optionally substituted alkyl group; and $R_{12}$ and $R_{13}$ are each independently H or an alkyl or cycloalkyl group each optionally substituted or $R_{12}$ and $R_{13}$ may be taken together with the atom to which they are attached to form an optionally substituted 5- to 7-membered ring optionally containing an additional heteroatom selected from O, N or S; or a tautomer thereof, a stereoisomer thereof or a pharmaceutically acceptable salt thereof.

2. The compound according to claim 1 wherein $R_1$ and $R_2$ are H.

3. The compound according to claim 1 wherein $R_3$ is $C_1$-$C_4$alkyl.

4. The compound according to claim 1 wherein $R_4$, $R_5$ and $R_6$ are each independently H, Cl, I, F, COR$_7$, OR$_{14}$, or an alkyl, haloalkyl, alkoxy, haloalkoxy, alkynyl or cycloalkyl group each optionally substituted.

5. The compound according to claim 2 wherein $R_3$ is methyl.

6. The compound according to claim 4 wherein $R_5$ and $R_6$ are each independently H, Cl, I, or F.

7. The compound according to claim 5 wherein $R_4$ is H, COR$_7$, OR$_{14}$ or an alkyl, haloalkyl, alkoxy, haloalkoxy, alkynyl or cycloalkyl group each optionally substituted; and $R_4$ is at the 3-position of the phenyl ring.

8. The compound according to claim 7 wherein $R_5$ and $R_6$ are each independently H, Cl, I, or F.

9. The compound according to claim 1 selected from the group consisting of:

(5S)-2-Amino-5-[4-(difluoromethoxy)phenyl]-3-methyl-5-phenyl-3,5-dihydro-4H-imidazol-4-one;

(5R)-2-Amino-5-[4-(difluoromethoxy)-phenyl]-3-methyl-5-phenyl-3,5-dihydro-4H-imidazol-4-one;

(5R)-2-Amino-5-[4-(difluoromethoxy)phenyl]-3-methyl-5-(3-propylphenyl)-3,5-dihydro-4H-imidazol-4-one;

(5S)-2-Amino-5-[4-(difluoromethoxy)phenyl]-3-methyl-5-(3-propylphenyl)-3,5-dihydro-4H-imidazol-4-one;

2-Amino-5-[4-(difluoromethoxy)phenyl]-5-[3-(3-fluoropropyl)phenyl]-3-methyl-3,5-dihydro-4H-imidazol-4-one;

2-Amino-5-[4-(difluoromethoxy)phenyl]-5-[3-(3,3-difluoropropyl)phenyl]-3-methyl-3,5-dihydro-4H-imidazol-4-one;

2-Amino-5-[4-(difluoromethoxy)phenyl]-5-[3-(4-fluorobutyl)phenyl]-3-methyl-3,5-dihydro-4H-imidazol-4-one;

2-Amino-5-[3-(4,4-difluorobutyl)phenyl]-5-[4-(difluoromethoxy)phenyl]-3-methyl-3,5-dihydro-4H-imidazol-4-one;

2-Amino-5-[4-(difluoromethoxy)phenyl]-5-[3-(2-fluoroethyl)phenyl]-3-methyl-3,5-dihydro-4H-imidazol-4-one;

2-Amino-5-[3-(2,2-difluoroethyl)phenyl]-5-[4-(difluoromethoxy)phenyl]-3-methyl-3,5-dihydro-4H-imidazol-4-one;

2-Amino-5-[4-(difluoromethoxy)phenyl]-3-methyl-5-[3-(2,2,2-trifluoroethyl)phenyl]-3,5-dihydro-4H-imidazol-4-one;

2-Amino-5-[4-(difluoromethoxy)phenyl]-3-methyl-5-[3-(3,3,3-trifluoropropyl)phenyl]-3,5-dihydro-4H-imidazol-4-one;

2-Amino-5-[4-(difluoromethoxy)phenyl]-3-methyl-5-[3-(4,4,4-trifluorobutyl)phenyl]-3,5-dihydro-4H-imidazol-4-one;

(5R)-2-amino-5-(3-butylphenyl)-5-[4-(difluoromethoxy)phenyl]-3-methyl-3,5-dihydro-4H-imidazol-4-one;

(5S)-2-amino-5-(3-butylphenyl)-5-[4-(difluoromethoxy)phenyl]-3-methyl-3,5-dihydro-4H-imidazol-4-one;

2-Amino-5-[4-(difluoromethoxy)phenyl]-3-methyl-5-(3-pentylphenyl)-3,5-dihydro-4H-imidazol-4-one;

2-Amino-5-[4-(difluoromethoxy)phenyl]-3-methyl-5-[3-(2-methylbutyl)phenyl]-3,5-dihydro-4H-imidazol-4-one;

2-Amino-5-(3-but-3-en-1-ylphenyl)-5-[4-(difluoromethoxy)phenyl]-3-methyl-3,5-dihydro-4H-imidazol-4-one;

2-Amino-5-[3-(cyclopropylmethyl)phenyl]-5-[4-(difluoromethoxy)phenyl]-3-methyl-3,5-dihydro-4H-imidazol-4-one;

3-(3-{2-Amino-4-[4-(difluoromethoxy)phenyl]-1-methyl-5-oxo-4,5-dihydro-1H-imidazol-4-yl}phenyl)propanenitrile;

(5R)-2-Amino-5-[4-(difluoromethoxy)phenyl]-3-methyl-5-(3-pent-4-en-1-ylphenyl)-3,5-dihydro-4H-imidazol-4-one;

(5S)-2-Amino-5-[4-(difluoromethoxy)phenyl]-3-methyl-5-(3-pent-4-en-1-ylphenyl)-3,5-dihydro-4H-imidazol-4-one;

N-(3-{(4R)-2-Amino-4-[4-(difluoromethoxy)phenyl]-1-methyl-5-oxo-4,5-dihydro-1H-imidazol-4-yl}phenyl)-2-methoxyacetamide;

N-(3-{(4S)-2-Amino-4-[4-(difluoromethoxy)phenyl]-1-methyl-5-oxo-4,5-dihydro-1H-imidazol-4-yl}phenyl)-2-methoxyacetamide;

(5S)-2-amino-5-[4-(difluoromethoxy)phenyl]-3-methyl-5-phenyl-3,5-dihydro-4H-imidazol-4-one;

2-amino-5-[4-(difluoromethoxy)phenyl]-5-[3-(4-hydroxybut-1-yn-1-yl)phenyl]-3-methyl-3,5-dihydro-4H-imidazol-4-one;

2-amino-5-[4-(difluoromethoxy)phenyl]-5-[3-(4-hydroxybutyl)phenyl]-3-methyl-3,5-dihydro-4H-imidazol-4-one;

2-amino-5-[4-(difluoromethoxy)phenyl]-5-[3-(5-fluoropentyl)phenyl]-3-methyl-3,5-dihydro-4H-imidazol-4-one;

2-amino-5-[4-(difluoromethoxy)phenyl]-5-[3-(4-fluorobutyl)phenyl]-3-methyl-3,5-dihydro-4H-imidazol-4-one;

2-amino-5-[4-(difluoromethoxy)phenyl]-5-[3-(6-fluorohexyl)phenyl]-3-methyl-3,5-dihydro-4H-imidazol-4-one;

2-amino-5-[4-(difluoromethoxy)phenyl]-5-[3-(4-methoxybutyl)phenyl]-3-methyl-3,5-dihydro-4H-imidazol-4-one;

2-amino-5-[4-(difluoromethoxy)phenyl]-5-{3-[(1Z)-3-methoxyprop-1-en-1-yl]phenyl}-3-methyl-3,5-dihydro-4H-imidazol-4-one;

2-amino-5-[4-(difluoromethoxy)phenyl]-5-[3-(3-methoxypropyl)phenyl]-3-methyl-3,5-dihydro-4H-imidazol-4-one;

2-amino-5-[3-(4,4-difluorobutyl)phenyl]-5-[4-(difluoromethoxy)phenyl]-3-methyl-3,5-dihydro-4H-imidazol-4-one;

3-{2-amino-4-[4-(difluoromethoxy)phenyl]-1-methyl-5-oxo-4,5-dihydro-1H-imidazol-4-yl}-N-propylbenzamide;

2-amino-5-[4-(difluoromethoxy)phenyl]-5-{3-[(2-fluoroethoxy)methyl]phenyl}-3-methyl-3,5-dihydro-4H-imidazol-4-one;

2-amino-5-[4-(difluoromethoxy)phenyl]-3-methyl-5-{3-[(3,3,3-trifluoropropoxy)methyl]phenyl}-3,5-dihydro-4H-imidazol-4-one;

2-amino-5-[4-(difluoromethoxy)phenyl]-5-[3-(methoxymethyl)phenyl]-3-methyl-3,5-dihydro-4H-imidazol-4-one;

2-amino-5-[3-(butoxymethyl)phenyl]-5-[4-(difluoromethoxy)phenyl]-3-methyl-3,5-dihydro-4H-imidazol-4-one;

2-amino-5-{3-[(cyclopropylmethoxy)methyl]phenyl}-5-[4-(difluoromethoxy)phenyl]-3-methyl-3,5-dihydro-4H-imidazol-4-one;

2-amino-5-[4-(difluoromethoxy)phenyl]-5-[3-(ethoxymethyl)phenyl]-3-methyl-3,5-dihydro-4H-imidazol-4-one;

2-amino-5-[4-(difluoromethoxy)phenyl]-3-methyl-5-[3-(propoxymethyl)phenyl]-3,5-dihydro-4H-imidazol-4-one;

2-amino-5-[4-(difluoromethoxy)phenyl]-5-(3-{[2-fluoro-1-(fluoromethyl)ethoxy]methyl}phenyl)-3-methyl-3,5-dihydro-4H-imidazol-4-one;

2-amino-5-[4-(difluoromethoxy)phenyl]-3-methyl-5-{3-[(2,2,2-trifluoroethoxy)methyl]phenyl}-3,5-dihydro-4H-imidazol-4-one;

2-amino-5-[4-(difluoromethoxy)phenyl]-3-methyl-5-{3-[(2,2,3,3-tetrafluoropropoxy)methyl]phenyl}-3,5-dihydro-4H-imidazol-4-one;

4-[4-(difluoromethoxy)phenyl]-4-[3-(3-methoxyprop-1-yn-1-yl)phenyl]-1-methyl-4,5-dihydro-1H-imidazol-2-amine;

2-amino-5-[3-(1,4-difluorobutyl)phenyl]-5-[4-(difluoromethoxy)phenyl]-3-methyl-3,5-dihydro-4H-imidazol-4-one;

2-amino-5-[4-(difluoromethoxy)phenyl]-5-[3-(3-fluorobut-3-en-1-yl)phenyl]-3-methyl-3,5-dihydro-4H-imidazol-4-one;

2-amino-5-[3-(4,4-difluorobut-3-en-1-yl)phenyl]-5-[4-(difluoromethoxy)phenyl]-3-methyl-3,5-dihydro-4H-imidazol-4-one;

2-amino-5-[4-(difluoromethoxy)phenyl]-5-[3-(4,4,4-trifluorobutyl)phenyl]-3-methyl-3,5-dihydro-4H-imidazol-4-one;

5-(3-{2-amino-4-[4-(difluoromethoxy)phenyl]-1-methyl-5-oxo-4,5-dihydro-1H-imidazol-4-yl}phenyl)pentanenitrile;

4-(3-{2-amino-4-[4-(difluoromethoxy)phenyl]-1-methyl-5-oxo-4,5-dihydro-1H-imidazol-4-yl}phenyl)butanenitrile;

2-amino-5-{3-[(1E)-4,4-difluorobut-1-en-1-yl]phenyl}-5-[4-(difluoromethoxy)phenyl]-3-methyl-3,5-dihydro-4H-imidazol-4-one;

2-amino-5-[4-(difluoromethoxy)phenyl]-5-[3-(3-hydroxyhex-4-yn-1-yl)phenyl]-3-methyl-3,5-dihydro-4H-imidazol-4-one;

2-amino-5-[4-(difluoromethoxy)phenyl]-5-{3-[(1E)-6-methoxyhex-1-en-1-yl]phenyl}-3-methyl-3,5-dihydro-4H-imidazol-4-one;

2-amino-5-[4-(difluoromethoxy)phenyl]-5-{3-[(1E)-5-methoxypent-1-en-1-yl]phenyl}-3-methyl-3,5-dihydro-4H-imidazol-4-one;

2-amino-5-[4-(difluoromethoxy)phenyl]-5-{3-[2-(methoxymethyl)cyclopropyl]phenyl}-3-methyl-3,5-dihydro-4H-imidazol-4-one;

2-amino-5-[4-(difluoromethoxy)phenyl]-5-{3-[(1E)-5-hydroxypent-1-en-1-yl]phenyl}-3-methyl-3,5-dihydro-4H-imidazol-4-one;

2-amino-5-[4-(difluoromethoxy)phenyl]-5-{3-[(1E)-3-methoxyprop-1-en-1-yl]phenyl}-3-methyl-3,5-dihydro-4H-imidazol-4-one;

2-amino-5-[4-(difluoromethoxy)phenyl]-5-{3-[(1E)-4-methoxybut-1-en-1-yl]phenyl}-3-methyl-3,5-dihydro-4H-imidazol-4-one;

2-amino-5-[4-(difluoromethoxy)phenyl]-5-{3-[(1E)-4-hydroxybut-1-en-1-yl]phenyl}-3-methyl-3,5-dihydro-4H-imidazol-4-one;

2-amino-5-[4-(difluoromethoxy)phenyl]-5-{3-[2-(2-methoxyethyl)cyclopropyl]phenyl}-3-methyl-3,5-dihydro-4H-imidazol-4-one;

2-amino-5-[4-(difluoromethoxy)phenyl]-5-{3-[(1E)-4-fluorobut-1-en-1-yl]phenyl}-3-methyl-3,5-dihydro-4H-imidazol-4-one;

2-amino-5-[4-(difluoromethoxy)phenyl]-5-{3-[(1E)-5-fluoropent-1-en-1-yl]phenyl}-3-methyl-3,5-dihydro-4H-imidazol-4-one;

5-(3-acetylphenyl)-2-amino-5-[4-(difluoromethoxy)phenyl]-3-methyl-3,5-dihydro-4H-imidazol-4-one;

2-amino-5-[4-(difluoromethoxy)phenyl]-5-{4-fluoro-3-[(1E)-4-fluorobut-1-en-1-yl]phenyl}-3-methyl-3,5-dihydro-4H-imidazol-4-one;

2-amino-5-[4-(difluoromethoxy)phenyl]-5-[3-(3-fluoroprop-1-yn-1-yl)phenyl]-3-methyl-3,5-dihydro-4H-imidazol-4-one;

2-amino-5-[4-(difluoromethoxy)phenyl]-5-(3-hydroxyphenyl)-3-methyl-3,5-dihydro-4H-imidazol-4-one;

2-amino-5-[4-(difluoromethoxy)phenyl]-5-[3-(3-fluoropropoxy)phenyl]-3-methyl-3,5-dihydro-4H-imidazol-4-one;

2-amino-5-[3-(cyclopropylmethoxy)phenyl]-5-[4-(difluoromethoxy)phenyl]-3-methyl-3,5-dihydro-4H-imidazol-4-one;

2-amino-5-[4-(difluoromethoxy)phenyl]-3-methyl-5-[3-(4,4,4-trifluorobutoxy)phenyl]-3,5-dihydro-4H-imidazol-4-one;

2-amino-5-[3-(2,2-difluoroethoxy)phenyl]-5-[4-(difluoromethoxy)phenyl]-3-methyl-3,5-dihydro-4H-imidazol-4-one;

2-amino-5-[4-(difluoromethoxy)phenyl]-5-[3-(4-fluorobutoxy)phenyl]-3-methyl-3,5-dihydro-4H-imidazol-4-one;

2-amino-5-[4-(difluoromethoxy)phenyl]-3-methyl-5-[3-(3-phenoxypropoxy)phenyl]-3,5-dihydro-4H-imidazol-4-one;

4-(3-{2-amino-4-[4-(difluoromethoxy)phenyl]-1-methyl-5-oxo-4,5-dihydro-1H-imidazol-4-yl}phenoxy)butanenitrile;

2-amino-5-[4-(difluoromethoxy)phenyl]-5-[4-fluoro-3-(3-fluoropropoxy)phenyl]-3-methyl-3,5-dihydro-4H-imidazol-4-one;

2-amino-5-[3-(but-2-yn-1-yloxy)-4-fluorophenyl]-5-[4-(difluoromethoxy)phenyl]-3-methyl-3,5-dihydro-4H-imidazol-4-one;

2-amino-5-[4-(difluoromethoxy)phenyl]-5-[4-fluoro-3-(4-fluorobutoxy)phenyl]-3-methyl-3,5-dihydro-4H-imidazol-4-one;

2-amino-5-[3-(2,2-difluoroethoxy)-4-fluorophenyl]-5-[4-(difluoromethoxy)phenyl]-3-methyl-3,5-dihydro-4H-imidazol-4-one;

(5R)-2-amino-5-[4-(difluoromethoxy)phenyl]-5-[4-fluoro-3-(3-fluoropropoxy)phenyl]-3-methyl-3,5-dihydro-4H-imidazol-4-one;

(5S)-2-amino-5-[4-(difluoromethoxy)phenyl]-5-[4-fluoro-3-(3-fluoropropoxy)phenyl]-3-methyl-3,5-dihydro-4H-imidazol-4-one;

2-amino-5-{3-[(4,4-difluorobut-3-en-1-yl)oxy]phenyl}-5-[4-(difluoromethoxy)phenyl]-3-methyl-3,5-dihydro-4H-imidazol-4-one;

(5S)-2-amino-5-[3-(2,2-difluoroethoxy)-4-fluorophenyl]-5-[4-(difluoromethoxy)phenyl]-3-methyl-3,5-dihydro-4H-imidazol-4-one;

(5R)-2-amino-5-[3-(2,2-difluoromethoxy)-4-fluorophenyl]-5-[4-(difluoromethoxy)phenyl]-3-methyl-3,5-dihydro-4H-imidazol-4-one;

2-amino-5-[4-(difluoromethoxy)phenyl]-5-[3-(2-fluoroethyl)phenyl]-3-methyl-3,5-dihydro-4H-imidazol-one;

2-amino-5-[4-(difluoromethoxy)phenyl]-5-[3-(5-fluoropentanoyl)phenyl]-3-methyl-3,5-dihydro-4H-imidazol-4-one;

2-amino-5-[4-(difluoromethoxy)phenyl]-5-[3-(4-fluorobutanoyl)phenyl]-3-methyl-3,5-dihydro-4H-imidazol-4-one;

2-amino-5-[3-(but-3-en-1-yloxy)phenyl]-5-[4-(difluoromethoxy)phenyl]-3-methyl-3,5-dihydro-4H-imidazol-4-one;

2-amino-5-[3-(but-3-en-1-yloxy)-4-fluorophenyl]-5-[4-(difluoromethoxy)phenyl]-3-methyl-3,5-dihydro-4H-imidazol-4-one;

(5R)-2-amino-5-[3-(but-3-en-1-yloxy)phenyl]-5-[4-(difluoromethoxy)phenyl]-3-methyl-3,5-dihydro-4H-imidazol-4-one;

(5S)-2-amino-5-[3-(but-3-en-1-yloxy)phenyl]-5-[4-(difluoromethoxy)phenyl]-3-methyl-3,5-dihydro-4H-imidazol-4-one;

2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one;

2-amino-5-[4-(difluoromethoxy)phenyl]-5-(4-fluoro-3-pent-4-en-1-ylphenyl)-3-methyl-3,5-dihydro-4H-imidazol-4-one;

2-amino-5-(3-but-3-en-1-yl-4-fluorophenyl)-5-[4-(difluoromethoxy)phenyl]-3-methyl-3,5-dihydro-4H-imidazol-4-one;

3-{2-amino-4-[4-(difluoromethoxy)phenyl]-1-methyl-5-oxo-4,5-dihydro-1H-imidazol-4-yl}benzaldehyde;

2-amino-5-[4-(difluoromethoxy)phenyl]-5-[3-(1-hydroxybut-2-yn-1-yl)phenyl]-3-methyl-3,5-dihydro-4H-imidazol-4-one;

2-amino-5-[4-(difluoromethoxy)phenyl]-5-[3-(1,4-dihydroxybut-2-yn-1-yl)phenyl]-3-methyl-3,5-dihydro-4H-imidazol-4-one;

(5R)-2-amino-5-[3-(difluoromethoxy)phenyl]-5-[4-(difluoromethoxy)phenyl]-3-methyl-3,5-dihydro-4H-imidazol-4-one;

2-amino-5-[4-(difluoromethoxy)phenyl]-5-[3-(2,2-dimethyl-3-oxocyclobutyl)phenyl]-3-methyl-3,5-dihydro-4H-imidazol-4-one;

2-amino-5-[4-(difluoromethoxy)phenyl]-3-methyl-5-[3-(3-oxocyclobutyl)phenyl]-3,5-dihydro-4H-imidazol-4-one;

2-amino-5-[4-(difluoromethoxy)phenyl]-5-[3-(3-hydroxycyclobutyl)phenyl]-3-methyl-3,5-dihydro-4H-imidazol-4-one;

methyl [3-(3-{2-amino-4-[4-(difluoromethoxy)phenyl]-1-methyl-5-oxo-4,5-dihydro-1H-imidazol-4-yl}phenyl)cyclobutyl]acetate; and methyl (3-(3-{2-amino-4-[4-(difluoromethoxy)phenyl]-1-methyl-5-oxo-4,5-dihydro-1H-imidazol-4-yl}phenyl)cyclobutylidene]acetate;

a tautomer thereof;

a stereoisomer thereof; and a pharmaceutically acceptable salt thereof.

10. A pharmaceutical composition which comprises a pharmaceutically acceptable carrier and an effective amount of a compound of formula I

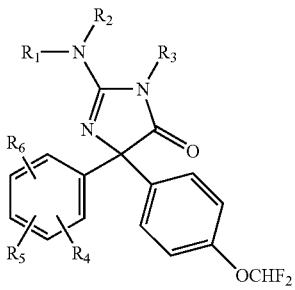

wherein
- $R_1$ and $R_2$ are each independently H or an alkyl, cycloalkyl, cycloheteroalkyl, aryl or heteroaryl group each optionally substituted or $R_1$ and $R_2$ may be taken together with the atom to which they are attached to form an optionally substituted 5- to 7-membered ring optionally interrupted by an additional heteroatom selected from O, N or S;
- $R_3$ is H or an alkyl, cycloalkyl, cycloheteroalkyl, aryl or heteroaryl group each optionally substituted;
- $R_4$, $R_5$ and $R_6$ are each independently H, halogen, $NO_2$, CN, $COR_7$, $NR_{10}CO_2R_{11}$, $NR_{15}COR_{16}$, $OR_{14}$, $NR_{12}R_{13}$, $SO_nR_{17}$ or an alkyl, haloalkyl, alkenyl, haloalkenyl, alkynyl, cycloalkyl or cycloheteroalkyl group each optionally substituted or when attached to adjacent carbon atoms $R_4$ and $R_5$ may be taken together with the atoms to which they are attached to form an optionally substituted 5- to 7-membered ring optionally containing one or two heteroatoms selected from O, N or S;
- n is 0, 1 or 2;
- $R_7$ and $R_{17}$ are each independently H, $NR_8R_9$ or an alkyl, haloalkyl, alkoxyalkyl, alkenyl, alkynyl, cycloalkyl or aryl group each optionally substituted;
- $R_8$ and $R_9$ are each independently H or an alkyl, alkenyl, alkynyl or cycloalkyl group each optionally substituted or $R_8$ and $R_9$ may be taken together with the atom to which they are attached to form an optionally substituted 5- to 7-membered ring optionally containing an additional heteroatom selected from O, N or S;
- $R_{11}$, $R_{14}$ and $R_{16}$ are each independently H or an alkyl, haloalkyl, alkoxyalkyl, alkenyl, alkynyl, cycloalkyl or aryl group each optionally substituted;
- $R_{10}$ and $R_{15}$ are each independently H or an optionally substituted alkyl group; and
- $R_{12}$ and $R_{13}$ are each independently H or an alkyl or cycloalkyl group each optionally substituted or $R_{12}$ and $R_{13}$ may be taken together with the atom to which are attached to form an optionally substituted 5- to 7-membered ring optionally containing an additional heteroatom selected from O, N or S; or a tautomer thereof, a stereoisomer thereof or a pharmaceutically acceptable salt thereof.

11. The composition according to claim 10 having a formula I compound wherein $R_1$ and $R_2$ are H.

12. The composition according to claim 11 having a formula I compound wherein $R_3$ is $C_1$-$C_4$alkyl.

13. The composition according to claim 12 having a formula I compound wherein $R_4$, $R_5$ and $R_6$ are each independently H, halogen, $COR_7$, $OR_{14}$, or an alkyl, haloalkyl, alkoxy, haloalkoxy, alkynyl or cycloalkyl group each optionally substituted.

14. The composition according to claim 13 having a formula I compound wherein $R_4$ is at the 3-position of the phenyl ring; and $R_5$ and $R_6$ are each independently H or halogen.

15. The composition according to claim 10 having a formula I compound selected from the group consisting of:
- (5S)-2-Amino-5-[4-(difluoromethoxy)phenyl]-3-methyl-5-phenyl-3,5-dihydro-4H-imidazol-4-one;
- (5R)-2-Amino-5-[4-(difluoromethoxy)-phenyl]-3-methyl-5-phenyl-3,5-dihydro-4H-imidazol-4-one;
- (5R)-2-Amino-5-[4-(difluoromethoxy)phenyl]-3-methyl-5-(3-propylphenyl)-3,5-dihydro-4H-imidazol-4-one;
- (5S)-2-Amino-5-[4-(difluoromethoxy)phenyl]-3-methyl-5-(3-propylphenyl)-3,5-dihydro-4H-imidazol-4-one;
- 2-Amino-5-[4-(difluoromethoxy)phenyl]-5-[3-(3-fluoropropyl)phenyl]-3-methyl-3,5-dihydro-4H-imidazol-4-one;
- 2-Amino-5-[4-(difluoromethoxy)phenyl]-5-[3-(3,3-difluoropropyl)phenyl]-3-methyl-3,5-dihydro-4H-imidazol-4-one;
- 2-Amino-5-[4-(difluoromethoxy)phenyl]-5-[3-(4-fluorobutyl)phenyl]-3-methyl-3,5-dihydro-4H-imidazol-4-one;
- 2-Amino-5-[3-(4,4-difluorobutyl)phenyl]-5-[4-(difluoromethoxy)phenyl]-3-methyl-3,5-dihydro-4H-imidazol-4-one;
- 2-Amino-5-[4-(difluoromethoxy)phenyl]-5-[3-(2-fluoroethyl)phenyl]-3-methyl-3,5-dihydro-4H-imidazol-4-one;
- 2-Amino-5-[3-(2,2-difluoroethyl)phenyl]-5-[4-(difluoromethoxy)phenyl]-3-methyl-3,5-dihydro-4H-imidazol-4-one;
- 2-Amino-5-[4-(difluoromethoxy)phenyl]-3-methyl-5-[3-(2,2,2-trifluoroethyl)phenyl]-3,5-dihydro-4H-imidazol-4-one;
- 2-Amino-5-[4-(difluoromethoxy)phenyl]-3-methyl-5-[3-(3,3,3-trifluoropropyl)phenyl]-3,5-dihydro-4H-imidazol-4-one;
- 2-Amino-5-[4-(difluoromethoxy)phenyl]-3-methyl-5-[3-(4,4,4-trifluorobutyl)phenyl]-3,5-dihydro-4H-imidazol-4-one;
- (5R)-2-amino-5-(3-butylphenyl)-5-[4-(difluoromethoxy)phenyl]-3-methyl-3,5-dihydro-4H-imidazol-4-one;
- (5S)-2-amino-5-(3-butylphenyl)-5-[4-(difluoromethoxy)phenyl]-3-methyl-3,5-dihydro-4H-imidazol-4-one;
- 2-Amino-5-[4-(difluoromethoxy)phenyl]-3-methyl-5-(3-pentylphenyl)-3,5-dihydro-4H-imidazol-4-one;
- 2-Amino-5-[4-(difluoromethoxy)phenyl]-3-methyl-5-[3-(2-methylbutyl)phenyl]-3,5-dihydro-4H-imidazol-4-one;
- 2-Amino-5-(3-but-3-en-1-ylphenyl)-5-[4-(difluoromethoxy)phenyl]-3-methyl-3,5-dihydro-4H-imidazol-4-one;
- 2-Amino-5-[3-(cyclopropylmethyl)phenyl]-5-[4-(difluoromethoxy)phenyl]-3-methyl-3,5-dihydro-4H-imidazol-4-one;
- 3-(3-{2-Amino-4-[4-(difluoromethoxy)phenyl]-1-methyl-5-oxo-4,5-dihydro-1H-imidazol-4-yl}phenyl)propanenitrile;
- (5R)-2-Amino-5-[4-(difluoromethoxy)phenyl]-3-methyl-5-(3-pent-4-en-1-ylphenyl)-3,5-dihydro-4H-imidazol-4-one;
- (5S)-2-Amino-5-[4-(difluoromethoxy)phenyl]-3-methyl-5-(3-pent-4-en-1-ylphenyl)-3,5-dihydro-4H-imidazol-4-one;
- N-(3-{(4R)-2-Amino-4-[4-(difluoromethoxy)phenyl]-1-methyl-5-oxo-4,5-dihydro-1H-imidazol-4-yl}phenyl)-2-methoxyacetamide;

N-(3-{(4S)-2-Amino-4-[4-(difluoromethoxy)phenyl]-1-methyl-5-oxo-4,5-dihydro-1H-imidazol-4-yl}phenyl)-2-methoxyacetamide;

(5S)-2-amino-5-[4-(difluoromethoxy)phenyl]-3-methyl-5-phenyl-3,5-dihydro-4H-imidazol-4-one;

2-amino-5-[4-(difluoromethoxy)phenyl]-5-[3-(4-hydroxybut-1-yn-1-yl)phenyl]-3-methyl-3,5-dihydro-4H-imidazol-4-one;

2-amino-5-[4-(difluoromethoxy)phenyl]-5-[3-(4-hydroxybutyl)phenyl]-3-methyl-3,5-dihydro-4H-imidazol-4-one;

2-amino-5-[4-(difluoromethoxy)phenyl]-5-[3-(5-fluoropentyl)phenyl]-3-methyl-3,5-dihydro-4H-imidazol-4-one;

2-amino-5-[4-(difluoromethoxy)phenyl]-5-[3-(4-fluorobutyl)phenyl]-3-methyl-3,5-dihydro-4H-imidazol-4-one;

2-amino-5-[4-(difluoromethoxy)phenyl]-5-[3-(6-fluorohexyl)phenyl]-3-methyl-3,5-dihydro-4H-imidazol-4-one;

2-amino-5-[4-(difluoromethoxy)phenyl]-5-[3-(4-methoxybutyl)phenyl]-3-methyl-3,5-dihydro-4H-imidazol-4-one;

2-amino-5-[4-(difluoromethoxy)phenyl]-5-{3-[(1Z)-3-methoxyprop-1-en-1-yl]phenyl}-3-methyl-3,5-dihydro-4H-imidazol-4-one;

2-amino-5-[4-(difluoromethoxy)phenyl]-5-[3-(3-methoxypropyl)phenyl]-3-methyl-3,5-dihydro-4H-imidazol-4-one;

2-amino-5-[3-(4,4-difluorobutyl)phenyl]-5-[4-(difluoromethoxy)phenyl]-3-methyl-3,5-dihydro-4H-imidazol-4-one;

3-{2-amino-4-[4-(difluoromethoxy)phenyl]-1-methyl-5-oxo-4,5-dihydro-1H-imidazol-4-yl}-N-propylbenzamide;

2-amino-5-[4-(difluoromethoxy)phenyl]-5-{3-[(2-fluoroethoxy)methyl]phenyl}-3-methyl-3,5-dihydro-4H-imidazol-4-one;

2-amino-5-[4-(difluoromethoxy)phenyl]-3-methyl-5-{3-[(3,3,3-trifluoropropoxy)methyl]phenyl}-3,5-dihydro-4H-imidazol-4-one;

2-amino-5-[4-(difluoromethoxy)phenyl]-5-[3-(methoxymethyl)phenyl]-3-methyl-3,5-dihydro-4H-imidazol-4-one;

2-amino-5-[3-(butoxymethyl)phenyl]-5-[4-(difluoromethoxy)phenyl]-3-methyl-3,5-dihydro-4H-imidazol-4-one;

2-amino-5-{3-[(cyclopropylmethoxy)methyl]phenyl}-5-[4-(difluoromethoxy)phenyl]-3-methyl-3,5-dihydro-4H-imidazol-4-one;

2-amino-5-[4-(difluoromethoxy)phenyl]-5-[3-(ethoxymethyl)phenyl]-3-methyl-3,5-dihydro-4H-imidazol-4-one;

2-amino-5-[4-(difluoromethoxy)phenyl]-3-methyl-5-[3-(propoxymethyl)phenyl]-3,5-dihydro-4H-imidazol-4-one;

2-amino-5-[4-(difluoromethoxy)phenyl]-5-(3-{[2-fluoro-1-(fluoromethyl)ethoxy]methyl}phenyl)-3-methyl-3,5-dihydro-4H-imidazol-4-one;

2-amino-5-[4-(difluoromethoxy)phenyl]-3-methyl-5-{3-[(2,2,2-trifluoroethoxy)methyl]phenyl}-3,5-dihydro-4H-imidazol-4-one;

2-amino-5-[4-(difluoromethoxy)phenyl]-3-methyl-5-{3-[(2,2,3,3-tetrafluoropropoxy)methyl]phenyl}-3,5-dihydro-4H-imidazol-4-one;

4-[4-(difluoromethoxy)phenyl]-4-[3-(3-methoxyprop-1-yn-1-yl)phenyl]-1-methyl-4,5-dihydro-1H-imidazol-2-amine;

2-amino-5-[3-(1,4-difluorobutyl)phenyl]-5-[4-(difluoromethoxy)phenyl]-3-methyl-3,5-dihydro-4H-imidazol-4-one;

2-amino-5-[4-(difluoromethoxy)phenyl]-5-[3-(3-fluorobut-3-en-1-yl)phenyl]-3-methyl-3,5-dihydro-4H-imidazol-4-one;

2-amino-5-[3-(4,4-difluorobut-3-en-1-yl)phenyl]-5-[4-(difluoromethoxy)phenyl]-3-methyl-3,5-dihydro-4H-imidazol-4-one;

2-amino-5-[4-(difluoromethoxy)phenyl]-3-methyl-5-[3-(4,4,4-trifluorobutyl)phenyl]-3,5-dihydro-4H-imidazol-4-one;

5-(3-{2-amino-4-[4-(difluoromethoxy)phenyl]-1-methyl-5-oxo-4,5-dihydro-1H-imidazol-4-yl}phenyl)pentanenitrile;

4-(3-{2-amino-4-[4-(difluoromethoxy)phenyl]-1-methyl-5-oxo-4,5-dihydro-1H-imidazol-4-yl}phenyl)butanenitrile;

2-amino-5-{3-[(1E)-4,4-difluorobut-1-en-1-yl]phenyl}-5-[4-(difluoromethoxy)phenyl]-3-methyl-3,5-dihydro-4H-imidazol-4-one;

2-amino-5-[4-(difluoromethoxy)phenyl]-5-[3-(3-hydroxyhex-4-yn-1-yl)phenyl]-3-methyl-3,5-dihydro-4H-imidazol-4-one;

2-amino-5-[4-(difluoromethoxy)phenyl]-5-{3-[(1E)-6-methoxyhex-1-en-1-yl]phenyl}-3-methyl-3,5-dihydro-4H-imidazol-4-one;

2-amino-5-[4-(difluoromethoxy)phenyl]-5-{3-[(1E)-5-methoxypent-1-en-1-yl]phenyl}-3-methyl-3,5-dihydro-4H-imidazol-4-one;

2-amino-5-[4-(difluoromethoxy)phenyl]-5-{3-[2-(methoxymethyl)cyclopropyl]phenyl}-3-methyl-3,5-dihydro-4H-imidazol-4-one;

2-amino-5-[4-(difluoromethoxy)phenyl]-5-{3-[(1E)-5-hydroxypent-1-en-1-yl]phenyl}-3-methyl-3,5-dihydro-4H-imidazol-4-one;

2-amino-5-[4-(difluoromethoxy)phenyl]-5-{3-[(1E)-3-methoxyprop-1-en-1-yl]phenyl}-3-methyl-3,5-dihydro-4H-imidazol-4-one;

2-amino-5-[4-(difluoromethoxy)phenyl]-5-{3-[(1E)-4-methoxybut-1-en-1-yl]phenyl}-3-methyl-3,5-dihydro-4H-imidazol-4-one;

2-amino-5-[4-(difluoromethoxy)phenyl]-5-{3-[(1E)-4-hydroxybut-1-en-1-yl]phenyl}-3-methyl-3,5-dihydro-4H-imidazol-4-one;

2-amino-5-[4-(difluoromethoxy)phenyl]-5-{3-[2-(2-methoxyethyl)cyclopropyl]phenyl}-3-methyl-3,5-dihydro-4H-imidazol-4-one;

2-amino-5-[4-(difluoromethoxy)phenyl]-5-{3-[(1E)-4-fluorobut-1-en-1-yl]phenyl}-3-methyl-3,5-dihydro-4H-imidazol-4-one;

2-amino-5-[4-(difluoromethoxy)phenyl]-5-{3-[(1E)-5-fluoropent-1-en-1-yl]phenyl}-3-methyl-3,5-dihydro-4H-imidazol-4-one;

5-(3-acetylphenyl)-2-amino-5-[4-(difluoromethoxy)phenyl]-3-methyl-3,5-dihydro-4H-imidazol-4-one;

2-amino-5-[4-(difluoromethoxy)phenyl]-5-{4-fluoro-3-[(1E)-4-fluorobut-1-en-1-yl]phenyl}-3-methyl-3,5-dihydro-4H-imidazol-4-one;

2-amino-5-[4-(difluoromethoxy)phenyl]-5-[3-(3-fluoroprop-1-yn-1-yl)phenyl]-3-methyl-3,5-dihydro-4H-imidazol-4-one;

2-amino-5-[4-(difluoromethoxy)phenyl]-5-(3-hydroxyphenyl)-3-methyl-3,5-dihydro-4H-imidazol-4-one;

2-amino-5-[4-(difluoromethoxy)phenyl]-5-[3-(3-fluoropropoxy)phenyl]-3-methyl-3,5-dihydro-4H-imidazol-4-one;

2-amino-5-[3-(cyclopropylmethoxy)phenyl]-5-[4-(difluoromethoxy)phenyl]-3-methyl-3,5-dihydro-4H-imidazol-4-one;

2-amino-5-[4-(difluoromethoxy)phenyl]-3-methyl-5-[3-(4,4,4-trifluorobutoxy)phenyl]-3,5-dihydro-4H-imidazol-4-one;

2-amino-5-[3-(2,2-difluoroethoxy)phenyl]-5-[4-(difluoromethoxy)phenyl]-3-methyl-3,5-dihydro-4H-imidazol-4-one;

2-amino-5-[4-(difluoromethoxy)phenyl]-5-[3-(4-fluorobutoxy)phenyl]-3-methyl-3,5-dihydro-4H-imidazol-4-one;

2-amino-5-[4-(difluoromethoxy)phenyl]-3-methyl-5-[3-(3-phenoxypropoxy)phenyl]-3,5-dihydro-4H-imidazol-4-one;

4-(3-{2-amino-4-[4-(difluoromethoxy)phenyl]-1-methyl-5-oxo-4,5-dihydro-1H-imidazol-4-yl}phenoxy)butanenitrile;

2-amino-5-[4-(difluoromethoxy)phenyl]-5-[4-fluoro-3-(3-fluoropropoxy)phenyl]-3-methyl-3,5-dihydro-4H-imidazol-4-one;

2-amino-5-[3-(but-2-yn-1-yloxy)-4-fluorophenyl]-5-[4-(difluoromethoxy)phenyl]-3-methyl-3,5-dihydro-4H-imidazol-4-one;

2-amino-5-[4-(difluoromethoxy)phenyl]-5-[4-fluoro-3-(4-fluorobutoxy)phenyl]-3-methyl-3,5-dihydro-4H-imidazol-4-one;

2-amino-5-[3-(2,2-difluoroethoxy)-4-fluorophenyl]-5-[4-(difluoromethoxy)phenyl]-3-methyl-3,5-dihydro-4H-imidazol-4-one;

(5R)-2-amino-5-[4-(difluoromethoxy)phenyl]-5-[4-fluoro-3-(3-fluoropropoxy)phenyl]-3-methyl-3,5-dihydro-4H-imidazol-4-one;

(5S)-2-amino-5-[4-(difluoromethoxy)phenyl]-5-[4-fluoro-3-(3-fluoropropoxy)phenyl]-3-methyl-3,5-dihydro-4H-imidazol-4-one;

2-amino-5-{3-[(4,4-difluorobut-3-en-1-yl)oxy]phenyl}-5-[4-(difluoromethoxy)phenyl]-3-methyl-3,5-dihydro-4H-imidazol-4-one;

(5S)-2-amino-5-[3-(2,2-difluoroethoxy)-4-fluorophenyl]-5-[4-(difluoromethoxy)phenyl]-3-methyl-3,5-dihydro-4H-imidazol-4-one;

(5R)-2-amino-5-[3-(2,2-difluoromethoxy)-4-fluorophenyl]-5-[4-(difluoromethoxy)phenyl]-3-methyl-3,5-dihydro-4H-imidazol-4-one;

2-amino-5-[4-(difluoromethoxy)phenyl]-5-[3-(2-fluoroethyl)phenyl]-3-methyl-3,5-dihydro-4H-imidazol-one;

2-amino-5-[4-(difluoromethoxy)phenyl]-5-[3-(5-fluoropentanoyl)phenyl]-3-methyl-3,5-dihydro-4H-imidazol-4-one;

2-amino-5-[4-(difluoromethoxy)phenyl]-5-[3-(4-fluorobutanoyl)phenyl]-3-methyl-3,5-dihydro-4H-imidazol-4-one;

2-amino-5-[3-(but-3-en-1-yloxy)phenyl]-5-[4-(difluoromethoxy)phenyl]-3-methyl-3,5-dihydro-4H-imidazol-4-one;

2-amino-5-[3-(but-3-en-1-yloxy)-4-fluorophenyl]-5-[4-(difluoromethoxy)phenyl]-3-methyl-3,5-dihydro-4H-imidazol-4-one;

(5R)-2-amino-5-[3-(but-3-en-1-yloxy)phenyl]-5-[4-(difluoromethoxy)phenyl]-3-methyl-3,5-dihydro-4H-imidazol-4-one;

(5S)-2-amino-5-[3-(but-3-en-1-yloxy)phenyl]-5-[4-(difluoromethoxy)phenyl]-3-methyl-3,5-dihydro-4H-imidazol-4-one;

2-amino-5-{3-[(4,4-difluorobut-3-en-1-yl)oxy]-4-fluorophenyl}-5-[4-(difluoromethoxy)phenyl]-3-methyl-3,5-dihydro-4H-imidazol-4-one;

2-amino-5-[4-(difluoromethoxy)phenyl]-5-(4-fluoro-3-pent-4-en-1-ylphenyl)-3-methyl-3,5-dihydro-4H-imidazol-4-one;

2-amino-5-(3-but-3-en-1-yl-4-fluorophenyl)-5-[4-(difluoromethoxy)phenyl]-3-methyl-3,5-dihydro-4H-imidazol-4-one;

3-{2-amino-4-[4-(difluoromethoxy)phenyl]-1-methyl-5-oxo-4,5-dihydro-1H-imidazol-4-yl}benzaldehyde;

2-amino-5-[4-(difluoromethoxy)phenyl]-5-[3-(1-hydroxybut-2-yn-1-yl)phenyl]-3-methyl-3,5-dihydro-4H-imidazol-4-one;

2-amino-5-[4-(difluoromethoxy)phenyl]-5-[3-(1,4-dihydroxybut-2-yn-1-yl)phenyl]-3-methyl-3,5-dihydro-4H-imidazol-4-one;

(5R)-2-amino-5-[3-(difluoromethoxy)phenyl]-5-[4-(difluoromethoxy)phenyl]-3-methyl-3,5-dihydro-4H-imidazol-4-one;

2-amino-5-[4-(difluoromethoxy)phenyl]-5-[3-(2,2-dimethyl-3-oxocyclobutyl)phenyl]-3-methyl-3,5-dihydro-4H-imidazol-4-one;

2-amino-5-[4-(difluoromethoxy)phenyl]-3-methyl-5-[3-(3-oxocyclobutyl)phenyl]-3,5-dihydro-4H-imidazol-4-one;

2-amino-5-[4-(difluoromethoxy)phenyl]-5-[3-(3-hydroxycyclobutyl)phenyl]-3-methyl-3,5-dihydro-4H-imidazol-4-one;

methyl [3-(3-{2-amino-4-[4-(difluoromethoxy)phenyl]-1-methyl-5-oxo-4,5-dihydro-1H-imidazol-4-yl}phenyl)cyclobutyl]acetate; and methyl [3-(3-{2-amino-4-[4-(difluoromethoxy)phenyl]-1-methyl-5-oxo-4,5-dihydro-1H-imidazol-4-yl}phenyl)cyclobutylidene]acetate;

a tautomer thereof;

a stereoisomer thereof; and a pharmaceutically acceptable salt thereof.

* * * * *